US012551315B2

(12) United States Patent
Henderson et al.

(10) Patent No.: US 12,551,315 B2
(45) Date of Patent: Feb. 17, 2026

(54) TISSUE MARKING DEVICE AND METHODS OF USE THEREOF

(71) Applicant: DFC MEDICAL LLC, Houston, TX (US)

(72) Inventors: James Robert Henderson, Houston, TX (US); Christen Springs, Houston, TX (US); Michael Augustine, Houston, TX (US); Jennifer Anderson, Houston, TX (US); Brian Walsh, Houston, TX (US); Elaina Becher, Houston, TX (US); Byron Smith, Nashville, TN (US)

(73) Assignee: DFC MEDICAL LLC, Houston, TX (US)

( * ) Notice: Subject to any disclaimer, the term of this patent is extended or adjusted under 35 U.S.C. 154(b) by 41 days.

(21) Appl. No.: 17/971,250

(22) Filed: Oct. 21, 2022

(65) Prior Publication Data

US 2023/0064178 A1 Mar. 2, 2023

Related U.S. Application Data

(63) Continuation of application No. PCT/US2021/028850, filed on Apr. 23, 2021.

(60) Provisional application No. 63/014,265, filed on Apr. 23, 2020.

(51) Int. Cl.
*A61B 90/00* (2016.01)

(52) U.S. Cl.
CPC ...... *A61B 90/39* (2016.02); *A61B 2090/3908* (2016.02); *A61B 2090/3966* (2016.02); *A61B 2090/3987* (2016.02); *A61B 2090/3991* (2016.02)

(58) Field of Classification Search
CPC ............ A61B 90/39; A61B 2090/3908; A61B 2090/3966; A61B 2090/3987; A61B 2090/3991
See application file for complete search history.

(56) References Cited

U.S. PATENT DOCUMENTS

| | | | |
|---|---|---|---|
| 5,556,410 | A | 9/1996 | Mittermeir et al. |
| 6,544,269 | B2 | 4/2003 | Osborne et al. |
| 6,905,484 | B2 | 6/2005 | Buckman et al. |
| 8,437,834 | B2 | 5/2013 | Carr, Jr. |
| 8,718,745 | B2 | 5/2014 | Burbank et al. |
| 9,044,162 | B2 | 6/2015 | Jones et al. |

(Continued)

FOREIGN PATENT DOCUMENTS

| | | | |
|---|---|---|---|
| EP | 0824892 | A1 | 2/1998 |
| WO | 2020081798 | A1 | 4/2020 |

(Continued)

*Primary Examiner* — Keith M Raymond
*Assistant Examiner* — Patrick M Mehl
(74) *Attorney, Agent, or Firm* — BakerHostetler

(57) ABSTRACT

Disclosed herein are tissue marking devices and methods that enables marking a target tissue more than 24 hours prior to surgery. The tissue marking device includes a hook assembly having a compressed configuration and a deployed configuration and a handle assembly for positioning the hook assembly in a targeted tissue. The hook assembly may include a hook body comprising at least two hooks and a thread connected to the hook body. The handle assembly may include a handle body, a needle having a lumen, and a stylet having a lumen.

18 Claims, 57 Drawing Sheets

(56) References Cited

U.S. PATENT DOCUMENTS

| | | | | |
|---|---|---|---|---|
| 10,524,875 | B2 | 1/2020 | Hermann et al. | |
| 10,959,802 | B1 | 3/2021 | Henderson et al. | |
| 2004/0097981 | A1 * | 5/2004 | Selis | A61B 90/39 606/151 |
| 2005/0143674 | A1 | 6/2005 | Burbank et al. | |
| 2009/0000629 | A1 | 1/2009 | Hornscheidt et al. | |
| 2010/0030149 | A1 | 2/2010 | Carr, Jr. | |
| 2010/0130887 | A1 | 5/2010 | Selis | |
| 2010/0204570 | A1 | 8/2010 | Lubock | |
| 2010/0241177 | A1 * | 9/2010 | Schaller | A61F 2/4611 606/86 A |
| 2011/0152611 | A1 | 6/2011 | Ducharme et al. | |
| 2011/0319932 | A1 | 12/2011 | Avelar et al. | |
| 2014/0309522 | A1 | 10/2014 | Fullerton et al. | |
| 2017/0252060 | A1 * | 9/2017 | Ellingson | A61B 90/11 |
| 2017/0296294 | A1 | 10/2017 | Hermann et al. | |
| 2018/0035914 | A1 | 2/2018 | Fullerton et al. | |
| 2018/0126156 | A1 * | 5/2018 | Sparks | A61B 5/283 |
| 2020/0078194 | A1 * | 3/2020 | Feezor | A61F 2/186 |
| 2020/0113646 | A1 * | 4/2020 | Hermann | A61B 90/50 |
| 2020/0121414 | A1 | 4/2020 | Springs et al. | |

FOREIGN PATENT DOCUMENTS

| | | | | |
|---|---|---|---|---|
| WO | WO-2020068658 | A1 * | 4/2020 | A61B 17/3421 |
| WO | WO 2021/217007 | A1 | 10/2021 | |

* cited by examiner

TISSUE MARKING DEVICE AND METHODS OF USE THEREOF

PRIORITY

This patent application is a bypass continuation under 35 U.S.C. § 111a of PCT Application No. PCT/US2021/028850, entitled "TISSUE MARKING DEVICE AND METHODS OF USE THEREOF", filed Apr. 23, 2021, which claims the benefit under 35 U.S.C. § 119 (*e*) of U.S. Patent Application Ser. No. 63/014,265, entitled "Tissue Marking Device and Methods of Use Thereof," filed on Apr. 23, 2020. The above-referenced applications are incorporated herein by reference in their entireties.

FIELD

The present disclosure relates generally to surgical tissue identification and removal, and more specifically, to a marking specific tissues within a breast at a time prior to removal of the tissue by surgery.

BACKGROUND

Tissue marking is used to externally indicate to a surgeon which tissue is to be tracked or removed, such as a tumor or mass. For example, after a breast biopsy determining that a tissue is cancerous and needs to be removed, a tissue marking device with a single hook attached to a rigid wire is inserted such that the wire extends outside the breast. The tissue marking device provides an external indication of the location of the tumor for the surgeon.

However, the standard tissue marking device has many limitations. Using current technology, the tissue must be marked on the same day, just prior to surgery to avoid displacing the hook. This leads to an extended time that the patient must be at the hospital. Coordinating schedules of Radiology, Surgery, and the Operating room staff leads to inefficiencies and affects patient satisfaction.

Accordingly, there is a need for a tissue marking device that is not prone to movement once in place such that it may be placed in a patient more than 24 hours before a surgery to remove the tissue.

BRIEF SUMMARY

The disclosure provides for a tissue marking device and methods of marking a tissue. The tissue marking device may include a hook assembly having a compressed configuration and a deployed configuration and a handle assembly for positioning the hook assembly in a targeted tissue. In an aspect, the hook assembly may include a hook body comprising at least two hooks, a retention mechanism, and a thread connected to the hook body. In one aspect, a metal thread may be welded, crimped, swagged, kinked, UV bounded, laser welded, or joined by any of means suitable for bonding metals to the proximal end of the hook body to form the hook assembly. In another aspect, the handle assembly may include a handle body having a proximal end and a distal end, a plunger having a locking mechanism, a needle having a lumen with an open first end and a second end, and a stylet having a lumen with an open first end and a second end. In an aspect, the hook body and the stylet are within the lumen of the needle and the thread is within the lumen of the stylet when the hook assembly is in the compressed configuration.

Further provided herein is a method of marking a target tissue in a patient. In an aspect, the method may include inserting a needle of the tissue marking device into a patient, confirming the location of the needle such that the hook body is near the target tissue, unlocking the locking mechanism on the handle body, depressing the plunger to extend the hook body past the needle and open the at least two hooks and retention mechanism to embed the hook body in the target tissue, and removing the needle and the stylet from the patient.

In another aspect, the method of marking a target tissue in a patient may include implanting a hook assembly of a tissue marking device into a target tissue of a patient. In this aspect, the hook assembly is operable to absorb compression without migrating more than 1 cm within the target tissue. In another aspect, the hook assembly is operable to allow the patient to have surgery to remove the hook assembly on a separate day from implantation.

Additional aspects and features are set forth in part in the description that follows, and will become apparent to those skilled in the art upon examination of the specification or may be learned by the practice of the disclosed subject matter. A further understanding of the nature and advantages of the disclosure may be realized by reference to the remaining portions of the specification and the drawings, which forms a part of this disclosure.

DESCRIPTION OF THE DRAWINGS

The description will be more fully understood with reference to the following figures, which are presented as variations of the disclosure and should not be construed as a complete recitation of the scope of the disclosure, wherein.

DETAILED DESCRIPTION

Figure 1A:
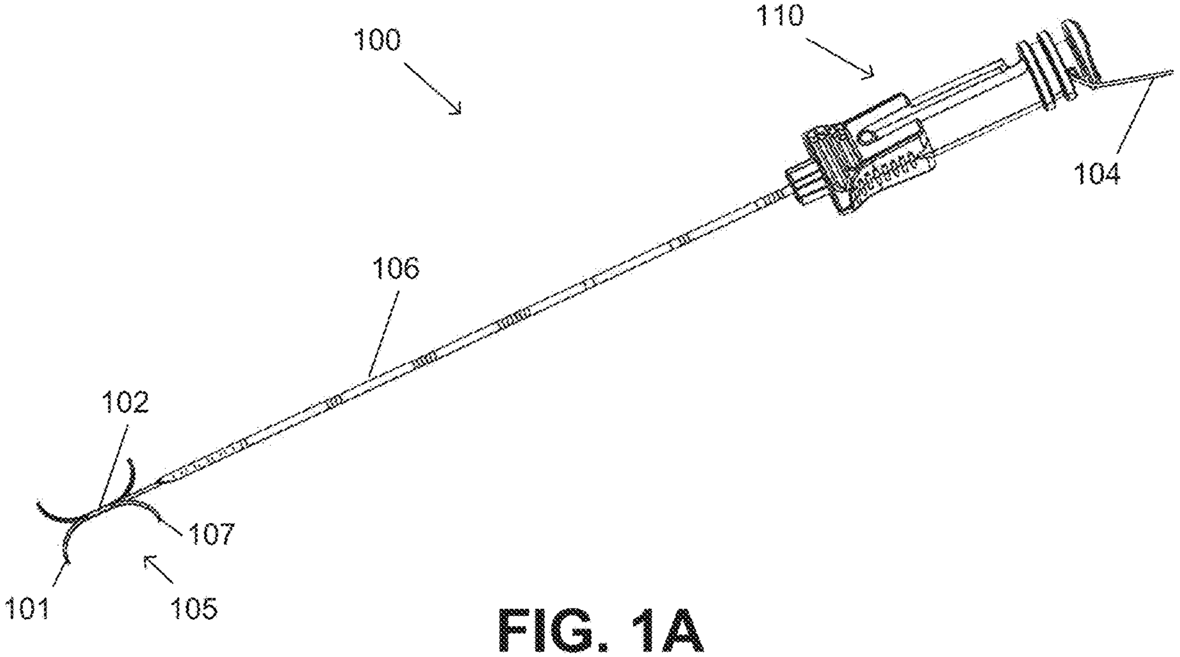
FIG. 1A is a perspective view of the tissue marking device in one variation.

The tissue marking device and method of use will be understood, both as to its structure and operation, from the accompanying drawings, taken in conjunction with the accompanying description. It is noted that, for purposes of illustrative clarity, certain elements in various drawings may not be drawn to scale. Several variations of the device are presented herein. It should be understood that various components, parts, and features of the different variations may be combined together and/or interchanged with one another, all of which are within the scope of the present application, even though not all variations and particular variations are shown in the drawings. It should also be understood that the mixing and matching of features, elements, and/or functions between various variations is expressly contemplated herein so that one of ordinary skill in the art would appreciate from this disclosure that the features, elements, and/or functions of one variation may be incorporated into another variation as appropriate, unless described otherwise.

For purposes of this description, "distal" refers to the end extending into a body and "proximal" refers to the end extending out of the body.

For purposes of this description "connected to" includes two components being directly connected or indirectly connected with intervening components.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. In some cases, synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any example term.

In traditional lumpectomy procedures, a localization wire is placed by a radiologist on the same day of the surgical procedure. This protocol requires the patient to go through two procedures in two separate departments on the same day. For the patient, this leads to increased anxiety levels and a reduction in satisfaction. For the facility, this can lead to lost revenue from scheduling difficulties. Wire-based localization technologies are also mechanically deficient. Wires can move during the long procedure day and are uncomfortable and awkward for the patient. It is not possible to schedule the radiological and surgical procedures on separate days using wire-based localization.

Capital equipment technologies require the use of expensive equipment (i.e. capital) to separate the procedure days. For example, these capital equipment systems use expensive technology like radar or magnets, combined with an external hardware system to localize the lesion. These technologies are expensive and have barriers to entry for the user. The facility must absorb the cost of the capital component to implement the technology and the cost of the actual treatment materials exceeds the available reimbursement. There is currently no simple, "low-cost" and/or single-use solution for breast lesion localization to be treated on a separate day from surgery.

The disclosed tissue marking device and methods of use thereof provides for the rapid marking of tissue more than 24 hours prior to the surgery. The tissue marking device provides a "low-cost" and single-use alternative to capital equipment technologies and provides for the separation of treatment days as an alternative to wire-based localization. For example, the tissue marking device uses a hook assembly with superior pull force strength to minimize migration and absorb compression and uses a flexible thread instead of a wire. In particular, the hook assembly is operable to absorb compression without migrating more than 1 cm within the target tissue. These features, described in detail below, allow for the device to be placed on a separate day than the surgery to remove the target tissue. In addition, the tissue marking device allows the patient to move without discomfort or risk of dislocating the hook marking the target tissue. Moreover, the tissue marking device is a simple, easy to use, handheld device for marking target tissue and does not require investment of any expensive equipment such as radar or magnets. The tissue marking device is an economically effective solution for the clinical, scheduling, and patient satisfaction issues associated with the current standard. In some variations, the tissue marking device overcomes one or more of the above-listed problems commonly associated with conventional wire marker devices and capital equipment technologies.

FIG. 1 depicts a side view of a tissue marking device for marking a target tissue in one variation. In various variations the target tissue may be within a breast. Examples of target tissue include lesions, cancerous and non-cancerous tumors, or masses.

Figure 1B:
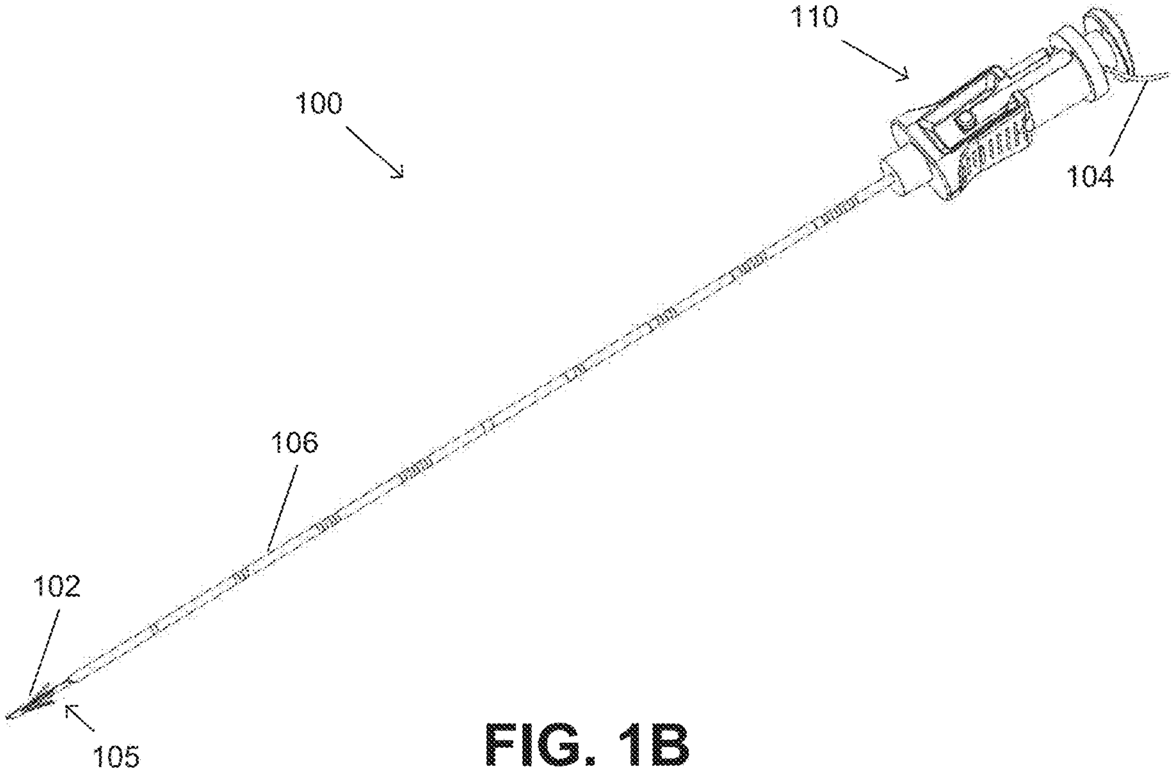
FIG. 1B is a perspective view of the tissue marking device in one variation.

As seen in FIGS. 1A-1B, the tissue marking device 100 includes a handle assembly 110 and a hook assembly 105. In a variation, the handle assembly 110 includes a handle body 111, a needle 106, and a stylet 108. The hook assembly 105 includes a hook body 102 connected to a thread 104. The handle assembly 110 is used to insert and deploy the hook assembly 105 at the target tissue and allow for easy removal of the handle assembly 110 once the hook assembly 105 is deployed. The hook assembly remains in the patient, with the hook body 102 located at the target tissue and the thread 104 extending from the hook body to outside the patient's body. In a variation, the thread 104 may be flexible such that it can remain external to the body more than 24 hours before surgery without risking migration of the hook body 102 if the thread 104 is touched by the patient. In another variation, the hooks 101 on the hook body 102 may prevent unintended migration of the hook body 102 after the hook assembly 105 has been placed and deployed.

As may be appreciated, the tissue marking device 100 described herein (and the needle 106 thereof) may be of any desired size (e.g., length) to suit a particular application and may generally vary depending on the depth of the cancerous lesion. In a variation, the tissue marking device 100 has a length of at least 4.0 cm. In a variation, the tissue marking device 100 has a length of at least 4.5 cm. In a variation, the tissue marking device 100 has a length of at least 5.0 cm. In a variation, the tissue marking device 100 has a length of at least 5.5 cm. In a variation, the tissue marking device 100 has a length of at least 6.0 cm. In a variation, the tissue marking device 100 has a length of at least 6.5 cm. In a variation, the tissue marking device 100 has a length of at least 7.0 cm. In a variation, the tissue marking device 100 has a length of at least 7.5 cm. In a variation, the tissue marking device 100 has a length of at least 8.0 cm. In a variation, the tissue marking device 100 has a length of at least 8.5 cm. In a variation, the tissue marking device 100 has a length of at least 9.0 cm. In a variation, the tissue marking device 100 has a length of at least 10.0 cm. In a variation, the tissue marking device 100 has a length of at least 10.5 cm. In a variation, the tissue marking device 100 has a length of at least 11.0 cm. In a variation, the tissue marking device 100 has a length of at least 11.5 cm. In a variation, the tissue marking device 100 has a length of at least 12.0 cm. In a variation, the tissue marking device 100 has a length of at least 12.5 cm. In a variation, the tissue marking device 100 has a length of at least 13.0 cm. In a variation, the tissue marking device 100 has a length of at least 13.5 cm. In a variation, the tissue marking device 100 has a length of at least 14.0 cm. In a variation, the tissue marking device 100 has a length of at least 14.5 cm. In a variation, the tissue marking device 100 has a length of at least 15.0 cm. In a variation, the tissue marking device 100 has a length of at least 15.5 cm. In a variation, the tissue marking device 100 has a length of at least 16.0 cm.

In a variation, the tissue marking device 100 has a length of less than or equal to 16.0 cm. In a variation, the tissue marking device 100 has a length of less than or equal to 15.5 cm. In a variation, the tissue marking device 100 has a length of less than or equal to 14.0 cm. In a variation, the tissue marking device 100 has a length of less than or equal to 14.5 cm. In a variation, the tissue marking device 100 has a length of less than or equal to 13.0 cm. In a variation, the tissue marking device 100 has a length of less than or equal to 13.5 cm. In a variation, the tissue marking device 100 has a length of less than or equal to 12.0 cm. In a variation, the tissue marking device 100 has a length of less than or equal to 12.5 cm. In a variation, the tissue marking device 100 has a length of less than or equal to 11.0 cm. In a variation, the tissue marking device 100 has a length of less than or equal to 11.5 cm. In a variation, the tissue marking device 100 has a length of less than or equal to 10.0 cm. In a variation, the tissue marking device 100 has a length of less than or equal to 10.5 cm. In a variation, the tissue marking device 100 has a length of less than or equal to 9.0 cm. In a variation, the tissue marking device 100 has a length of less than or equal to 9.5 cm. In a variation, the tissue marking device 100 has a length of less than or equal to 8.0 cm. In a variation, the tissue marking device 100 has a length of less than or equal to 8.5 cm. In a variation, the tissue marking device 100 has a length of less than or equal to 7.0 cm. In a variation, the tissue marking device 100 has a length of less than or equal to 6.5 cm. In a variation, the tissue marking device 100 has a length of less than or equal to 6.0 cm. In a variation, the tissue marking device 100 has a length of less than or equal to 5.5 cm. In a variation, the tissue marking device 100 has a length of less than or equal to 5.0 cm. In a variation, the tissue marking device 100 has a length of less than or equal to 4.5 cm. In a variation, the tissue marking device 100 has a length of less than or equal to 4.0 cm.

Figure 2A:
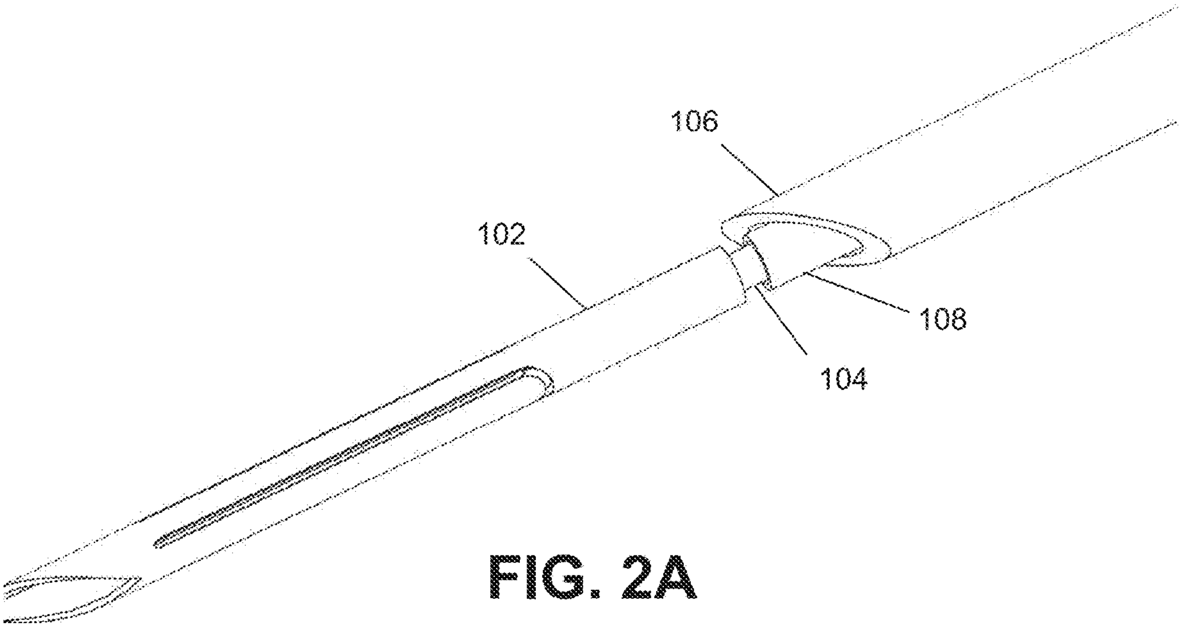
FIG. 2A is a view of the distal end of the tissue marking device with the hook body in the compressed configuration as it would be seen if inside the needle, in one variation.
Figure 2B:
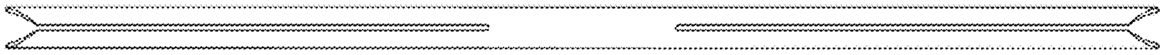
FIG. 2B is a view of the hook body in the compressed configuration as it would be seen if inside the needle, in one variation.
Figure 2C:
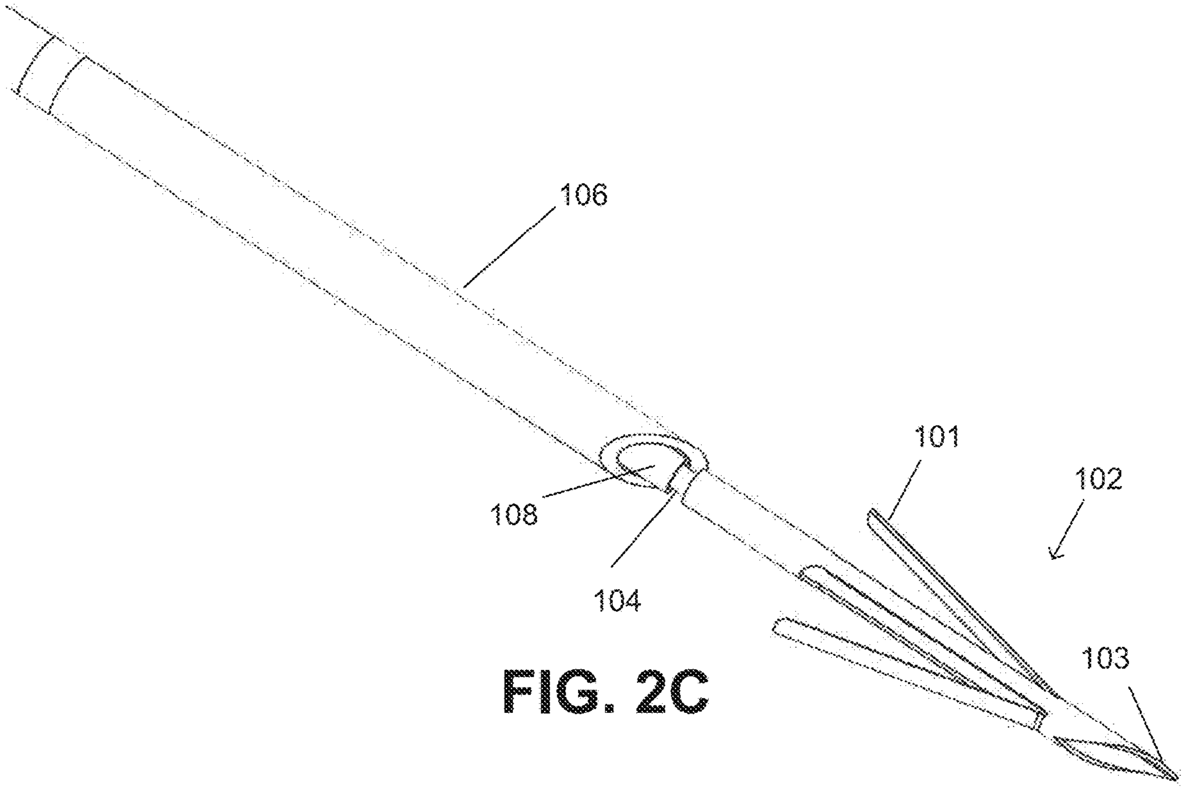
FIG. 2C is a view of the distal end of the tissue marking device with the hook assembly in the deployed configuration, in one variation.
Figure 2D:
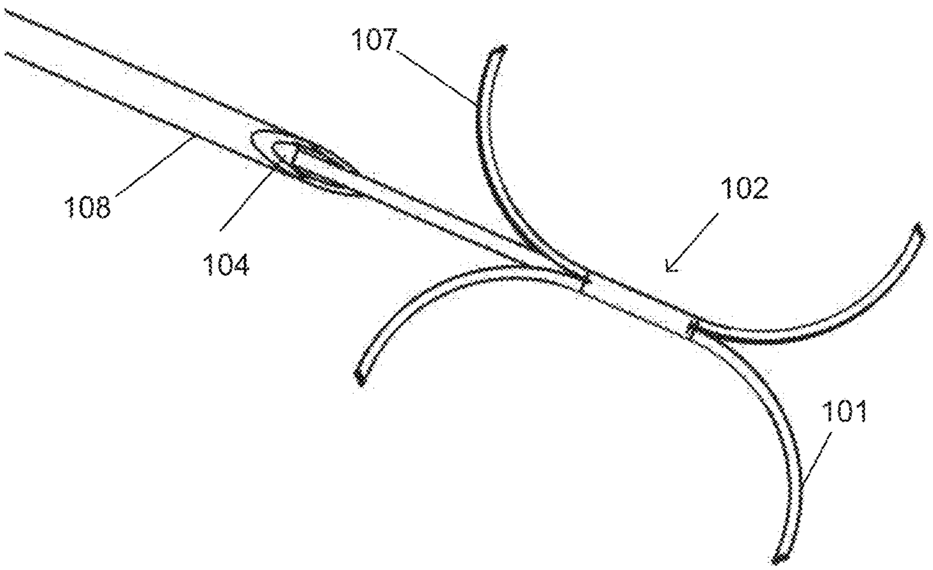
FIG. 2D is a view of the distal end of the tissue marking device with the hook assembly in the deployed configuration, in one variation.

The hook assembly 105, by way of the hook body 102, can be in a compressed configuration or a deployed configuration. In the compressed configuration, the hooks 101 and/or retention mechanism 107 of the hook body 102 are compressed together such that the hook assembly 105 can be loaded and fit within the lumen of the needle 106. For example, the hook body 102 in the compressed configuration generally looks like a tube. In a variation, the hooks 101 and/or retention mechanism 107 of the hook body 102 are forcibly compressed by the lumen of the needle 106. FIGS. 2A-2B show the hook body 102 in the compressed configuration, in some variations, as it would be seen if fully contained within the needle 106 of the handle assembly 110. Once the handle assembly 110 pushes the stylet 108, the stylet 108 pushes the hook body 102 out of the needle 106 and the hooks 101 and/or retention mechanism 107 expand or deploy because they are no longer compressed by the needle 106. FIGS. 2C-2D show the hook body 102 in the deployed configuration, in some variations, prior to the handle assembly 110 being removed.

The hook body 102 has a proximal end and a distal end. The hook body 102 may include at least two hooks 101 at the distal end of the hook body 102. FIGS. 3A-3F show non-limiting examples of distal hook shapes, numbers, and configurations that may be included on the hook body. In a variation, the at least two hooks 101 may be separated by 180°. In a variation, the at least two hooks 101 may be separated by 120°. In a variation, the at least two hooks 101 may be separated by 90°. In a variation, the at least two hooks 101 may be separated by 45°. In a variation, the at least two hooks 101 may be separated by a combination of 180°, 120°, 90° and/or 45°. In some variations, the at least two hooks 101 may be equidistant from one another.

Figure 3A:
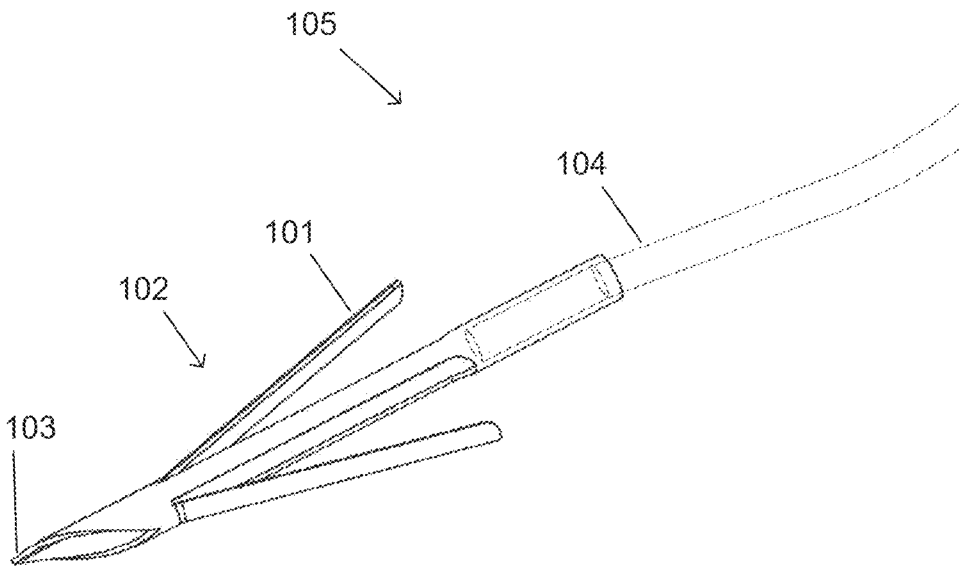
FIG. 3A is a side view of a non-removable hook assembly with three hooks in one variation.
Figure 3B:
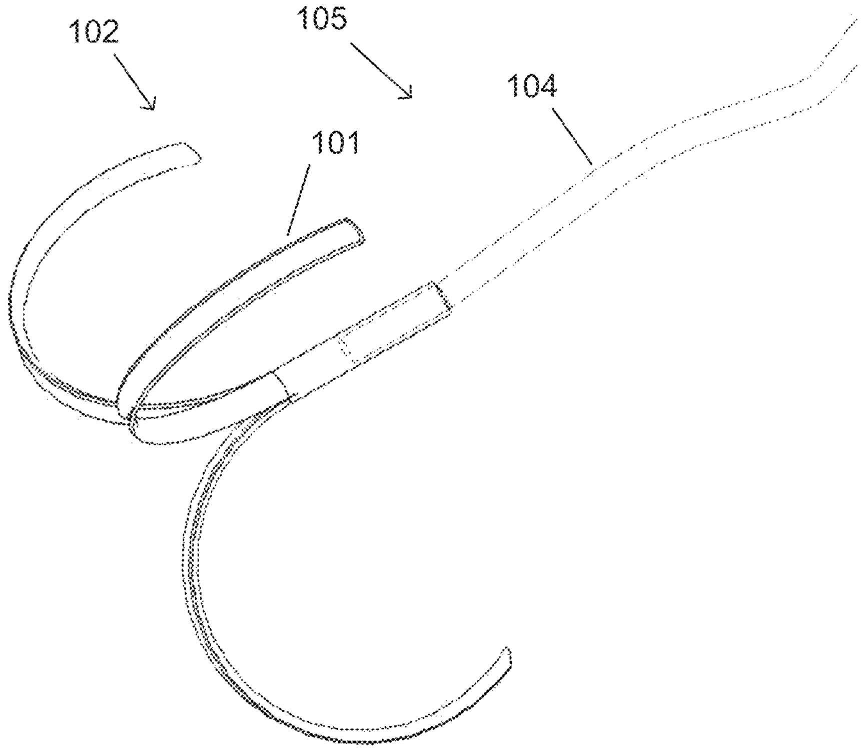
FIG. 3B is a side view of a hook assembly with three hooks in one variation.
Figure 3C:
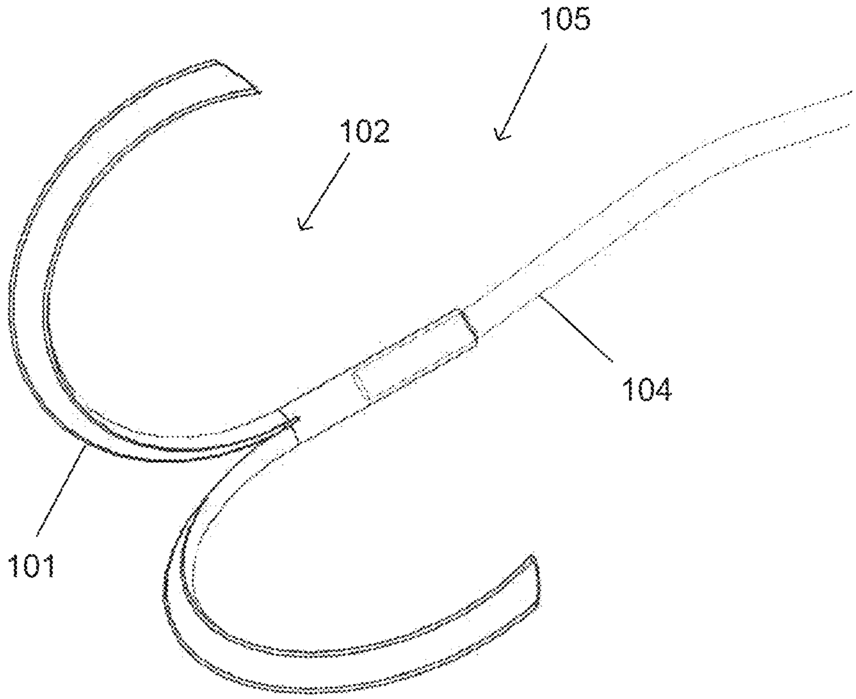
FIG. 3C is a side view of a hook assembly with two hooks in a 90° configuration in one variation.
Figure 3D:
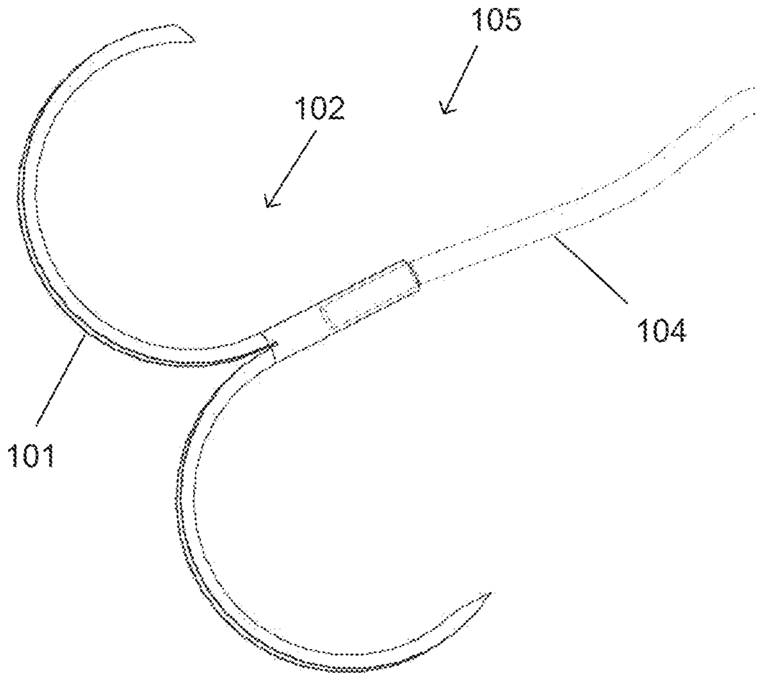
FIG. 3D is a side view of a hook assembly with two hooks in a 180° configuration in one variation.

In some variations, the hook body may include at least two hooks 101. In some variations, the hook body may include at least three hooks 101. In some variations, the hook body may include at least four hooks 101. In some variations, the hook body may include at least five hooks 101. In a variation, the hook body 102 may include three hooks 101, as seen in FIG. 3A or FIG. 3B. In a variation, two of the hooks may be separated by 180° while a third hook may be 90° from each of the other two hooks. In a variation, three hooks may be separated by 90° or 45°. In another variation, the hook body 102 may include two hooks, as seen in FIG. 3C, where the two hooks 101 are separated by 90°. In yet another variation, the hook body 102 may include two hooks, as seen in FIGS. 3D-3F, where the two hooks 101 are separated by 180°.

The at least two hooks 101 may have a straight configuration, a rounded configuration, a curved configuration, or any configuration sufficient to retain the hook body within the target tissue and absorb compression forces. In a variation, the hooks 101 may have a rounded or curved configuration, as seen in FIGS. 3E-3F. In a variation, the hooks 101 may be offset from the hook body by about 45°. In a variation, the hooks 101 may be offset from the hook body by about 90°. FIG. 3A is an example of a hook body 102 with hooks 101 in a straight configuration and FIGS. 3B-3D are examples of a hook body 102 with hooks 101 in a curved configuration. In one variation, the hook body 102 may further include a pointed distal end 103 extending past the hooks 101.

In a variation, the hook body may be non-removable. In other variations, the hook body may not be retracted, repositioned, or adjusted once deployed in the target tissue. In this variation, the hook assembly 105 may not be removed from the body except through surgery. The handle assembly 110 may not be used to remove or re-place the hook assembly 105. The hook body may not include any sharp ends that would otherwise facilitate movement of the hook assembly within the tissue.

Figure 3E:
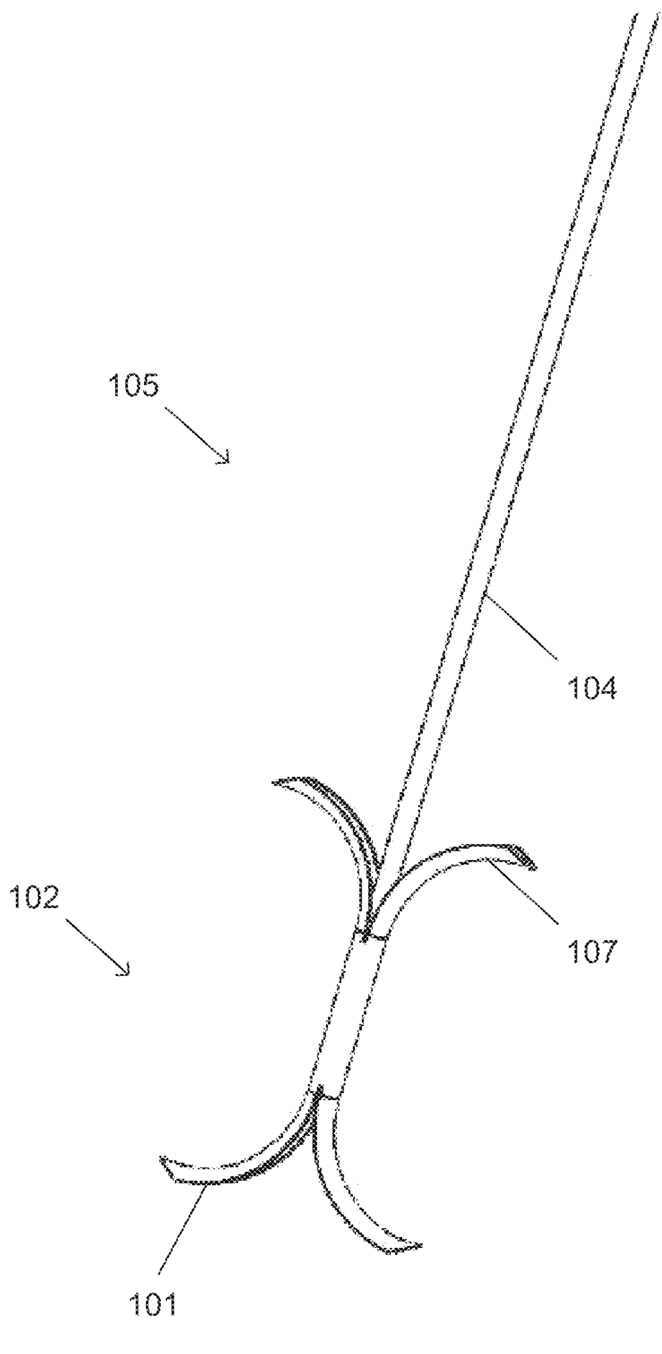
FIG. 3E is a side view of a hook assembly with two hooks in a 180° configuration and a retention mechanism with two proximal hooks in one variation.
Figure 3F:
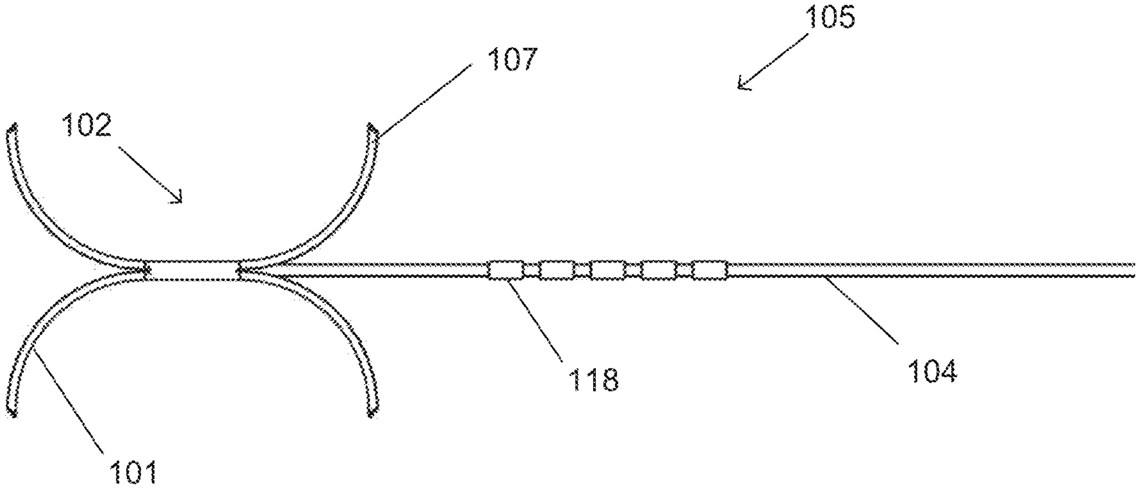
FIG. 3F is a side view of a hook assembly with two hooks in a 180° configuration and a retention mechanism with two proximal hooks in one variation.

To aid in restricting migration of the hook assembly 105, the hook body 102 may further include a retention mechanism 107 at the proximal end of the hook body 102, as seen in FIGS. 3E-3F. The retention mechanism may prevent the hook body 102 or hook assembly 105 from retracting back into the needle 106 once the hook assembly has been deployed. In addition, the retention mechanism may prevent the hook body 102 or hook assembly 105 from migrating once the hook assembly has been deployed and the handle assembly has been removed. This may allow the hook assembly 105 to remain in the patient for an extended period of time, such that the placement of the hook assembly may occur on a separate day from the surgery to remove the target tissue.

The retention mechanism 107 may have any shape or structure that absorbs compression, facilitates retention of the hook assembly 105 within the target tissue, and prevents the hook body 102 from being retracted into the needle 106 or migrating within the target tissue. In some variations, the retention mechanism 107 may have a rounded hook shape, curved hook shape, a straight hook shape, an elbow shape, or a T-shape. In a variation, the retention mechanism 107 may include one proximal hook. In a variation, the retention mechanism 107 has a rounded or curved hook shape, as seen in FIGS. 3E-3F. In a variation, the retention mechanism 107 may include two proximal hooks. In a variation, the retention mechanism 107 may include three proximal hooks. In a variation, the retention mechanism 107 may include four proximal hooks. The retention mechanism 107 may be laser cut from the same nitinol tube that the hooks are cut, such that the hooks, retention mechanism, and hook body are a single element. In a variation, the retention mechanism 107 may be the same length as the hooks 101. In a variation, the retention mechanism 107 may be shorter than the hooks 101. In a variation, the retention mechanism 107 may be longer than the hooks 101.

In a variation, the hook body 102 may include two distal hooks 101 and a retention mechanism 107 with two proximal hooks, generally forming a four hook/arm configuration, or an "H" configuration, as seen in FIGS. 3E-3F. In this variation, the hook body optimizes resistance to migration while also allowing flex inside the tissue during normal patient movements. In an example, the arms flex when compressed with near zero migration. In a variation, the two distal hooks and the two proximal hooks are located in the same plane. In another variation, the two distal hooks and the two proximal hooks are offset by an angle such that they are not in the same plane. For example, the anterior and posterior side of the hooks may help with compression from the top and bottom of the breast. In another variation, two 2D/planner elements containing one distal hook and one proximal hook may be heat set to the desired bend radius and bonded together at the apex.

The hook body allows for the hook assembly to absorb compression forces without migrating a distance that would require re-localization by re-implantation of the hook assembly. In a variation, the hook assembly is operable to allow the patient to have surgery to remove the hook assembly on a separate day from localization/implantation. The ability to absorb compression forces may permit the patient to participate in normal activity between the time of localization/implantation of the hook assembly and the time of surgery to remove the target tissue. Non-limiting examples of normal activity include sleeping (face down if desired), rolling over, sexual activity, taking care of loved ones (for example, kids), exercising, accidental bumping, and/or lifting heaving objects.

The hook assembly 105, by way of the hook body 102, is operable to absorb compression forces without migrating more than 1.5 cm from the original placement within the target tissue. In a variation, the hook assembly is operable to absorb compression without migrating more than 1 cm within the target tissue. In a variation, the hook assembly is operable to absorb compression without migrating more than 8 mm within the target tissue. In a variation, the hook assembly is operable to absorb compression without migrating more than 5 mm within the target tissue. In a variation, the hook assembly is operable to absorb compression without migrating more than 3 mm within the target tissue. In a variation, the hook assembly is operable to absorb compression without migrating more than 2 mm within the target tissue. In a variation, the hook assembly is operable to absorb compression without migrating more than 1 mm within the target tissue. In a variation, the hook assembly is operable to absorb compression without migrating more than 0.5 mm within the target tissue.

In a variation, the hook body 102 may have a length of 2 mm to 8 mm in the compressed configuration. In a variation, the hook body has a length of at least 2 mm. In a variation, the hook body has a length of at least 3 mm. In a variation, the hook body has a length of at least 4 mm. In a variation, the hook body has a length of at least 5 mm. In a variation, the hook body has a length of at least 7 mm. When in the compressed configuration, the hook body 102 has a diameter sufficient to fit within the lumen of a needle 106. In a variation, the hook body 102 may have a diameter of less than 1 mm in the compressed configuration. In a variation, each hook 101 may have a length of at least 1 mm. In a variation, each hook 101 may have a length of at least 2 mm. In a variation, each hook 101 may have a length of at least 3 mm. In a variation, each hook 101 may have a length of at least 4 mm. In a variation, each hook 101 may have a diameter of less than 1 mm. In a variation, each hook 101 may have a diameter of less than 1 mm. In a variation, each hook 101 may have a diameter of less than 0.75 mm. In a variation, each hook 101 may have a diameter of less than 0.5 mm. In a variation, the retention mechanism 107 may have a length of at least 1 mm. In a variation, the retention mechanism 107 may have a length of at least 3 mm.

In a variation, the hook body 102 may be formed from a tube that has been laser cut to form the hooks 101. In this variation, the hooks 101 and the hook body 102 are a single element. Therefore, the hooks 101 may be integral to the hook body 102 and do not need to be attached together or attached to the hook body. This may allow the hook body 102 to take the shape of a tube when in the compressed configuration. Without being limited to a particular theory, laser cutting the hooks 101 into the hook body 102 allows for the hook body 102 to have a compressed configuration in the shape of a tube and a deployed configuration with the hooks 101 expanded, for example, as seen in FIGS. 2A and 2C. The hooks 101 may be pre-formed in the deployed configuration and may need to be physically compressed to be in the compressed configuration, such as being compressed by the lumen of the needle 106. In a variation, the hook body 102 may be formed from a nitinol tube.

In another variation, the hook body 102 may be formed from a tube that has been laser cut to form the hooks 101 and retention mechanism 107. In this variation, the hooks 101, the retention mechanism 107, and the hook body 102 are a single element. In some examples, the hooks 101 and retention mechanism 107 have the same shape, and may generally form four hooks/arms cut from a single tube, as seen in FIG. 3E. Therefore, the hooks 101 and retention mechanism 107 may be integral to the hook body 102 and do not need to be attached together or attached to the hook body. This may allow the hook body 102 to take the shape of a tube when in the compressed configuration. Without being limited to a particular theory, laser cutting the hooks 101 and retention mechanism 107 into the hook body 102 allows for the hook body 102 to have a compressed configuration in the shape of a tube and a deployed configuration with the hooks 101 and retention mechanism 107 expanded, for example, as seen in FIGS. 2B and 2D. The hooks 101 and retention mechanism 107 may be pre-formed in the deployed configuration and may need to be physically compressed to be in the compressed configuration, such as being compressed by the lumen of the needle 106. In a variation, the hook body 102 with integral hooks 101 and retention mechanism 107, may be formed from a nitinol tube.

In a variation, the hook body 102 may include at least one radiopaque marker. In some variations, the hooks 101 may include a radiopaque marker. In other variations, the hook body 102 itself may be used as a radiopaque marker. It will be appreciated that the radiopaque markers may be configured to communicate a set distance to further facilitate the measurement of target tissue, to distinguish between multiple marked tissues, to demonstrate the distance of the hook from the targeted lesion, or indicate a distance from the hook body to a biopsy marker clip. It will be appreciated that any arrangement of radiopaque markers is contemplated.

The hook assembly 105 further includes a thread 104 connected to the hook body 102. The thread 104 may be connected to the hook body 102 such that it remains attached to the hook body 102 when the hook assembly 105 is embedded in a targeted tissue. In some variations, the thread 104 may be welded, crimped, swagged, kinked, UV bounded, laser welded, or joined by any of means suitable for bonding metals onto the hook body 102.

The thread may be impervious to heat, completely flexible, resistant to cutting, provide a secure connection to the hook body, viewable on imaging, include marker bands, and have a proximal end that can be secured to the patient's breast. In some variations, the thread does not have to be secured to breast. In some examples, the thread may eliminate transection concern while providing heat resistance and optimal strength during surgery. The thread may be flexible or non-rigid such that it may prevent the hook body from unintentionally moving or being driven past the target tissue. In a variation, the thread 104 may be flexible yet strong. For example, the thread 104 can be flexible such that it can bend when outside the body and therefore not be at risk of being moved inside the body if touched or bumped outside the body of the patient. The thread 104 can be heat resistant such that it is not at risk of being severed if near a cauterizer and can be tough enough to not be at risk of being cut by a scalpel. In variations, the thread 104 may be made from a shape memory material, such as a shape memory alloy (e.g., nitinol), though other variations are not so limited. Non-limiting examples of the material that may make up the thread include chromium cobalt, stainless steel, nitinol, and Kevlar. In a variation, the thread 104 is a metal thread. In one variation, the thread is made of chromium cobalt or a cobalt-chrome alloy. In a particular variation, the thread is made of nitinol.

Figure 18:
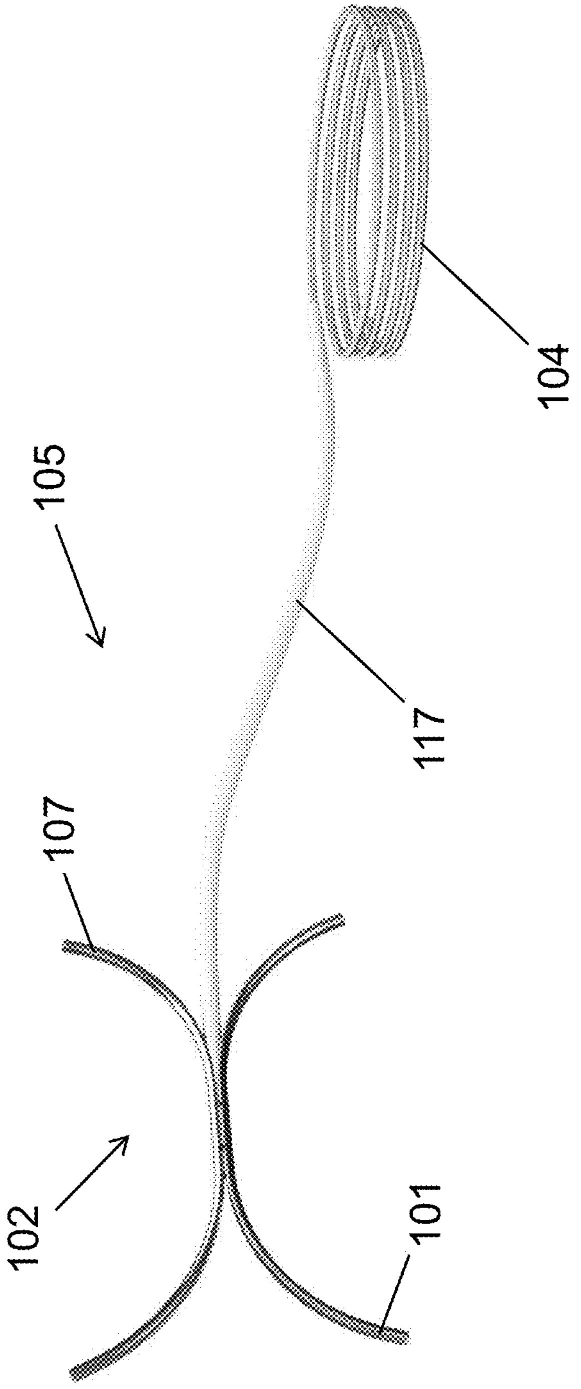
FIG. 18 is a perspective view of a hook assembly and a thread with a sleeving, according to an illustrative embodiment.

In a variation, the thread 104 may include a sleeving 117 along a length of the thread, as depicted, for example, in FIG. 18. The sleeving 117 may generally operate so as to electrically insulate at least a portion of the thread 104. In such embodiments, the sleeving will not result in a spark, fire, or other effect not allowable during surgery. In a variation, the sleeving 117 may further provide one or more properties, such as strength, durability, rigidity, and/or stiffness to the sleeved portion of the thread 104 without significantly or negatively affecting the profile of the thread 104. In a variation, the sleeving 117 may eliminate transection concern of the thread 104 while providing heat resistance and optimal strength during surgery. The sleeving 117 can be heat resistant such that it is not at risk of being severed if near a cauterizer and can be tough enough to not be at risk of being cut by energy-generating or sensing devices, including surgical cutting instruments such as a Bovie device.

In a variation, the sleeving 117 may be disposed about a distal portion of the thread 104 (i.e., a portion of the thread internal to the body). In a variation, a proximal portion of the thread 104 (i.e., a portion of the thread external to the body after removal of the needle and stylet) may be without such a sleeving.

As previously described, the sleeving 117 may electrically insulate the sleeved portion of the thread 104. The sleeving 117 may advantageously protect the thread 104 from energy-generating or sensing devices, such as those often used in lumpectomy procedures. In this way, the sleeving 117 may protect the thread 104 from being inadvertently cut (e.g., by a Bovie device). The sleeving 117 may, in a variation, be designed so as to be readily visible. For example, the sleeving 117 may be formed with a color (e.g., white) that is easily recognizable in comparison to the unsleeved portion(s) of the thread 104. For example, the sleeving 117 may be formed of a first color and the thread 104 may be formed with a second, different color.

The sleeving 117 may have a length and/or wall thickness that is sufficient to provide one or more of the above-described advantages. In a variation, the sleeving 117 has a length of at least 5 cm. In a variation, the sleeving 117 has a length of at least 6 cm. In a variation, the sleeving 117 has a length of at least 7 cm. In a variation, the sleeving 117 has a length of at least 8 cm. In a variation, the sleeving 117 has a length of at least 10 cm. In a variation, the sleeving 117 has a length of at least 11 cm.

In some variations, the sleeving 117 has a length of less than or equal to 12 cm. In some variations, the sleeving 117 has a length of less than or equal to 11 cm. In some variations, the sleeving 117 has a length of less than or equal to 10 cm. In some variations, the sleeving 117 has a length of less than or equal to 9 cm. In some variations, the sleeving 117 has a length of less than or equal to 8 cm. In some variations, the sleeving 117 has a length of less than or equal to 7 cm. In some variations, the sleeving 117 has a length of less than or equal to 6 cm.

In a variation, the sleeving 117 has a wall thickness of about 0.005 cm. In a variation, the sleeving 117 has a wall thickness of at least 0.001 cm. In a variation, the sleeving 117 has a wall thickness of at least 0.003 cm. In a variation, the sleeving 117 has a wall thickness of at least 0.005 cm. In a variation, the sleeving 117 has a wall thickness of at least 0.007 cm. In a variation, the sleeving 117 has a wall thickness of at least 0.009 cm. In a variation, the sleeving 117 has a wall thickness of at least 0.010 cm.

In a variation, the sleeving 117 has a wall thickness is equal to or less than 0.020 cm. In a variation, the sleeving 117 has a wall thickness is equal to or less than 0.010 cm. In a variation, the sleeving 117 has a wall thickness is equal to or less than 0.009 cm. In a variation, the sleeving 117 has a wall thickness is equal to or less than 0.007 cm. In a variation, the sleeving 117 has a wall thickness is equal to or less than 0.005 cm. In a variation, the sleeving 117 has a wall thickness is equal to or less than 0.003 cm. In a variation, the sleeving 117 has a wall thickness is equal to or less than 0.001 cm.

In a variation, the sleeving 117 may be designed such that the outer wall thereof has a smooth, lubricious surface finish, which may aid in the delivery stage described herein. In a variation, the sleeving 117 may be positioned so as to abut the hook body 102. Put another way, in a variation, the sleeving 117 may generally extend about the thread 104 from adjacent the hook body 102 toward the proximal end of the thread 104.

In a variation, the sleeving 117 may be disposed about at least a portion of the thread 104 by cold-shrinking of the sleeving. In another variation, the sleeving 117 may be disposed about at least a portion of the thread 104 by heat-shrinking of the sleeving. In a variation, the sleeving 117 may be a heat-shrunk thermoplastic. In one variation, the sleeving 117 may be formed from polyethylene terephthalate (PET). In another variation, the sleeving 117 may be formed from fluorinated ethylene propylene (FEP). In still other variations, the sleeving 117 may be a formed from a spray-on ceramic or dip coating.

It is to be understood that the sleeving 117 described herein may, individually or in any combination, be incorporated and/or combined with any of the other features discussed herein or illustrated in the accompanying drawings. For avoidance of doubt, it is to be understood that although the sleeving 117 is only illustrated in FIG. 18, the sleeving 117 could be incorporated into and/or combined with any variations of the tissue marking devices described herein or illustrated in the accompanying drawings.

In variations, the sleeving 117 may be employed in combination with a thread 104 made from a memory shape material (e.g., nitinol). In one such variation, the sleeved portion(s) of the thread 104 (i.e., the portion(s) of the thread disposed within the sleeving 117) may otherwise prevent or retard the shape recovery characteristics of that portion of the thread, such as due to rigidity and/or stiffness imparted by the sleeving. Conversely, the unsleeved portion(s) of the thread 104 (i.e., the portion(s) of the thread not disposed within the sleeving 117) may have shape recovery characteristics imparted by the memory shape material (e.g., nitinol) of the thread.

The portion of the thread 104 external to the patient (i.e., proximal to the hook) may generally be unsleeved so as to exhibit shape recovery characteristics imparted by the memory shape material (e.g., nitinol) of the thread. The portion of the thread 104 internal to the patient may, on the other hand, be at least partially covered by the sleeving 117. As previously described, the extent to which the thread 104 extend into the patient may generally vary depending on the depth of the cancerous lesion. In variations, the internal portion of the thread 104 may include a sleeving 117 that covers all or less than all of the internal portion of the thread 104.

By way of non-limiting example, the internal portion of the thread 104 may include a sleeving 117 that covers at least 2 cm of the internal portion of the thread. In a variation, the internal portion of the thread 104 may include a sleeving 117 that covers at least 3 cm of the internal portion of the thread. In a variation, the internal portion of the thread 104 may include a sleeving 117 that covers at least 4 cm of the internal portion of the thread. In a variation, the internal portion of the thread 104 may include a sleeving 117 that covers at least 5 cm of the internal portion of the thread. In a variation, the internal portion of the thread 104 may include a sleeving 117 that covers at least 6 cm of the internal portion of the thread. In a variation, the internal portion of the thread 104 may include a sleeving 117 that covers at least 7 cm of the internal portion of the thread. In a variation, the internal portion of the thread 104 may include a sleeving 117 that covers at least 8 cm of the internal portion of the thread. In a variation, the internal portion of the thread 104 may include a sleeving 117 that covers at least 9 cm of the internal portion of the thread. In a variation, the internal portion of the thread 104 may include a sleeving 117 that covers at least 10 cm of the internal portion of the thread. In a variation, the internal portion of the thread 104 may include a sleeving 117 that covers at least 11 cm of the internal portion of the thread.

In a variation, the internal portion of the thread 104 may include a sleeving 117 that covers equal to or less than 11 cm of the internal portion of the thread. In a variation, the internal portion of the thread 104 may include a sleeving 117 that covers equal to or less than 10 cm of the internal portion of the thread. In a variation, the internal portion of the thread 104 may include a sleeving 117 that covers equal to or less than 9 cm of the internal portion of the thread. In a variation, the internal portion of the thread 104 may include a sleeving 117 that covers equal to or less than 8 cm of the internal portion of the thread. In a variation, the internal portion of the thread 104 may include a sleeving 117 that covers equal to or less than 7 cm of the internal portion of the thread. In a variation, the internal portion of the thread 104 may include a sleeving 117 that covers equal to or less than 6 cm of the internal portion of the thread. In a variation, the internal portion of the thread 104 may include a sleeving 117 that covers equal to or less than 5 cm of the internal portion of the thread. In a variation, the internal portion of the thread 104 may include a sleeving 117 that covers equal to or less than 4 cm of the internal portion of the thread. In a variation, the internal portion of the thread 104 may include a sleeving 117 that covers equal to or less than 3 cm of the internal portion of the thread. In a variation, the internal portion of the thread 104 may include a sleeving 117 that covers equal to or less than 2 cm of the internal portion of the thread.

Figure 19:
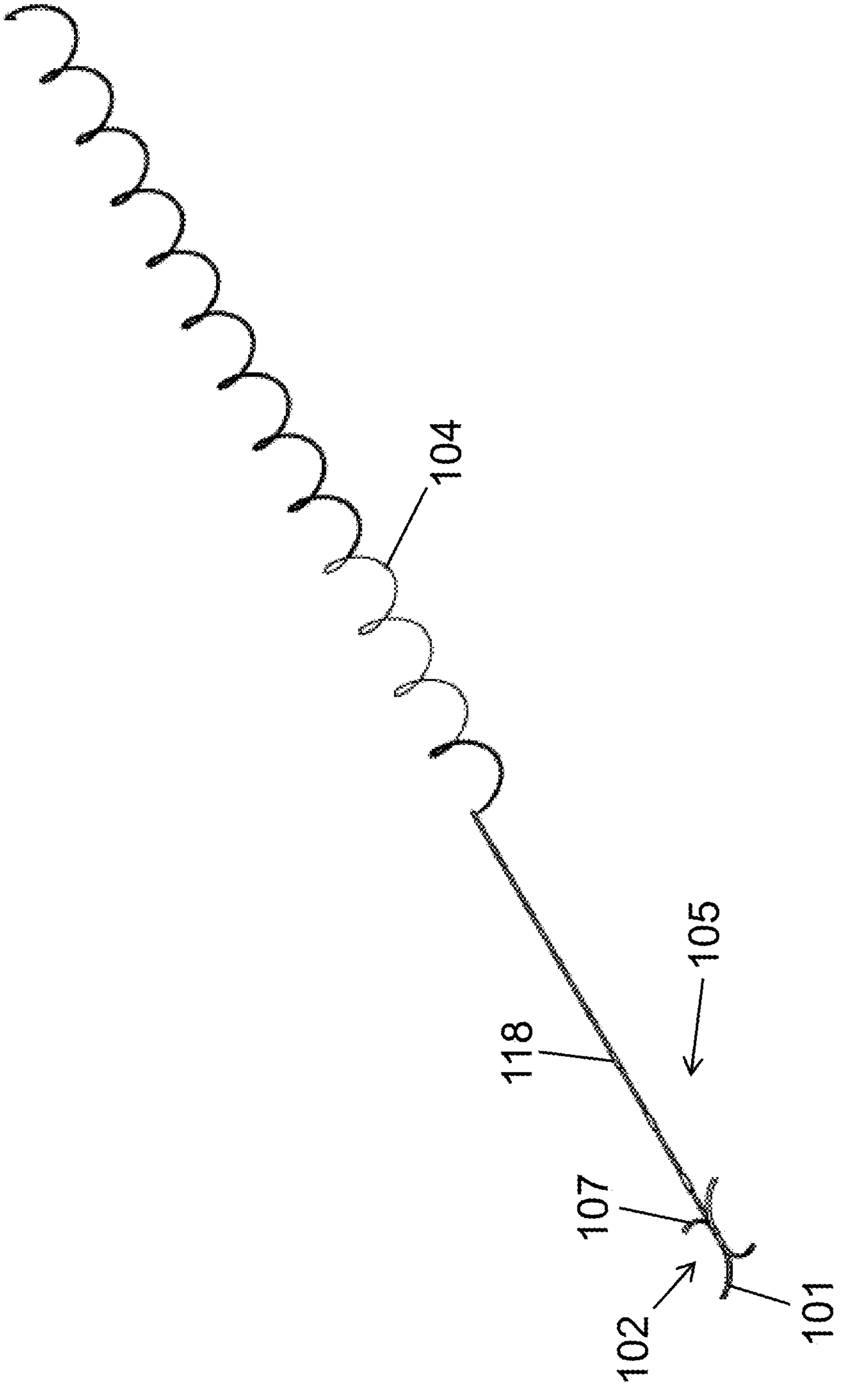
FIG. 19 is a perspective view of a hook assembly and a proximal portion of a thread coiling upon itself, according to an illustrative embodiment.

As previously described, in variations, the thread 104 may be made from a shape memory material, such as a shape memory alloy (e.g., nitinol). For purposes of this description, "shape memory material" refers to a material having shape recovery characteristics, including superelastic or pseudoelastic shape recovery characteristics. Put another way, the thread 104 may be formed of a material exhibiting the ability to avoid "setting" in a particular shape when deformed. In this way, at least a proximal portion of the thread 104 may be configured to form a preset shape in a defined area when unstressed. By way of non-limiting example, the thread 104 may be substantially coiled when unstressed, may elastically deform so as to be substantially straight when stressed, and may recover its coiled configuration when the deforming stress is removed. By way of non-limiting example, as seen for example in FIG. 19, the thread 104 may be configured to generally coil upon itself when unstressed.

The shape memory material from which the thread 104 may, in variations, be formed may be preset with a coiled shape (e.g., similar to a ribbon). Put another way, when unstressed, the thread 104 may be configured to automatically return to the preset, coiled shape. In a variation, presetting of the shape memory material from which the thread 104 is formed may include heat-setting.

Figure 20:
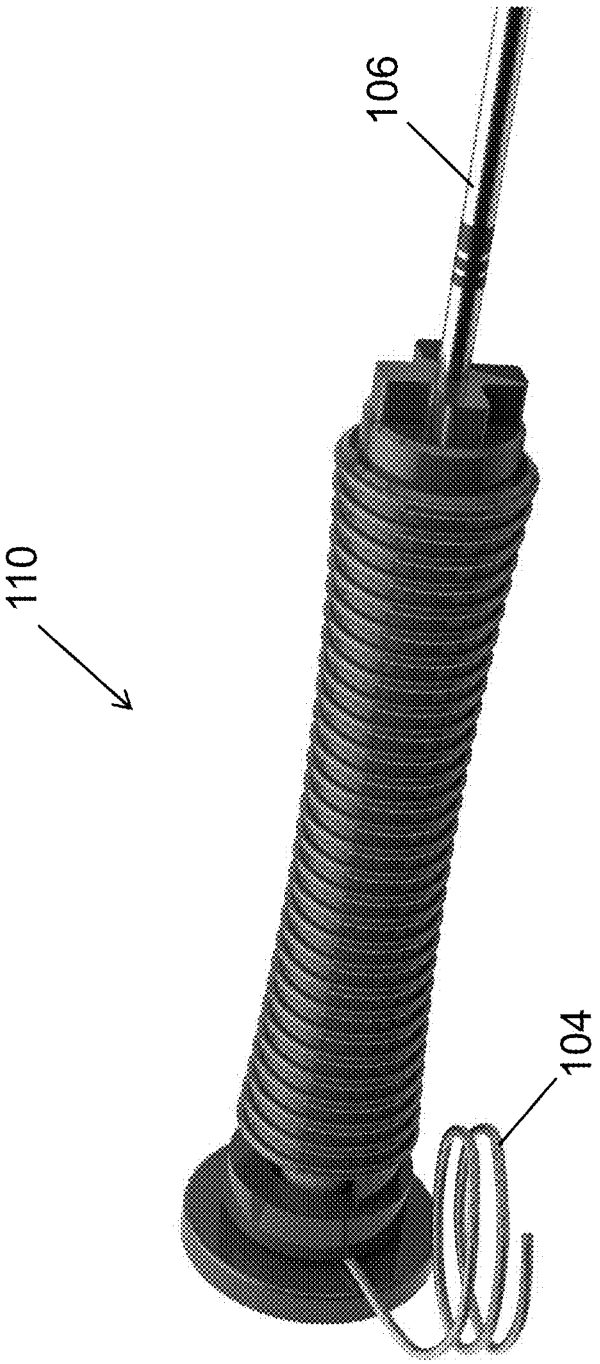
FIG. 20 is a perspective view of a handle assembly with a protruding portion of a thread coiling upon itself, according to an illustrative embodiment.

The thread 104 may generally be under stress as the thread extends through within the lumen of the stylet 108 and/or the lumen of the needle 106 prior to deployment. At least a portion of the thread 104 extending outwardly from the handle assembly 110 (e.g., from the handle body/plunger) may be unstressed so as to exhibit shape recovery characteristics and coil upon itself, as seen for example in FIG. 20. In such variations, the coiling of the thread 104 at the handle assembly 110 may advantageously assist in preventing the thread from extending into the clean or sterile field.

As will be further appreciated, as the hook assembly 105 is deployed at the target tissue and the handle assembly 110 is removed, the thread 104 may exhibit shape recovery characteristics and coil upon itself at the site where the thread extends external to the patient's body. In such variations, the coiling of the thread 104 upon itself (e.g., external the body) may aid in ensuring that the portion of the thread extending external to the patient may define a small footprint that is capable of being covered and/or contained with minimal disturbance to the patient or visual noticeability.

As previously mentioned, the coiling of the thread 104 when unstressed may advantageously cause the thread 104 to occupy a smaller area external to the patient than is possible with currently-available devices. In this way, the coiling of the thread 104 may allow for the coiled portion thread 104 external to the patient (e.g., against the skin of the patient) with a minimally small covering. In a variation, the covering may be a bandage or patch, including an adhesive bandage or adhesive patch. In a variation, the coiling of the thread 104 may provide for the coiled portion thread 104 external to the patient (e.g., against the skin of the patient) to occupy a footprint of no greater than 2 cm×2 cm. In a variation, the coiling of the thread 104 may provide for the coiled portion thread 104 external to the patient (e.g., against the skin of the patient) to occupy a footprint of no greater than 1.5 cm×1.5 cm. In a variation, the coiling of the thread 104 may provide for the coiled portion thread 104 external to the patient (e.g., against the skin of the patient) to occupy a footprint of no greater than 1.0 cm×1.0 cm. In a variation, the coiling of the thread 104 may provide for the coiled portion thread 104 external to the patient (e.g., against the skin of the patient) to occupy a footprint of no greater than a predetermined size defined by the clean or sterile field. As previously described, this may assist in providing minimal disturbance to the patient or visual noticeability and/or may advantageously assist in preventing the thread from extending into the clean or sterile field. In addition, this may also provide ease of use for application of a covering over the coiled portion of the thread 104. Moreover, this may provide infection reduction benefits and/or preventing the portion of the thread 104 external to the patient from extending into the clean or sterile field. Further yet, this may minimize or prevent the risk of the portion of the thread 104 external to the patient from being inadvertently and/or undesirably engaged or pulled, which may cause migration of the hook body 102 or other discomfort to the patient.

As may be appreciated, the coiling of the thread 104 may provide further advantages over the rigid wires typically employed in conventional devices. For example, rigid wires may protrude into a user's zone of vision, requiring the user to expend additional time and effort to managing the wire and prevent the wire from extending into the clean or sterile field and/or from being inadvertently or undesirably engaged or pulled. Additionally, with traditional rigid wires, the wire is susceptible from slipping from the user's grip, which can cause blood to sling into the user's eyes or face. Some users find it necessary to cut such rigid wires to make them more manageable. The coiling of the thread 104 as described herein may obviate one or more of these drawbacks associated with traditional rigid wires, such as by obviating the need to cut the thread and/or by providing for better management of the localization system as described herein.

In some variations, the thread 104 formed from a shape memory material having shape recovery characteristics as previously described may, individually or in any combination, be incorporated and/or combined with any of the other features discussed herein or illustrated in the accompanying drawings. For avoidance of doubt, it is to be understood that although a thread 104 configured to coil upon itself is only illustrated in FIG. 19 and FIG. 20, such a thread 104 could be incorporated into and/or combined with any variations of the tissue marking devices described herein or illustrated in the accompanying drawings.

The thread 104 may be located within the lumen of the stylet 108, the lumen of the needle 106, and/or through the handle body/plunger when the hook assembly 105 is loaded within the handle assembly 110 prior to deployment. The thread 104 may have a length of at least the length of the needle 106. In a variation, the thread 104 has a length so that it extends out of the second ends of the needle 106 and stylet 108 respectively. The thread 104 may have a length that is sufficient to extend through the breast and extend outside the body of the patient. In a variation, the thread 104 has a length of at least 5 cm. In a variation, the thread 104 has a length of at least 8 cm. In a variation, the thread 104 has a length of at least 10 cm. In a variation, the thread 104 has a length of at least 12 cm. In a variation, the thread 104 has a length of at least 14 cm. In a variation, the thread 104 has a length of at least 16 cm. In a variation, the thread 104 has a length of at least 20 cm. The thread 104 may have a diameter sufficient to fit through the lumen of the stylet 108 which is in the lumen of the needle 106. In a variation, the thread 104 may have a diameter of less than 1 mm. In a variation, the thread 104 may have a diameter of less than 0.5 mm. In a variation, the thread 104 may have a diameter of less than 0.25 mm.

Figure 21:
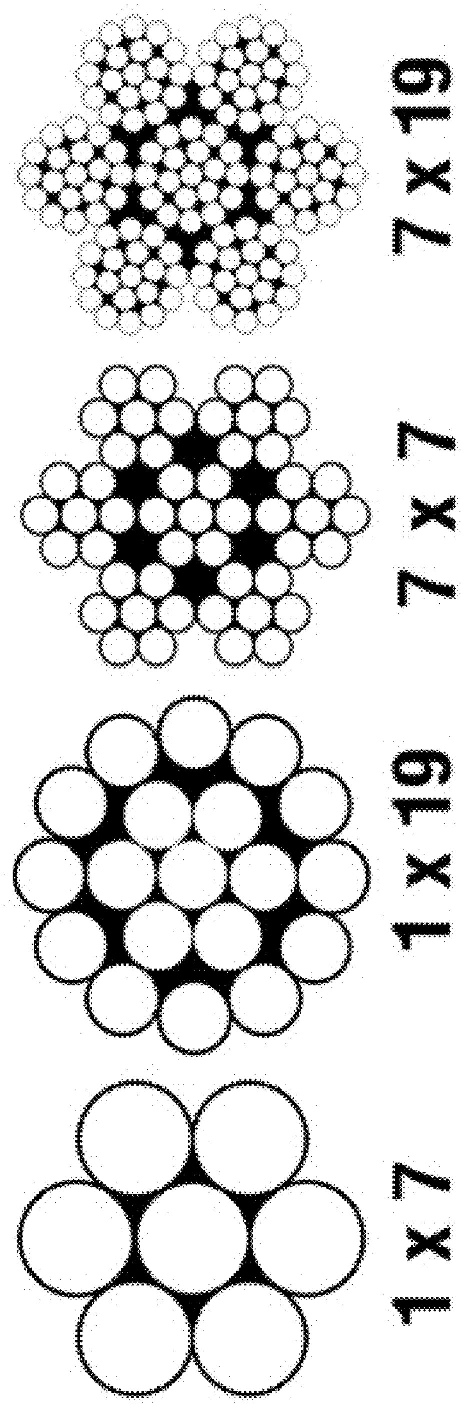
FIG. 21 is a diagram of different strand counts for the thread, according to an illustrative embodiment.

In a variation, the thread 104 may be constructed from single wires that are twisted into main strands, though other variations are not so limited. The thread 104 may have any desired wire construction to suit a particular application. By way of non-limiting example, as seen for example in FIG. 21, the thread 104 may have a 1×7 strand count, a 1×19 strand count, a 7×7 strand count, or a 7×19 strand count (i.e., number of strands by number of wires in each strand). Generally, the 1×7 strand count is the stiffest, while the 7×19 strand count is the most flexible. In combination with the sleeving 117 previously described, it has been found that the use of a thread 104 with a 7×7 strand count may provide desirable rigidity and flexibility properties for the thread. Moreover, it has been found that the use of a thread 104 with a 7×7 strand count may facilitate desired coiling of the thread when the thread is formed from a shape memory material having shape recovery characteristics.

Different variations of the hook assembly 105 may include different lengths of thread 104. For example, the tissue marking device 100 may be sized to the patient. In some variations, the excess thread 104 may be attached to the patient. For example, excess thread 104 may be wound and attached to the skin of the patient with an adhesive.

In a variation, the thread 104 may further include one or more radiopaque markers. In some variations, the radiopaque marker may be a band, a ball, or a knot in the thread 104. In some variations, the radiopaque marker may be at the point the thread 104 connects to the hook body 102. In other variations, the radiopaque marker may be at a point along the length of the thread 104. For example, a radiopaque marker may be located both at the hook body 102 and on the thread 104 about 0.5 to 2 cm away from the connection point to the hook body 102, depending on the length of the hook body in the compressed configuration.

In other variations, the thread 104 may include a series of marker bands 118 along a length of the thread, as seen for example in FIG. 3F. The marker bands may be raised from the thread such that a surgeon may be able to physically feel the marker bands. In addition, the marker bands may provide a surface to push against the hook body and/or other marker bands when the hook body is pushed out of the needle by the stylet. For example, the distal most marker band may push the hook body without any slack in between with the thread and the series of marker bands may be as close together as needed so they are all pushing on each other with no slack in the thread. In some variations, the marker bands 118 may be placed such that the distal most marker band is a set distance from the proximal end of the hook body 102 when in the compressed configuration. For example, the marker bands 118 may be placed such that the distal most marker band is about 0.5 mm, 1 mm, 2 mm, or 3 mm from the proximal end of the hook body 102 when in the compressed configuration. In other variations, the marker bands 118 may be placed on the thread 104 such that the distal most marker band is a set distance from where the thread connects to the hook body 102 (i.e. the center of the hook body). For example, the marker bands 118 may be placed on the thread 104 such that the distal most marker band is 0.5 cm to 2 cm from where the thread connects to the hook body 102 (i.e. the center of the hook body), depending on the length of the hook body in the compressed configuration. In at least one example, the marker bands 118 are placed on the thread 104 such that the distal most marker band is 1 cm from where the thread connects to the hook body 102.

In variations, the marker bands 118 may be employed in combination with the above-described sleeving 117. In one such variation, one or more of the marker bands 118 may be disposed within the sleeving 117. Put another way, the sleeving 117 may be disposed about the thread 104 such that the sleeving covers one or more of the marker bands 118. In such a variation, the marker bands 118 may advantageously be visible through the sleeving 117 during imaging. Put another way, in variations, the marker bands 118 may be radiopaque. In another variation, the sleeving 117 may be disposed between the marker bands 118 and the thread 104 and the marker bands 118 may be raised from the sleeving. Advantageously, this may provide visual acknowledgment to a user without the need for the above-described imaging. In a variation, the marker bands 118 may be disposed on the sleeving 117. By way of non-limiting example, in variations, the marker bands 118 may be painted or coated on to the sleeving 117. By way of further non-limiting example, the marker bands 118 may be radiopaque once painted, coated, or otherwise disposed on the sleeving 117.

In a variation, the thread may include 1 marker band. In a variation, the thread may include at least 2 marker bands. In a variation, the thread may include at least 3 marker bands. In a variation, the thread may include at least 4 marker bands. In a variation, the thread may include at least 5 marker bands. In a variation, the thread may include at least 6 marker bands. The marker bands 118 may be separated from each other by a set distance. For example, each marker band may be separated by 0.5 mm, 1 mm, 2 mm, or 3 mm. It will be appreciated that the radiopaque markers are configured to communicate a set distance to further facilitate the measurement of target tissue, to distinguish between multiple marked tissues, to demonstrate the distance of the hook from the targeted lesion, or to indicate a distance from the hook body to a biopsy marker clip. It will be appreciated that any arrangement of radiopaque markers is contemplated.

Figure 4A:
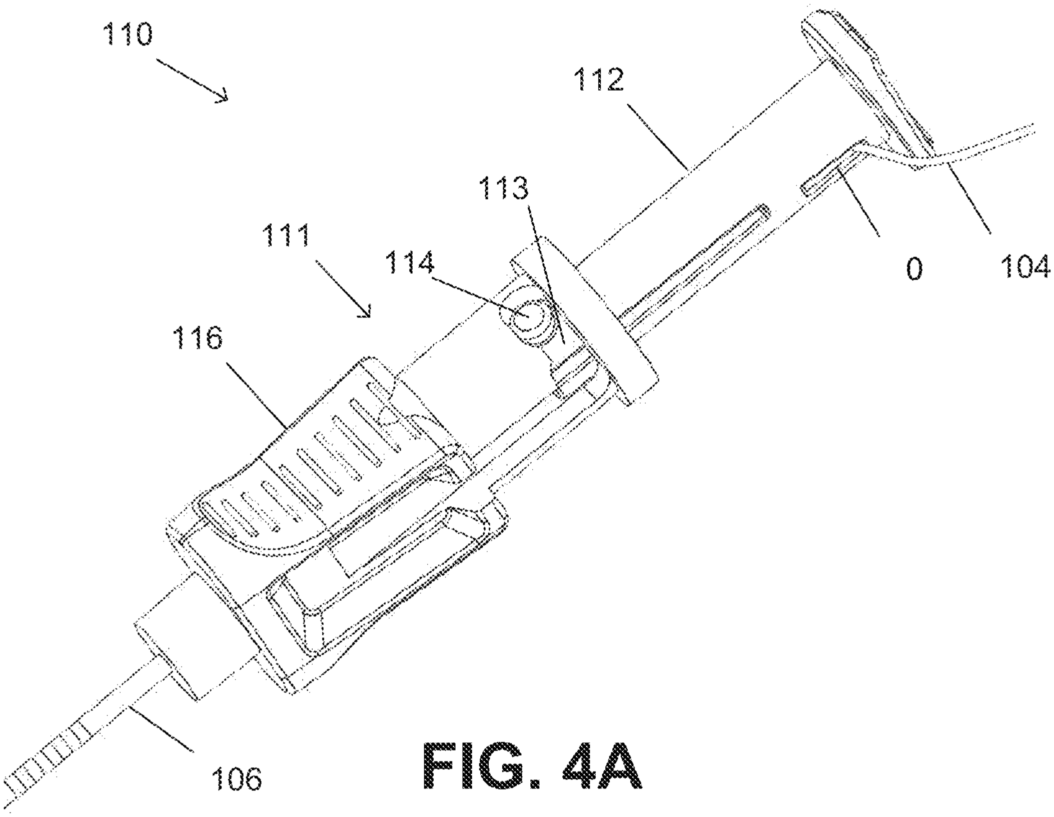
FIG. 4A is a side view of a handle assembly in the loaded position in one variation.
Figure 4B:
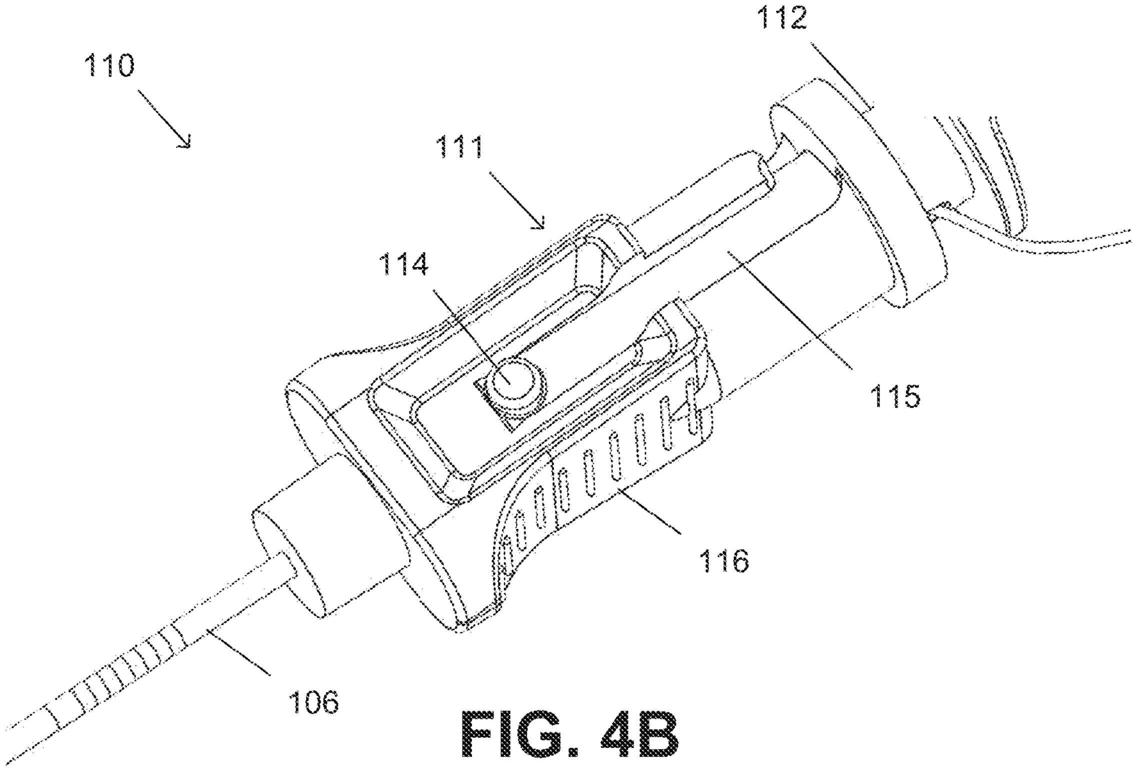
FIG. 4B is a side view of a handle assembly in the deployed position in one variation.
Figure 4C:
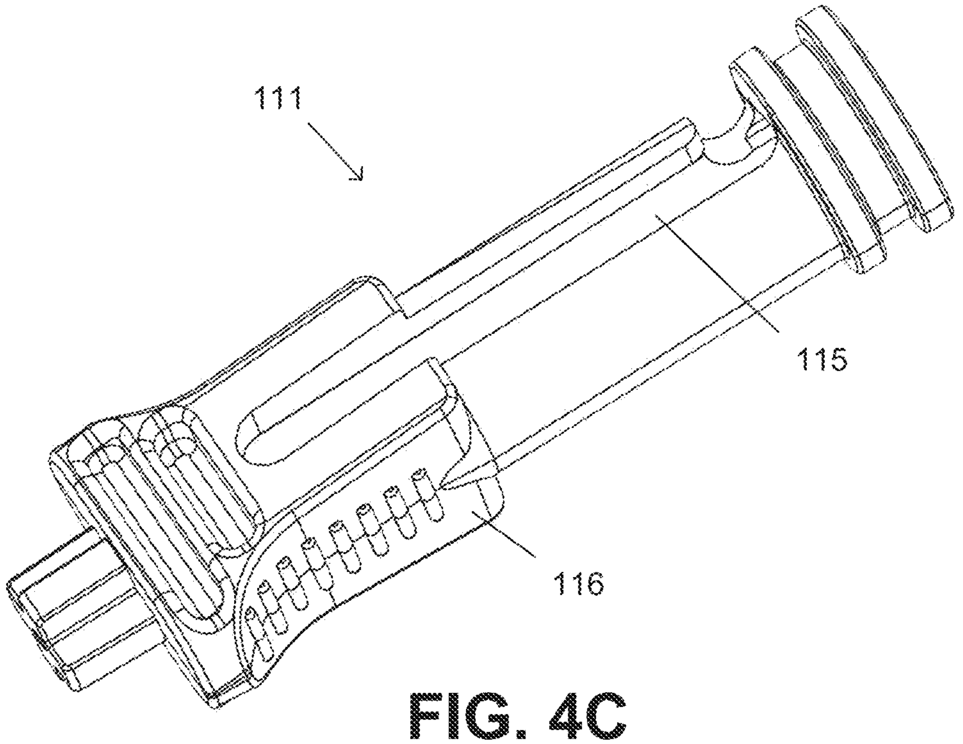
FIG. 4C is a side view of a handle body in one variation.

The tissue marking device 100 may further include a handle assembly 110. As seen in FIG. 1 and FIGS. 4A-4E, the handle assembly 110 includes a handle body 111, a plunger 112, a needle 106, and a stylet 108. As seen in FIGS. 4A-4C, the handle body 111 may include a grip 116 at the distal end of the handle body 111, a hollow longitudinal barrel, and a guide 115 extending longitudinally along a length of the handle body 111. The plunger 112 is operable to fit within the barrel of the handle body 111 and includes a locking mechanism 114 at its distal end operable to fit within the guide 115. The hook assembly 105 is initially contained within the needle 106 of the handle assembly 110 until it is deployed by the handle assembly 110 once near the target tissue. The handle assembly 110, by way of the needle 106, is configured to enter the breast and place the hook assembly 105 in the target tissue.

The needle 106 has a lumen that is open on a first end and a second end. In a variation, the needle 106 is a 16 gauge needle. In a variation, the needle 106 is a 17 gauge needle. In a variation, the needle 106 is an 18 gauge needle. In a variation, the needle 106 is a 19 gauge needle. In a variation, the needle 106 is a 20 gauge needle. In a variation, the needle 106 is at least 5 cm long. In a variation, the needle 106 is at least 7 cm long. In a variation, the needle 106 is at least 8 cm long. In a variation, the needle 106 is at least 10 cm long. In a variation, the needle 106 is at least 12 cm long. In a variation, the needle 106 is at least 14 cm long. In a variation, the needle 106 is at least 16 cm long. In a variation, the needle 106 is at least 20 cm long. In a variation, the needle 106 is less than 20 cm long. The needle 106 is attached to the distal end of the handle body 111. The needle 106 may be reversibly or irreversibly attached to the distal end of the handle body 111.

The stylet 108 may be a tube that is open on a first end and second end. The stylet 108 is configured to sit within the needle 106 and hold the thread 104 within its lumen. The first end of the stylet 108 may extend into the handle body 111 and the second end of the stylet 108 may rest on or near the proximal end of the hook body 102. FIGS. 2A and 2B show the second end of the stylet 108 surrounding the thread 104 and near the proximal end of the hook body 102. In a variation, the first end of the stylet 108 is connected to the distal end of the plunger 112.

The stylet 108 may have a diameter sufficient to fit within the lumen of the needle 106 while being the same diameter or smaller than the diameter of the hook body 102. This allows for the stylet 108 to push on the proximal end of the hook body 102 to push the hook body 102 out of the needle and into the target tissue. In a variation, the stylet 108 may have an outer diameter less than the diameter of the lumen of the needle 106. In a variation, the stylet 108 may have an outer diameter of less than 1.5 mm. In a variation, the stylet 108 may have an outer diameter of less than 1 mm. In a variation, the stylet 108 may have an outer diameter of less than 0.75 mm. In a variation, the stylet 108 may have an outer diameter of less than 0.5 mm. In a variation, the stylet 108 may have an outer diameter of at least 0.5 mm. In a variation, lumen of the stylet 108 may have a diameter of at least 0.25 mm. In a variation, lumen of the stylet 108 may have a diameter of less than 0.5 mm. In a variation, lumen of the stylet 108 may have a diameter of less than 0.75 mm. In a variation, lumen of the stylet 108 may have a diameter of less than 1 mm.

The stylet 108 may have a length that is at least the length of the needle 106. In a variation, the stylet 108 is longer than the needle 106. In a variation, the stylet 108 is at least 5 cm long. In a variation, the stylet 108 is at least 7 cm long. In a variation, the stylet 108 is at least 8 cm long. In a variation, the stylet 108 is at least 10 cm long. In a variation, the stylet 108 is at least 12 cm long. In a variation, the stylet 108 is at least 14 cm long. In a variation, the stylet 108 is at least 16 cm long. In a variation, the stylet 108 is at least 20 cm long. In a variation, the stylet 108 is less than 20 cm long.

The handle body is designed to minimize size and weight of the device. It has an ergonomic grip and the hook assembly can be deployed with a simple turn of the handle. As seen in FIG. 4C, the handle body 111 includes a grip 116 at the distal end of the handle body 111, a hollow longitudinal barrel, and a guide 115 extending longitudinally along a length of the handle body 111. The handle body may be made of molded plastic in one variation.

Figure 4D:
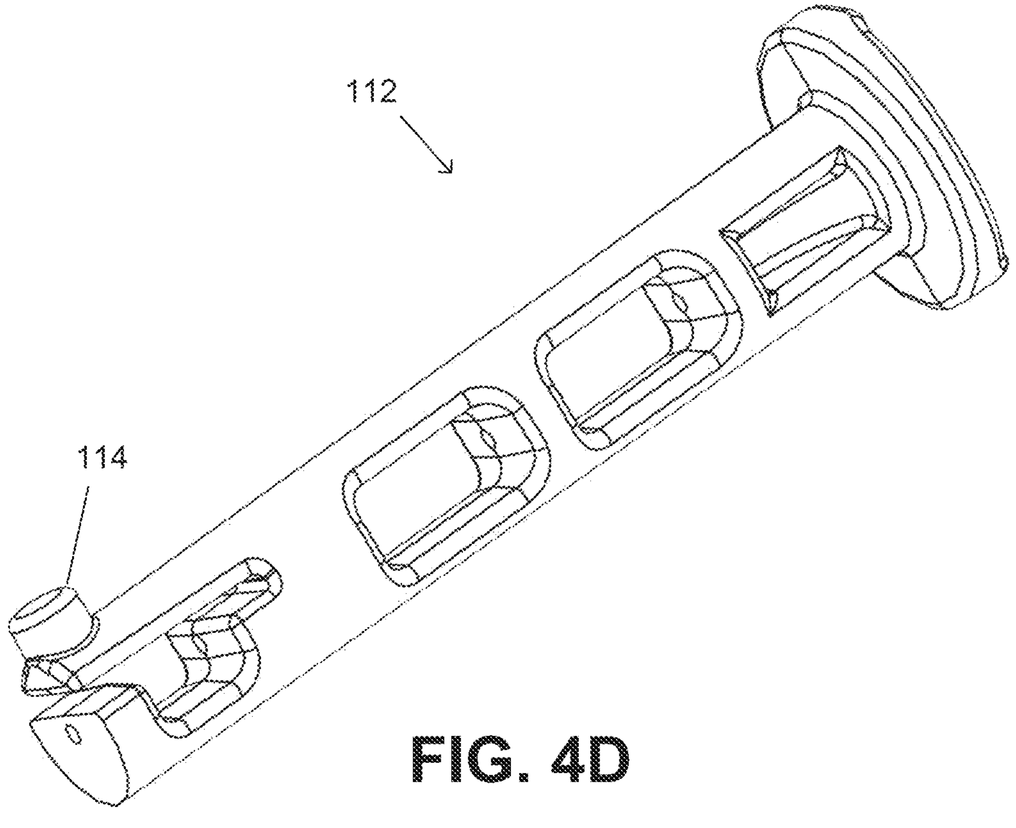
FIG. 4D is a side view of a plunger in one variation.
Figure 4E:
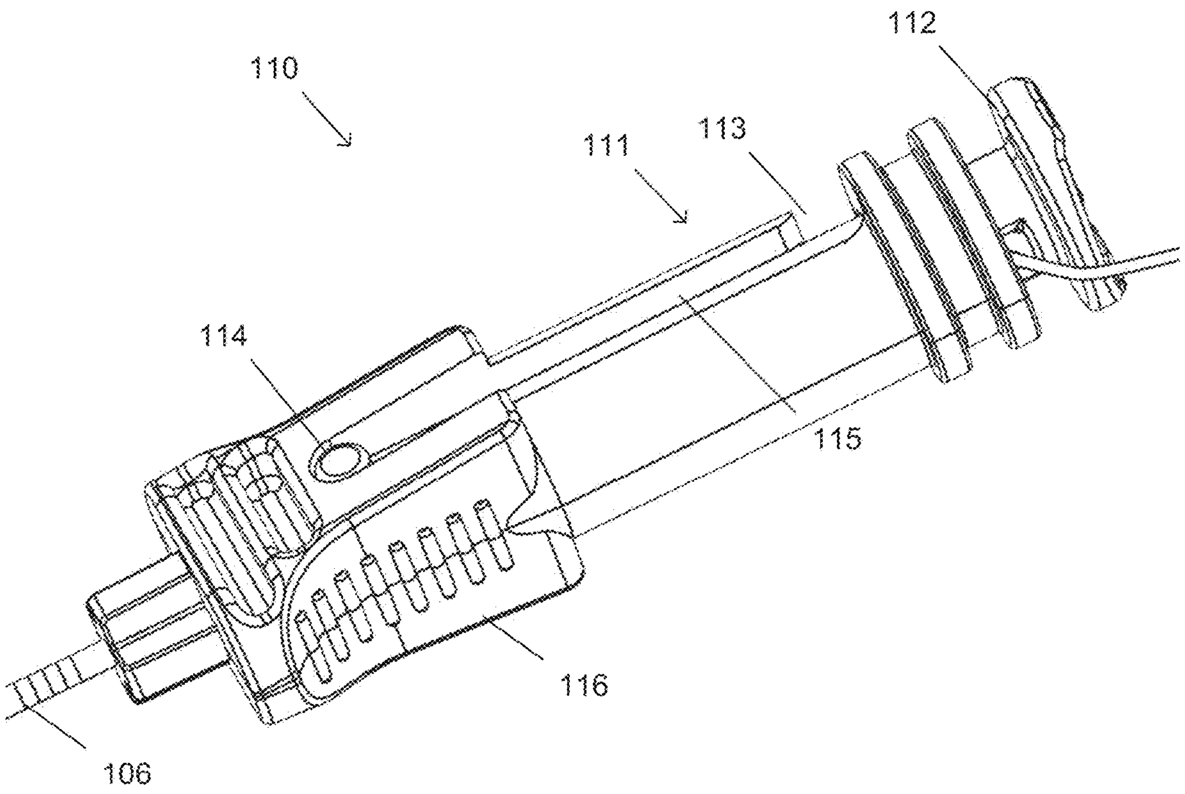
FIG. 4E is a side view of a handle assembly in the deployed position in one variation.

As seen in FIG. 4D, the plunger 112 includes a locking mechanism 114 at its distal end operable to fit within the guide 115 of the handle body 111. As seen in FIG. 4E, the plunger 112 is sized to fit inside the barrel of the handle body 111. The plunger 112 extends the length of the handle body 111, protrudes out the proximal end of the handle body 111, and connects to the stylet 108 at its distal end within the handle body 111. The plunger 112 is configured to actuate between two distinct positions, an extended position and a depressed position. FIG. 4A shows the plunger 112 in the extended position when the handle assembly 110 is loaded with the hook assembly 105. In particular, FIG. 4A shows the thread 104 loaded through the handle body 111 and plunger 112. When the plunger 112 is in the extended position, the hook body 102 remains in the needle 106 and the thread remains in the stylet 108, needle 106, and hook body 111/plunger 112. FIG. 4B shows the plunger 112 in the depressed position when the hook assembly 105 has been deployed. When the plunger 112 is pushed from the extended position to the depressed position, the hook body 102 is pushed by the stylet 108 the distance the plunger 112 is pressed, and therefore, the hook body 102 extends past the second end of the needle 106 by the same distance. Therefore, when placing the needle 106 in the target tissue, it is known what distance the hook body 102 will be pushed past the second end of the needle 106 when the plunger 112 is depressed and the hook body 102 is deployed.

The handle body 111 may further include an opening for receiving a proximal end of the thread. In one variation, the plunger may further include an opening 120, as seen in FIG. 4A, that receives the excess end of the thread 104. In other variations, the opening 120 may be located on any portion of the handle body 111 and/or the plunger 112.

The handle body 111 or the plunger 112 may further include a locking mechanism 114. In a variation, the locking mechanism 114 is near the distal end of the plunger 112. The locking mechanism 114 may be a protrusion that fits within the guide 115 extending at least a portion of the length of the handle body 111. The locking mechanism 114 may be in a locked or unlocked position. When in the locked position, the locking mechanism 114 may be located within a recession 113 on the handle body 111 perpendicular to the guide 115 at the proximal end of the guide 115. To move the locking mechanism 114 to the unlocked position, the locking mechanism 114 is moved or rotated to be outside of the recession 113 to be within the guide 115. Because the locking mechanism is on the plunger, the plunger is moved or rotated such that the locking mechanism is outside the recession and within the guide to unlock the handle. In some variations, the recession has a length at least half the circumference of the handle body such that the plunger has to rotate at least 180° to unlock. The locking mechanism 114 may be connected to the plunger 112 such that the locking mechanism 114 prevents the actuation of the plunger 112 when the locking mechanism 114 is in the locked position. FIG. 4A shows the locking mechanism in a locked position. FIG. 4B shows the locking mechanism in an unlocked position. The length of the guide 115 may be compatible with the length of the plunger 112 and the desired distance that the plunger may be pushed to deploy the hook assembly 105.

The locking mechanism 114 prevents the hook assembly 105 from being accidentally deployed during assembly, shipment, and insertion of the needle. Because the tissue marking device 100 is a single use, non-removable device, the locking mechanism 114 is necessary to prevent accidental deployment until it is confirmed that the hook assembly will be deployed in the desired location of the target tissue.

In a variation, the handle body 111 may further include a grip 116. In a variation, the grip 116 may be a two finger grip for easy manipulation by the physician, as seen in FIGS. 4A-4C. Further, the handle body 111 may be lightweight, such that the weight of the handle body attached to the needle 106 does not affect the movement or placement of the hook assembly 105.

In use, the hook assembly 105 is seated in the second end of the needle 106 and stylet 108 such that the hooks 101 and retention mechanism 107 are in the compressed configuration. The handle assembly 110, by way of the needle 106, is forced in the breast until the second end of the needle 106 reaches the target tissue. The locking mechanism 114 is rotated from the recession 113 into the guide 115 to be in the unlocked position. The plunger 112 is pressed by the thumb or another finger of the user. The first end of the stylet 108 is then pressed by the plunger 112 causing the hook body 102 to extend past the second end of the needle 106, open/deploy the hooks 101, and embed in the target tissue. The needle 106 and stylet 108 are removed from the tissue using the handle body 111, leaving the thread 104 protruding from the skin and attached to the hook body 102.

Figure 5:
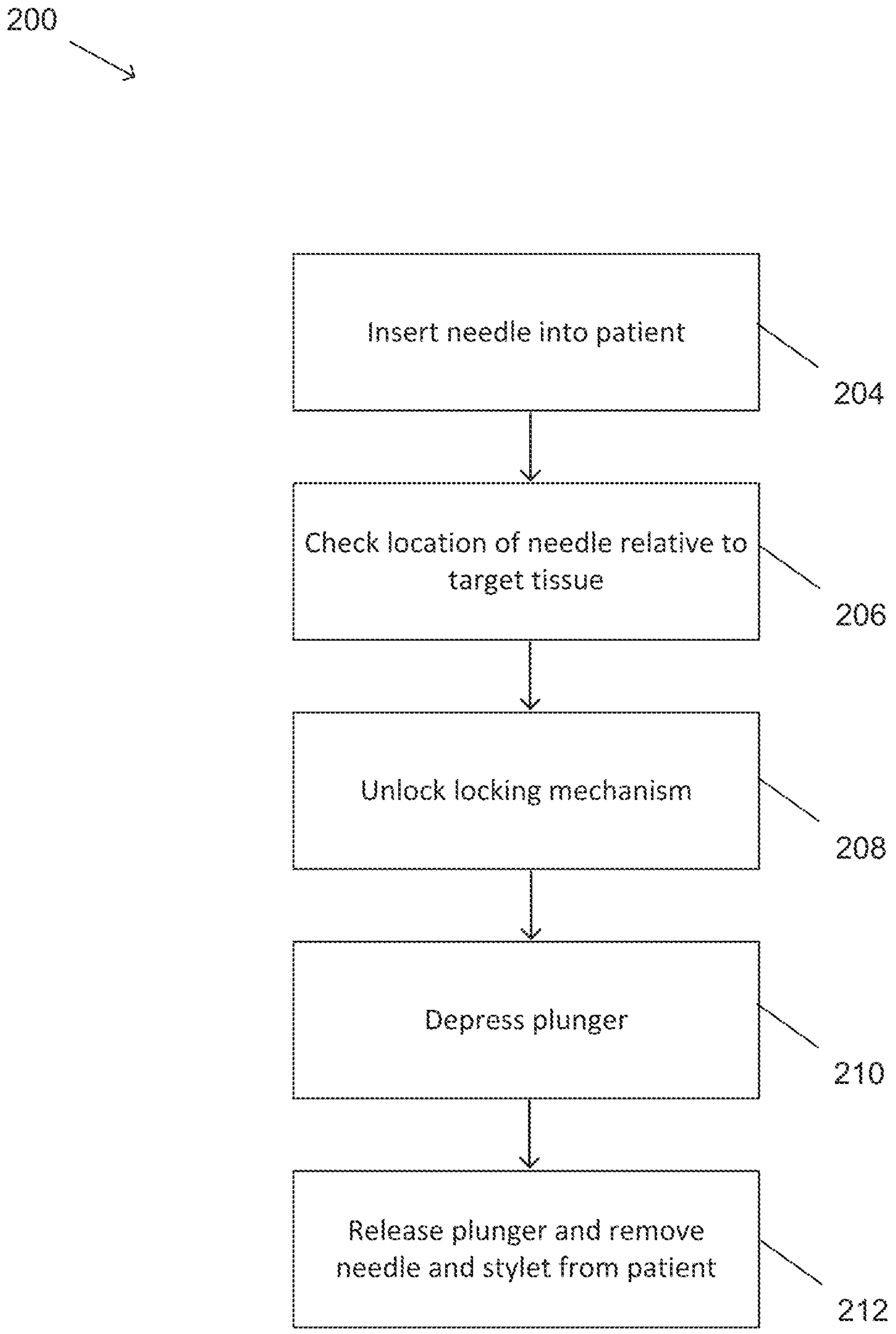
FIG. 5 is a diagram of a method of using of the tissue marking device in one variation.

A description of a method for marking tissue for removal using a tissue marking device, as illustrated in FIG. 5, is disclosed herein. The method shown in FIG. 5 is provided by way of example, as there are a variety of ways to carry out the method. Additionally, while the example methods are illustrated with a particular order of blocks, those of ordinary skill in the art will appreciate that FIG. 5 and the blocks shown therein can be executed in any order that accomplishes the technical advantages of the present disclosure and can include fewer or more blocks than illustrated. Each block shown in FIG. 5 represents one or more processes, methods or subroutines, carried out in the example method.

Referring now to FIG. 5, the method of using the tissue marking device 100 is depicted in one variation. Method 200 includes inserting the needle with the compressed hook assembly in a patient so that the hook body is near a target tissue at steps 204 and 206, unlocking the locking mechanism at step 208, depressing the plunger to extend the hook body past the needle and embed in the target tissue at step 210, and removing the needle and stylet from the patient at step 212. In a variation, the method 200 may further include leaving the thread exposed on the surface of the skin. The exposed thread may then be secured to the skin. In some variations, the method may further include loading the hook assembly in the handle assembly prior to inserting the needle into the patient. Loading the hook assemble in the handle assembly may include loading/inserting the hook body into the needle and loading/inserting the thread through the stylet, needle, and plunger within the handle body. The hooks and retention mechanism of the hook body may need to be physically compressed to be loaded within the needle.

The use of the tissue marking device allows for the safe separation of treatment days. The separation of treatment days provides time for the hook assembly to be properly placed and then patient can return on a different day for surgery instead of being rushed to surgery on the same day and being severely restricted on movement for fear of the marker migrating. In addition, the separation of treatment days overcomes the inefficiencies created trying to coordinate radiology, surgery, operating room, and patient physical location when the localization and surgery are on the same day.

Figure 6:
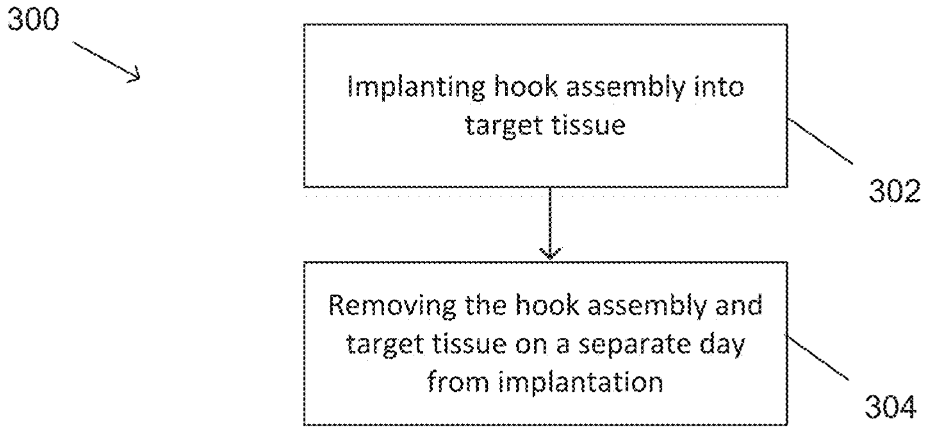
FIG. 6 is a diagram of a method of using of marking a target tissue in one variation.

In another variation, FIG. 6 provides a method for marking tissue for removal using a tissue marking device. The method shown in FIG. 6 is provided by way of example, as there are a variety of ways to carry out the method. Additionally, while the example methods are illustrated with a particular order of blocks, those of ordinary skill in the art will appreciate that FIG. 6 and the blocks shown therein can be executed in any order that accomplishes the technical advantages of the present disclosure and can include fewer or more blocks than illustrated. Each block shown in FIG. 6 represents one or more processes, methods or subroutines, carried out in the example method.

Referring now to FIG. 6, the method of implanting and removing the hook assembly 105 of the tissue marking device 100 is depicted in one variation. Method 300 includes implanting the hook assembly of the tissue marking device into a target tissue of a patient at step 302 and removing the hook assembly and target tissue on a separate day from implantation at step 304. In a variation, the hook assembly is operable to absorb compression forces without migrating within the target tissue such that re-localization/re-implantation would be required. In a variation, the hook assembly is operable to allow the patient to have surgery to remove the hook assembly on a separate day from localization/implantation. The ability to absorb compression forces may permit the patient to participate in normal activity between the time of localization/implantation of the hook assembly and the time of surgery to remove the target tissue. Non-limiting examples of normal activity include sleeping (face down if desired), sexual activity, taking care of loved ones (for example, kids), exercising, and/or lifting heaving objects.

Unlike conventional wire marker devices, the hook assembly can be embedded in a target tissue and still allow a patient to perform most normal activities. This allows the hook assembly to be placed far in advance of the surgery. The structure of the hook body with hooks and retention mechanism may allow for the hook assembly to flex with the patient's movements and thus not migrate within the target tissue. In a variation, the hook body may only migrate up to 15 mm from its original placement location. In a variation, the hook body may only migrate up to 10 mm from its original placement location. In a variation, the hook body may only migrate up to 8 mm from its original placement location. In a variation, the hook body may only migrate up to 6 mm from its original placement location. In a variation, the hook body may only migrate up to 5 mm from its original placement location. In a variation, the hook body may only migrate up to 4 mm from its original placement location. In a variation, the hook body may only migrate up to 2 mm from its original placement location. In a variation, the hook body may only migrate up to 1 mm from its original placement location. In a variation, the hook body may only migrate up to 0.5 mm from its original placement location. In addition, the thread may further allow for the patient's movements to not affect the hook body placement. The flexible thread may impart less tension on the hook body as compared to a standard wire such that it flexes instead of pulling on the hook body. In some variations, the hook assembly may have a pull force of greater than 380 g.

In some variations, the method may further include surgically removing the hook assembly and target tissue on a separate day from when the hook assembly was implanted. In a variation, the hook assembly may be placed up to 24 hours before surgery. In a variation, the hook assembly may be placed more than 24 hours before surgery. In a variation, the hook assembly may be placed up to 2 days before surgery. In a variation, the hook assembly may be placed up to 5 days before surgery. In a variation, the hook assembly may be placed up to 8 days before surgery. In a variation, the hook assembly may be placed up to 10 days before surgery. In a variation, the hook assembly may be placed up to 12 days before surgery. In a variation, the hook assembly may be removed at least 24 hours after implantation. In a variation, the hook assembly may be removed up to 2 days after implantation. In a variation, the hook assembly may be removed up to 5 days after implantation. In a variation, the hook assembly may be removed up to 8 days after implantation. In a variation, the hook assembly may be removed up to 10 days after implantation. In a variation, the hook assembly may be removed up to 12 days after implantation.

A tissue marking device comprising: a hook assembly having a compressed configuration and a deployed configuration, the hook assembly comprising: a hook body comprising at least two hooks; and a thread connected to the hook body; and a handle assembly for positioning the hook assembly in a targeted tissue comprising: a handle body having a proximal end and a distal end; a needle having a lumen with an open first end and a second end; and a stylet having a lumen with an open first end and a second end, wherein the hook body and the stylet are within the lumen of the needle and the thread is within the lumen of the stylet when the hook assembly is in the compressed configuration.

A tissue marking device comprising: a hook body having a proximal end and a distal end, the hook body comprising at least two hooks, wherein the hook body has a compressed configuration and a deployed configuration.

A tissue marking device comprising: a hook body comprising at least two hooks; a metal thread crimped or welded to the proximal end of the hook body.

A tissue marking device comprising: a handle assembly comprising: a handle body having a proximal end and a distal end; a needle having a lumen with an open first end and a second end, the needle lumen configured to contain a hook body in a compressed configuration; and a stylet having a lumen with an open first end and a second end, the stylet configured to be within the lumen of the needle and the stylet lumen configured to contain a thread connected to the hook body.

The handle body comprises a plunger and a locking mechanism. The first end of the stylet is connected to the plunger such that pressing the plunger extends the hook body into the target tissue. The handle body further comprises a recession and guide for positioning the locking mechanism in a locked and unlocked position, respectively. The hook body comprises two hooks. The hook body comprises three hooks. The tissue hook body comprises at least two hooks separated by 180°, 120°, 90°, 45°, or a combination thereof. The hook body comprises at least two hooks having a straight configuration or curved configuration. The hook body comprises a laser cut nitinol tube. The thread is selected from a chromium cobalt, stainless steel, nitinol, or Kevlar thread. The thread is crimped or welded to a proximal end of the hook body. The hook body has at least one radiopaque marker. The thread has at least one radiopaque marker. The first end of the needle is connected to the distal end of the handle body.

A method of marking a target tissue in a patient comprising: inserting a tissue marking device into a patient, the tissue marking device comprising: a hook assembly comprising a hook body with at least two hooks and a thread; and a handle assembly comprising a stylet, a needle, and a handle body comprising a locking mechanism and a plunger; confirming the location of the needle such that the hook body is near the target tissue; unlocking the locking mechanism on the handle body; depressing the plunger to extend the hook body past the needle and open the at least two hooks to embed the hook body in the target tissue; and removing the needle and the stylet from the patient.

The method further comprises loading the hook assembly into the handle assembly. The method further comprises securing the thread to the patient's skin. The method further comprises having the patient return at least 24 hours later for surgery. The patient returns up to 12 days later for surgery. The hook assembly has a compressed configuration and a deployed configuration. The hook body and the stylet are within the lumen of the needle and the thread is within the lumen of the stylet when the hook assembly is in the compressed configuration. The handle body further comprises a recession and guide for positioning the locking mechanism in a locked and unlocked position, respectively.

The hook body comprises two hooks. The hook body comprises three hooks. The hook body comprises at least two hooks separated by 180°, 120°, 90°, 45°, or a combination thereof. The hook body comprises at least two hooks having a straight configuration or curved configuration. The hook body comprises a laser cut nitinol tube. The thread is selected from a chromium cobalt, stainless steel, nitinol, or Kevlar thread. The thread is crimped or welded to a proximal end of the hook body. The hook body has at least one radiopaque marker. The thread has at least one radiopaque marker. The target tissue is within the patient's breast.

FIGS. 7A-12C illustrate an example of a tissue marking device 100 and its corresponding components. The tissue marking device 100 and corresponding components illustrated in FIGS. 7A-12C may have the same reference designations as in FIGS. 1A-4D above. It will be appreciated that for simplicity and clarity of illustration, where appropriate, reference numerals have been repeated among the different figures to indicate corresponding or analogous elements and/or functions.

Figure 7A:
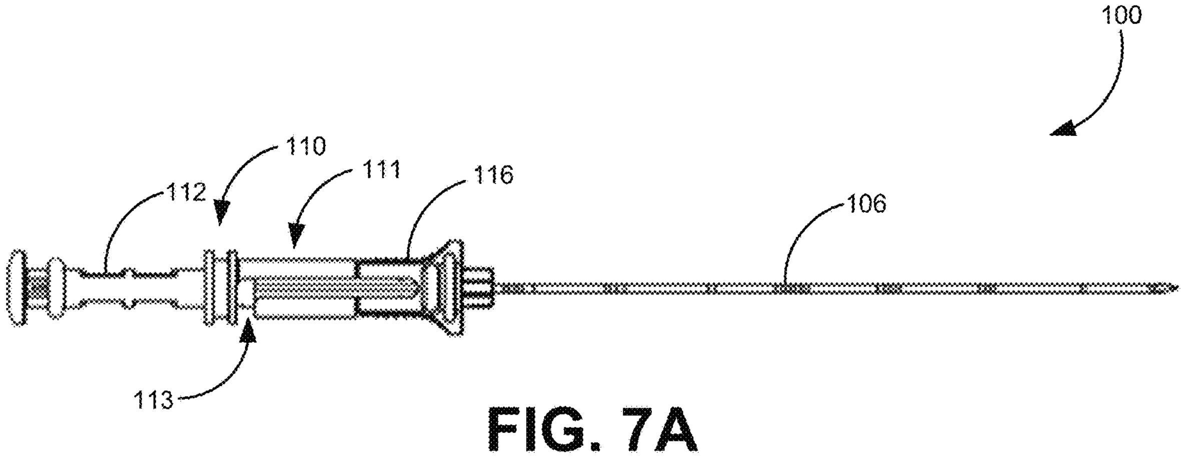
FIG. 7A is a diagram of a tissue marking device in a locked position.
Figure 7B:
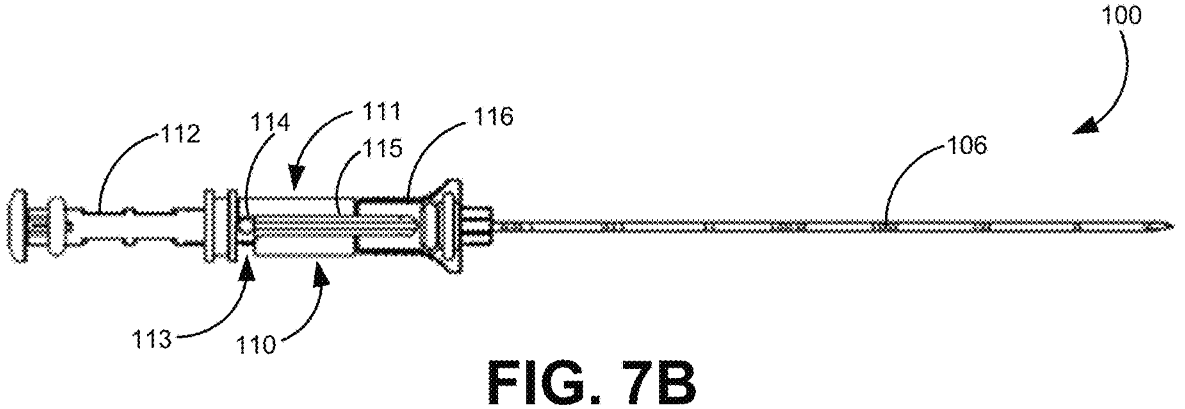
FIG. 7B is a diagram of a tissue marking device in a locked position.

FIG. 7A illustrates the tissue marking device 100 in a locked position, similar to FIG. 4B, and FIG. 7B illustrates the tissue marking device 100 in an unlocked position, similar to FIG. 4A. As illustrated in FIG. 7A, the locking mechanism 114 is not visible from the presented view as the locking mechanism 114 is moved or rotated to be outside of the recession 113. Accordingly, the locking mechanism 114, in the locked position as illustrated in FIG. 7A, prevents the actuation of the plunger 112. As illustrated in FIG. 7B, the locking mechanism 114 is moved or rotated to be inside the recession 113 such that the locking mechanism 114 can translate along the guide 115 when the plunger 112 is depressed or actuated. Accordingly, as illustrated in FIG. 7B, the tissue marking device 100 is in an unlocked position, and the plunger 112 can be actuated to at least partially release the hook assembly 105.

Figure 8A:
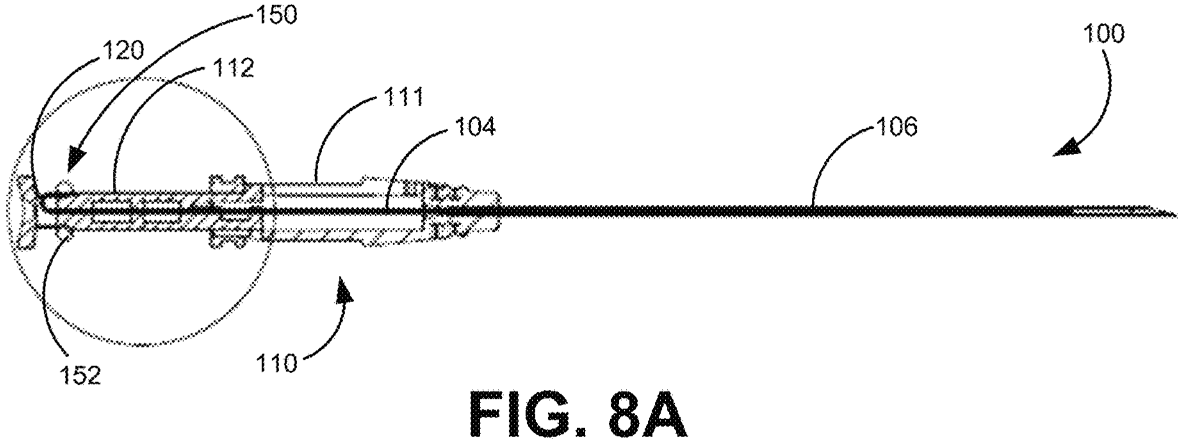
FIG. 8A is a cross-sectional view of a tissue marking device.
Figure 8B:
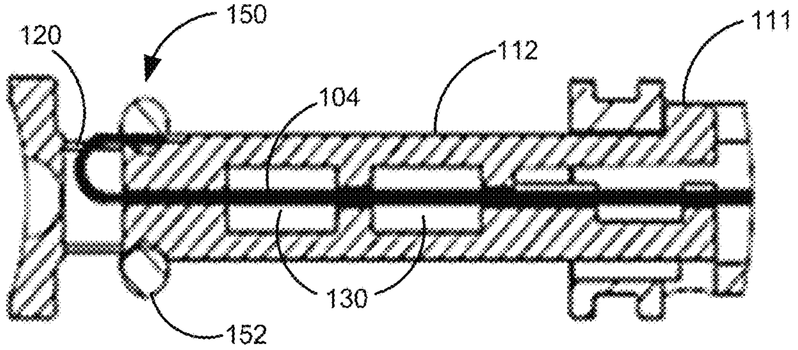
FIG. 8B is a cross-sectional view of a handle assembly with a release mechanism.
Figure 8C:
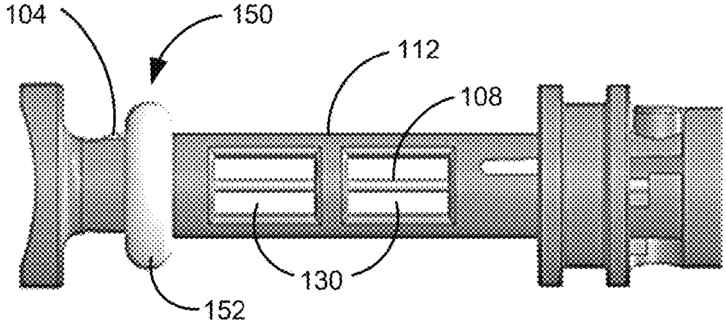
FIG. 8C is a diagram of a handle assembly with a release mechanism.

FIGS. 8A-8E illustrate the handle assembly 110 of the tissue marking device 100 with a release mechanism 150. The release mechanism 150 is operable to control the release of the hook assembly 105. In at least one example, as illustrated in FIGS. 8A-8C, the release mechanism 150 can include a release ring 152. In at least one example, the release ring 152 can include an o-ring. In some examples, the release ring 152 can have a shape of a horseshoe, a clip, or any other suitable shape such that the release ring 152 can be disposed on and/or around the plunger 112 and movable along the plunger 112 upon application of enough force by the user. The release ring 152 can be operable to hold the thread 104 such that the thread 104, when the release mechanism 150 and the release ring 152 are in a hold position as shown in FIGS. 8A-8B, can be retracted along with retraction of the plunger 112. The thread 104 can pass through the handle assembly 110 and the plunger 112 and through the opening 120 in the handle body 111.

In all variations and embodiments provided herein the thread can be chromium cobalt, stainless steel, nitinol, and Kevlar. In some variations, the thread can be chromium cobalt. In some variations, the thread can be stainless steel. In some variations, the thread can be nitinol. In some variations, the thread can be Kevlar. In some variations, the thread can be a wire. In some variations, the thread can be a single unit or a braid, such as a braided cable, or high-tensile strength braided suture used in such applications as orthopedic surgery.

In at least one example, as illustrated in FIGS. 8A-8E, the handle body 111 can form one or more holes 130. In some examples, the holes 130 can be formed in the plunger 112. In some examples, as shown in FIG. 8C, the stylet 108 can be visible through the holes 130, while the thread 104 can be disposed within the stylet 108. The holes 130 can be included to lessen the weight of the handle 112, and correspondingly the tissue marking device 100. In at least one example, by lessening the weight of the tissue marking device 100, the tissue marking device 100 can be easier to handle by the user. In some examples, lessening the weight of the tissue marking device 100 at the handle assembly 110 can minimize the moment acting about the tip of the needle 106 such that unintended motion of the needle 160 during placement of the hook assembly 105 is minimized.

Figure 8D:
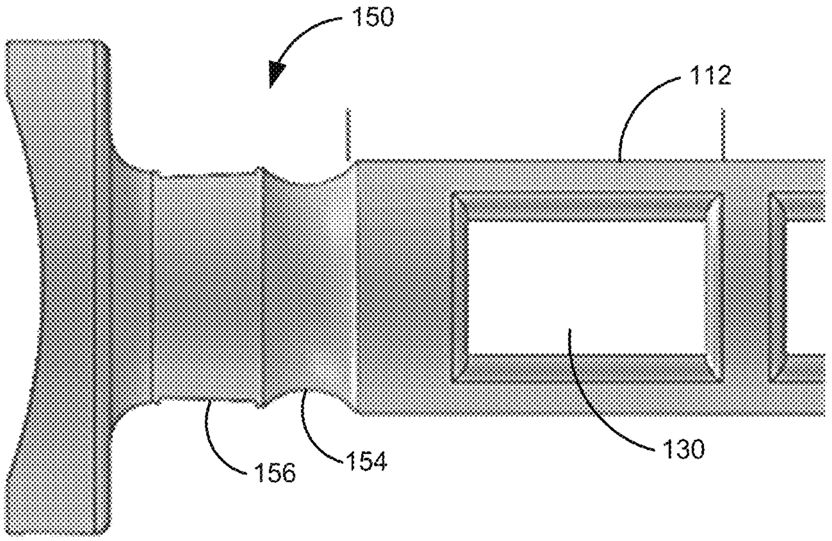
FIG. 8D is a diagram of a handle assembly with a release mechanism omitting a release ring.
Figure 8E:
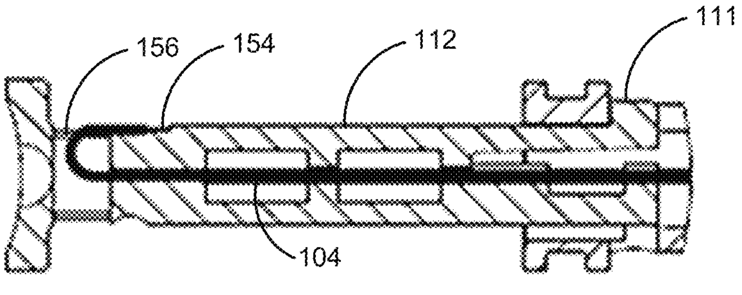
FIG. 8E is a cross-sectional view of a handle assembly with a release mechanism omitting a release ring.

FIGS. 8D and 8E illustrate the handle body 111 and the release mechanism 150, omitting the release ring 152. The release mechanism 152 includes a groove 154 operable to receive the release ring 152. Additionally, in some examples, the groove 154 can receive the proximal end of the thread 104. The thread 104 can be held in place within the groove 154 by the release ring 152 being disposed within the groove 152.

In some examples, the release mechanism 150 can also include a release portion 156 which is operable to receive the release ring 152 when the release ring 152 is driven out of the groove 154. For example, the release ring 152 can be driven out of the groove 154 when the release ring 152 abuts the handle body 111 and the plunger 112 is pushed with enough force that the release ring 152 is driven out of the groove 154 and onto or into the release portion 156. When the release ring 152 is driven onto and/or into the release portion 156, the thread 104 is released out of the groove 154 and is freely accessible.

Figure 9A:
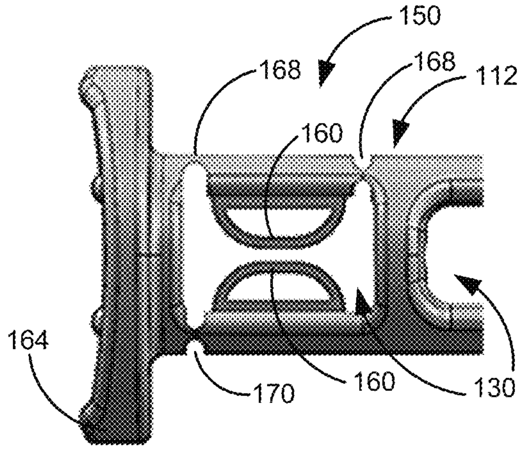
FIGS. 9A-9C are diagrams of a handle assembly with a release mechanism.
Figure 9B:
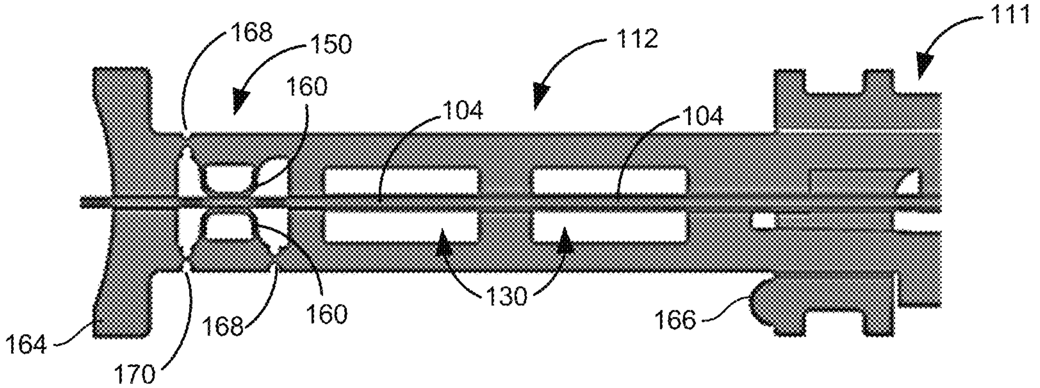
Figure 9C:
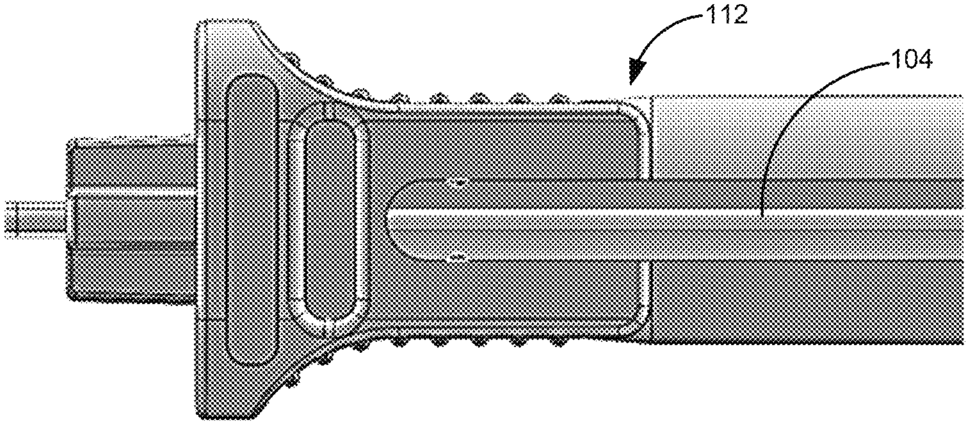

FIGS. 9A-9C illustrate different examples of handle assemblies 110. FIGS. 9A and 9B illustrate examples of plungers 112, and FIG. 9C illustrates a partial cross-sectional view of an example of a plunger 112. As illustrated in FIGS. 9A and 9B, the release mechanism 150 can include retention structures 160 which are operable to provide an interference fit on the thread 104 to secure the thread 104 to the plunger 112. Accordingly, when the retention structures 160 abut against the thread 104, the plunger 112 can be retracted, and the thread 104 along with the hook assembly 105 is pulled along with the plunger 112. As illustrated in FIGS. 9A and 9B, the retention mechanisms 160 can form a D shape. In other examples, the retention mechanisms 160 can be formed in any other suitable shape so long as the retention mechanisms 160 can provide an interference fit on the thread 104. When the plunger 112 is advanced to the partial release position (for example as shown below in FIG. 10B), the interference surface 164 on the plunger 112 abuts the interference surface 166 on the handle body 111. To proceed to the full release position (for example as shown below in FIG. 10C), additional force is applied to the plunger 112 such that the break point member 170 is broken. The break point member 170 can include, for example, a narrowed portion of the plunger 112. When the break point member 170 is broken, the retention mechanisms 160 pivot at the flexure points 168, thereby releasing the thread 104.

Figure 10A:
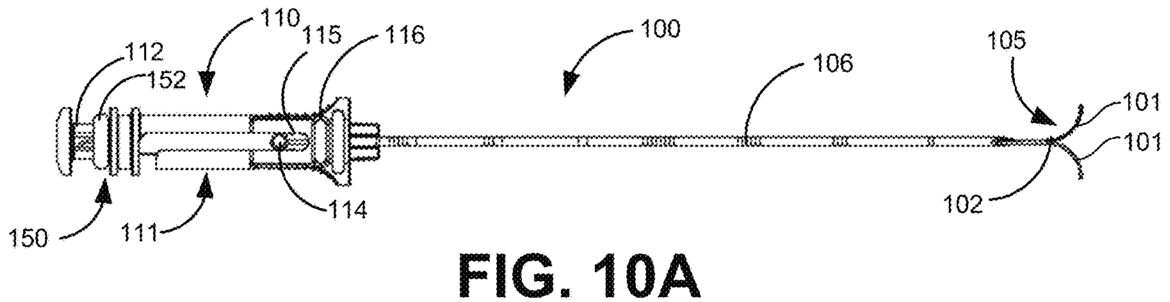
FIG. 10A is a diagram of a tissue marking device in a partial release position.
Figure 10B:
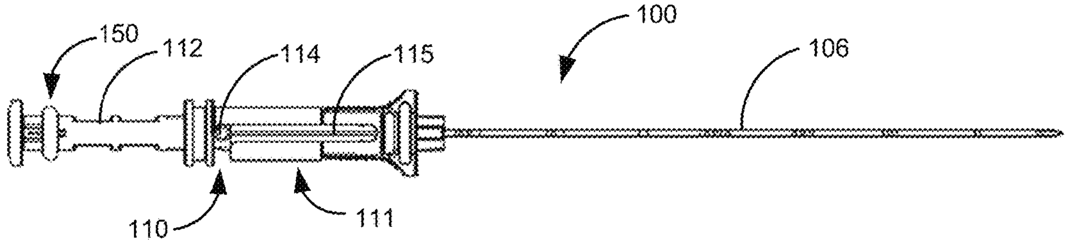
FIG. 10B is the tissue marking device in a fully retracted position.
Figure 10C:
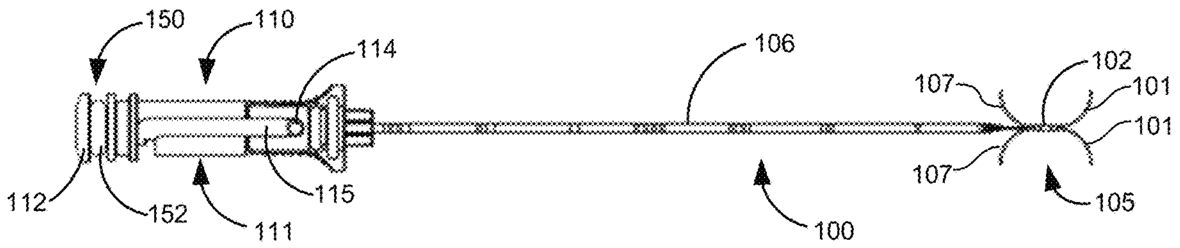
FIG. 10C is the tissue marking device in a full release position.

FIGS. 10A-10C illustrate different release positions of the tissue marking device 100. As illustrated in FIG. 10A, the tissue marking device 100 can be in a partial release position. In the partial release position, the plunger 112 can be actuated and/or depressed until only a portion of the hook assembly 105 is exposed and released out of the needle 106. As illustrated in FIG. 10A, in the partial release position, the plunger 112 may be actuated until the release ring 152 of the release mechanism 150 abuts the handle body 111. The abutment of the release ring 152 against the handle body 111 prevents the user from further actuating and/or depressing the plunger 112 without additional force being applied. The partial release position corresponds to exposing an amount of the hook assembly 105 from the needle 106 while still maintaining the ability to at least partially retract the hook assembly 105 back into the needle 106 towards the fully retracted position as illustrated in FIG. 10B. In at least one example, the hook assembly 105 can still be retractable until the retention mechanism 107 is translated beyond the end of the needle 106. In FIG. 10B, the plunger 112 can be retracted until the hook assembly 105 is fully retracted back into the needle 106. With the release mechanism 150 preventing further deployment of the hook assembly 105 in the partial release position unless additional force is applied, the user can partially deploy the hooks 101 in the hook assembly 105 and still retract the hooks 101 to reset and/or reposition the tissue marking device 100 until the positioning of the hooks 101 is confirmed as desired.

Referring also to FIGS. 8A-8E, the hook assembly 105 can be retracted while the release ring 152 is received in the groove 154 and holding the thread 104 in place. Accordingly, when the plunger 112 is retracted, the thread 104 also pulls back the hook assembly 105 along with the plunger 112. In some examples, in the partial release position, up to 75% of the total length of the hook assembly 105 can be released out of the needle 106. In some examples, in the partial release position, up to 50% of the total length of the hook assembly 105 can be released out of the needle 106.

When the positioning of the hook assembly 105 is confirmed, the tissue marking device 100 can be set into the full release position as illustrated in FIG. 10C. To proceed to the full release position, the plunger 112 is first actuated to the partial release position where the release ring 152 abuts the handle body 111. Upon application of additional force, the release ring 152 can be driven out of the groove 154 to the release portion 156, and the hook assembly 105 is fully deployed out of the needle 106. When fully deployed, the retention mechanism 107 as well as the hooks 101 are deployed such that the hook assembly 105 is embedded in the tissue of the patient at the desired location. In some examples, the retention mechanism 107 may prevent the hook body 102 or hook assembly 105 from retracting back into the needle 106 once the hook assembly 105 has been deployed.

When the release ring 152 is drive out of the groove 154 to the release portion 156, the thread 104 is released from the groove 154 such that the proximal end of the thread 104 is free. When the hook assembly 105 is fully deployed such that the tissue marking device 100 is set into the full release position, the needle 106 can be retracted from the patient while the hook assembly 105 and a portion of the thread 104 remains inside the body. The thread 104 is released from the tissue marking device 100 through the needle 106 so that the needle 106 and handle assembly 110 can be removed. A portion of the thread 104 can extend out of the tissue of the patient.

The retention mechanism 107 and the hooks 101 restrict migration of the hook assembly 105 such that the hook assembly 105 can remain in the patient for an extended period of time. For example, the placement of the hook assembly 105 may occur on a separate day from the surgery to remove the target tissue. In some examples, the placement of the hook assembly 105 may occur up to five days in advance from surgery to remove the target tissue. In some examples, the placement of the hook assembly 105 may occur up to seven days in advance from surgery to remove the target tissue.

Figure 10E:
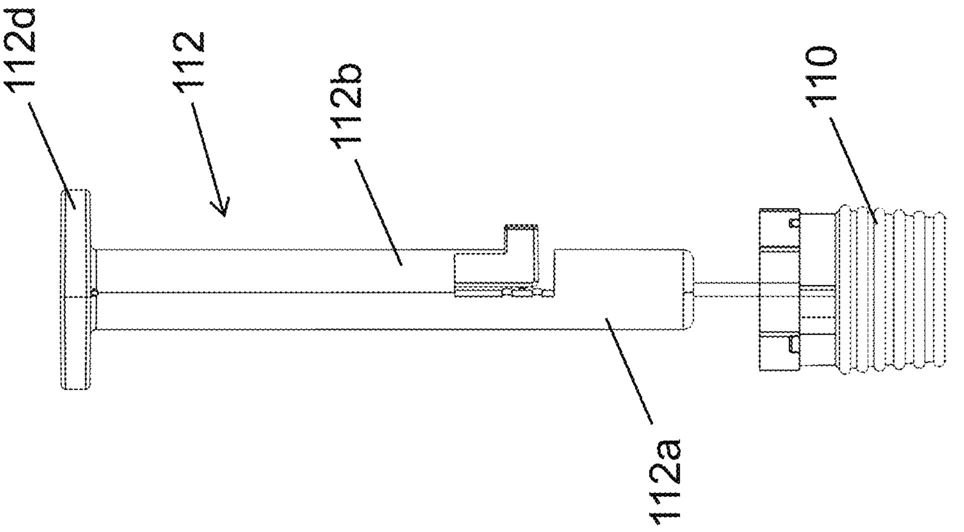
FIG. 10E is a diagram of a plunger of the tissue marking device, according to an illustrative embodiment.
Figure 10D:
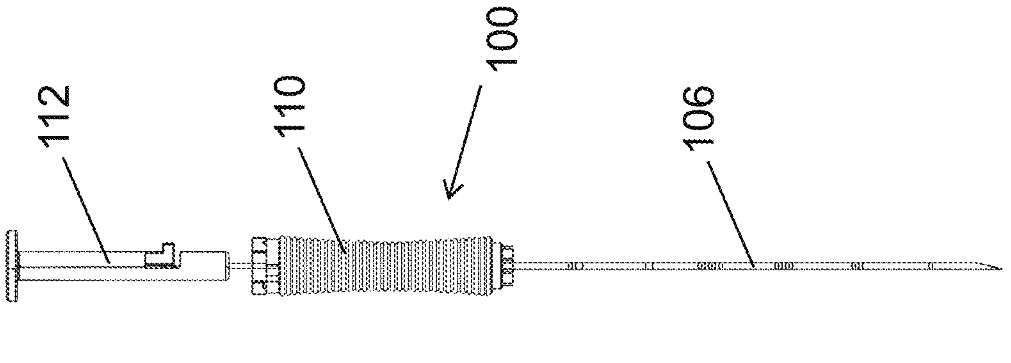
FIG. 10D is a diagram of a tissue marking device, according to an illustrative embodiment.
Figure 10G:
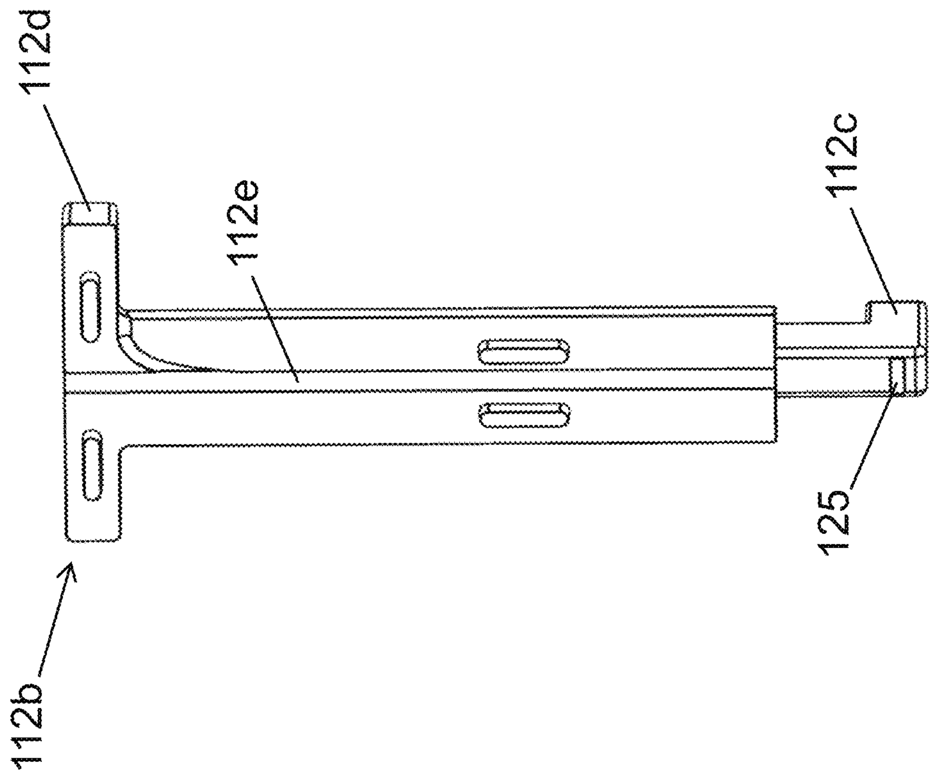
FIG. 10G is a cross-sectional view of a second half of a plunger of the tissue marking device, according to an illustrative embodiment.
Figure 10F:
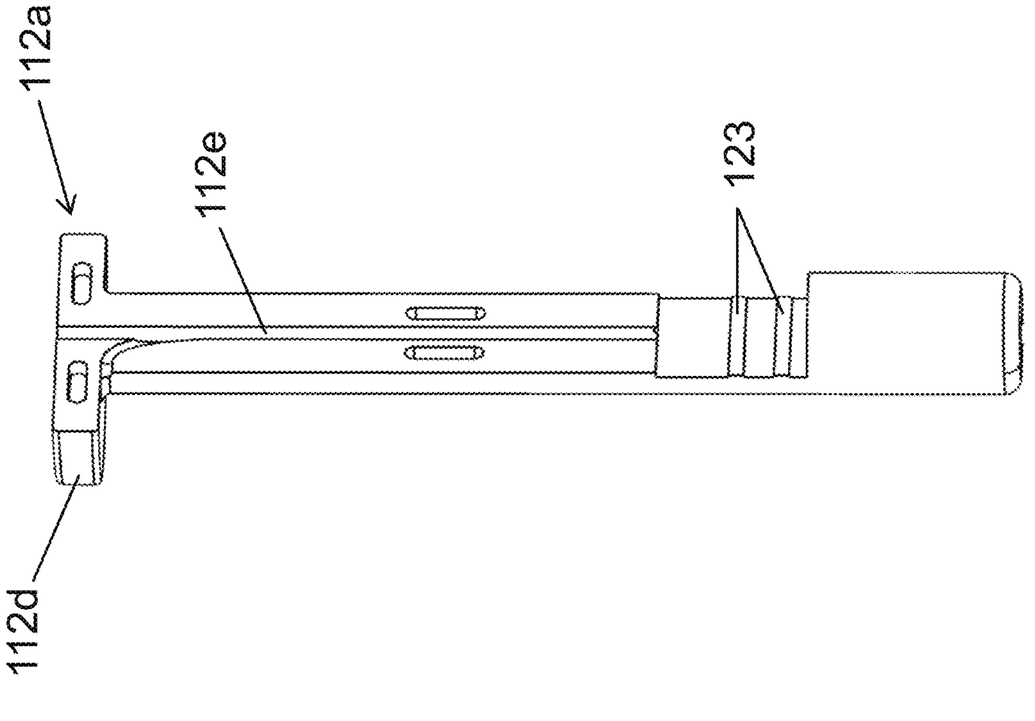
FIG. 10F is a cross-sectional view of a first half of a plunger of the tissue marking device, according to an illustrative embodiment.
Figure 10H:
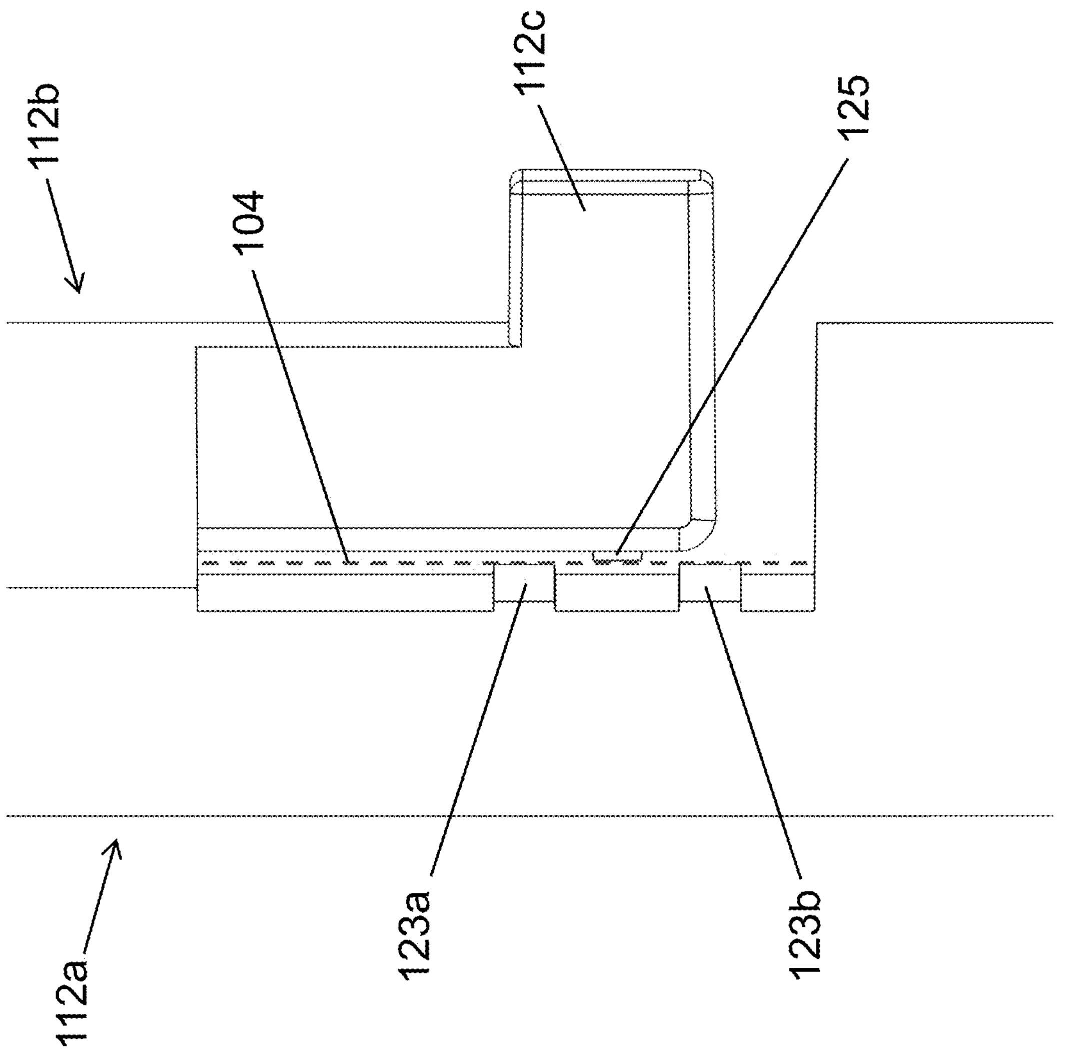
FIG. 10H is a diagram of a portion of a plunger of the tissue marking device, according to an illustrative embodiment.
Figure 10J:
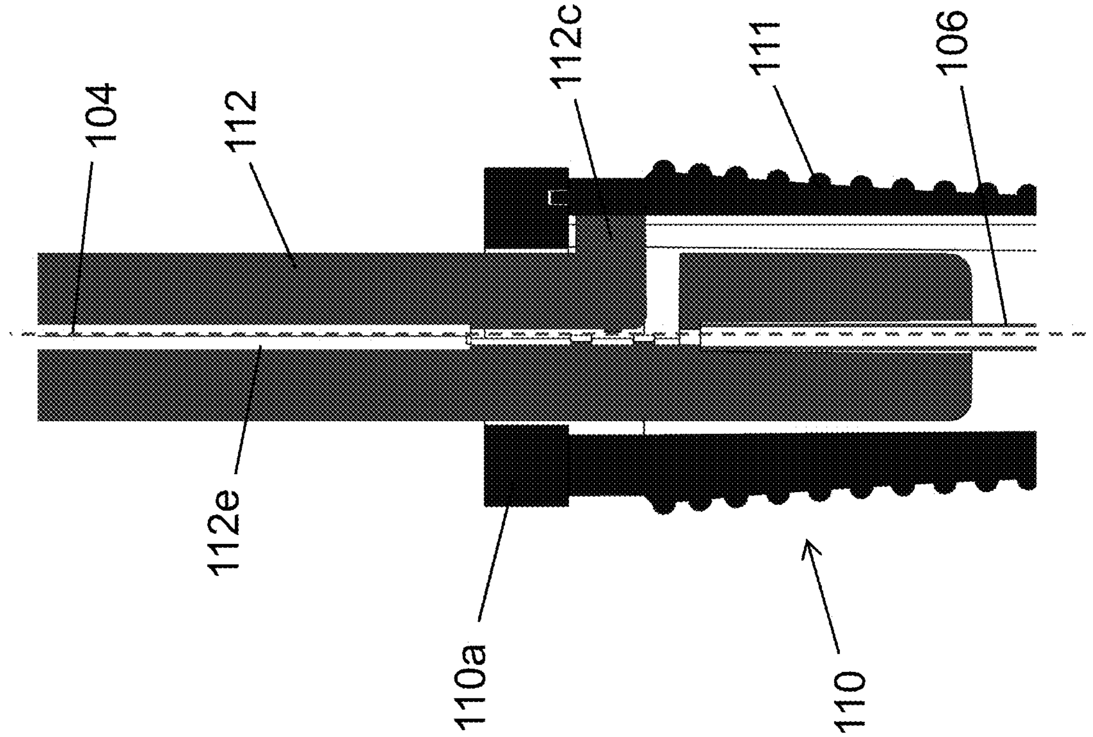
FIG. 10J is a cross-sectional view of an upper portion of a handle assembly of the tissue marking device with a plunger disposed therein, according to an illustrative embodiment.
Figure 10I:
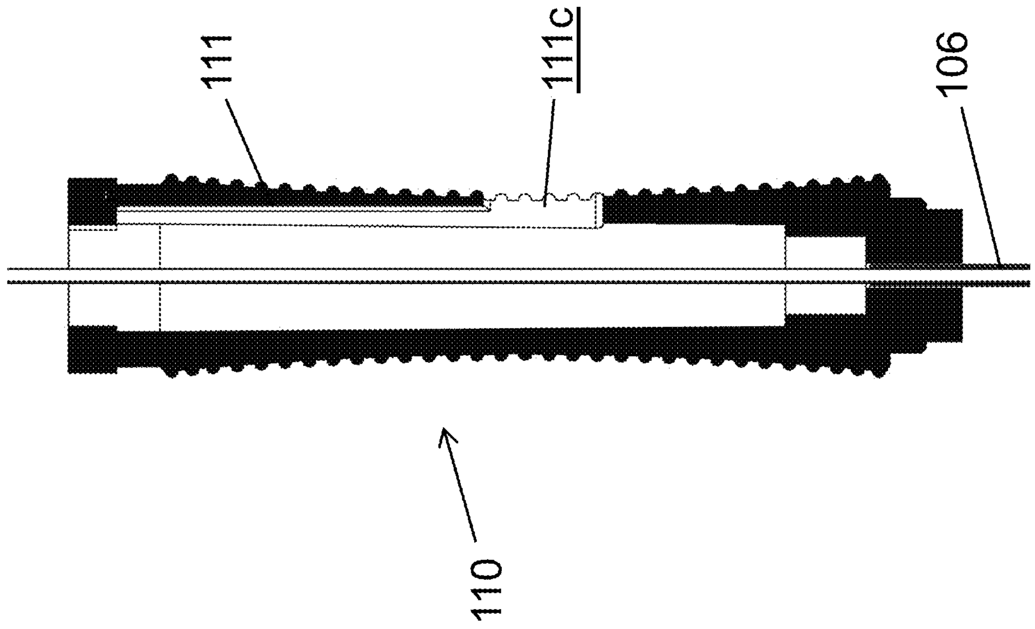
FIG. 10I is a cross-sectional view of a lower portion of a handle assembly of the tissue marking device, according to an illustrative embodiment.
Figure 10M:
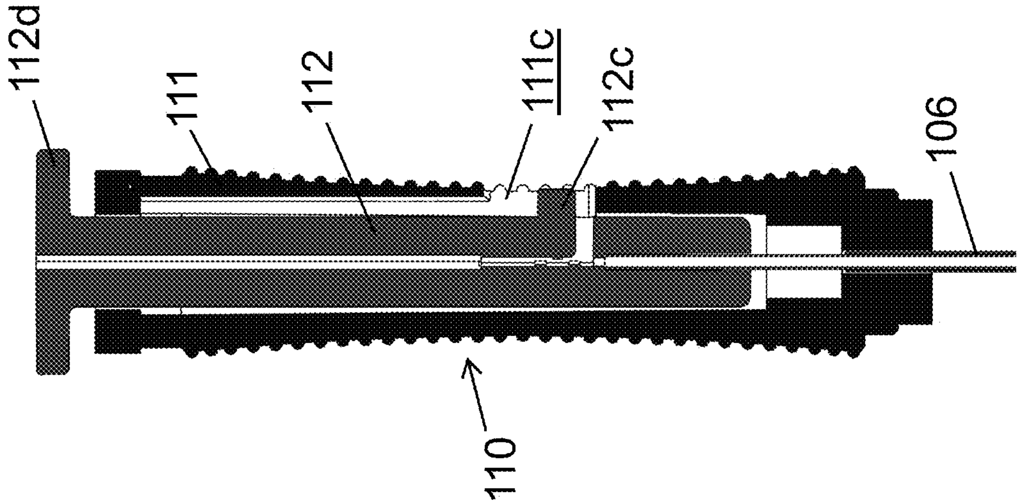
FIG. 10M is a cross-sectional view of the handle assembly and plunger of the tissue marking device in a full release position, according to an illustrative embodiment.
Figure 10L:
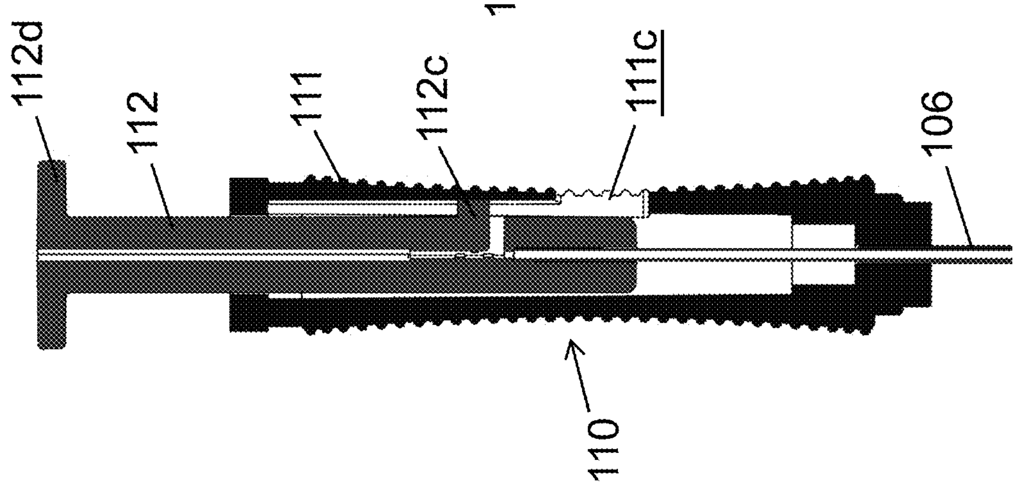
FIG. 10L is a cross-sectional view of the handle assembly and plunger of the tissue marking device in a partial release position, according to an illustrative embodiment.
Figure 10K:
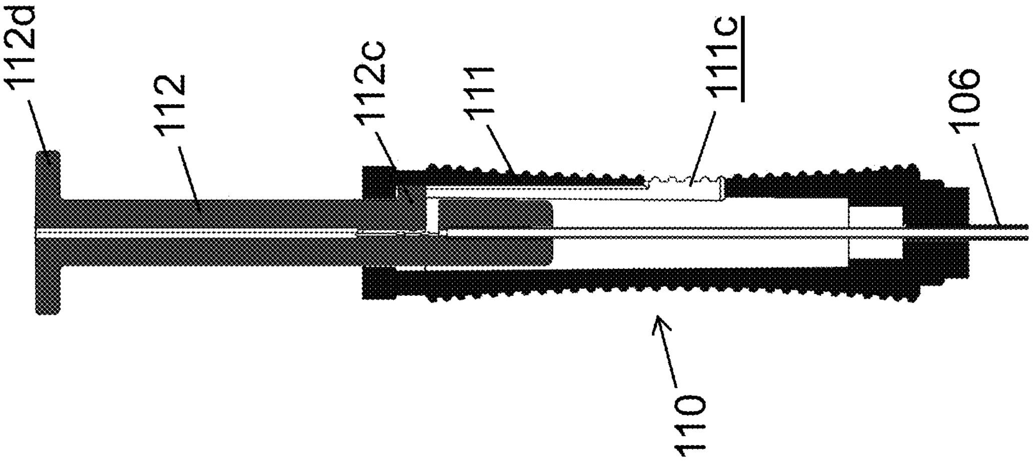
FIG. 10K is a cross-sectional view of the handle assembly and plunger of the tissue marking device in a fully retracted position, according to an illustrative embodiment.
Figure 10N:
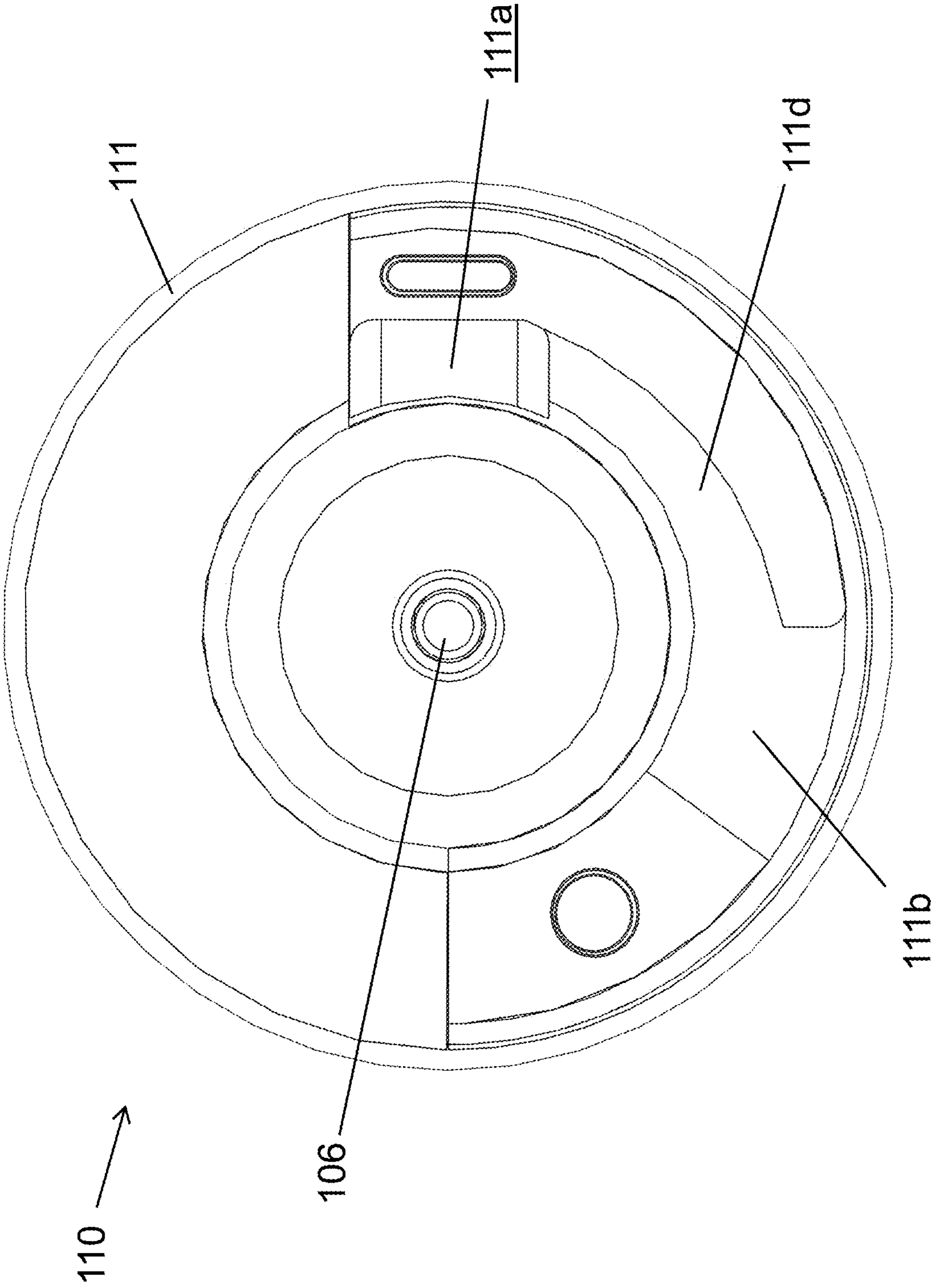
FIG. 10N is a top view of the handle assembly of the tissue marking device, according to an illustrative embodiment.
Figure 10P:
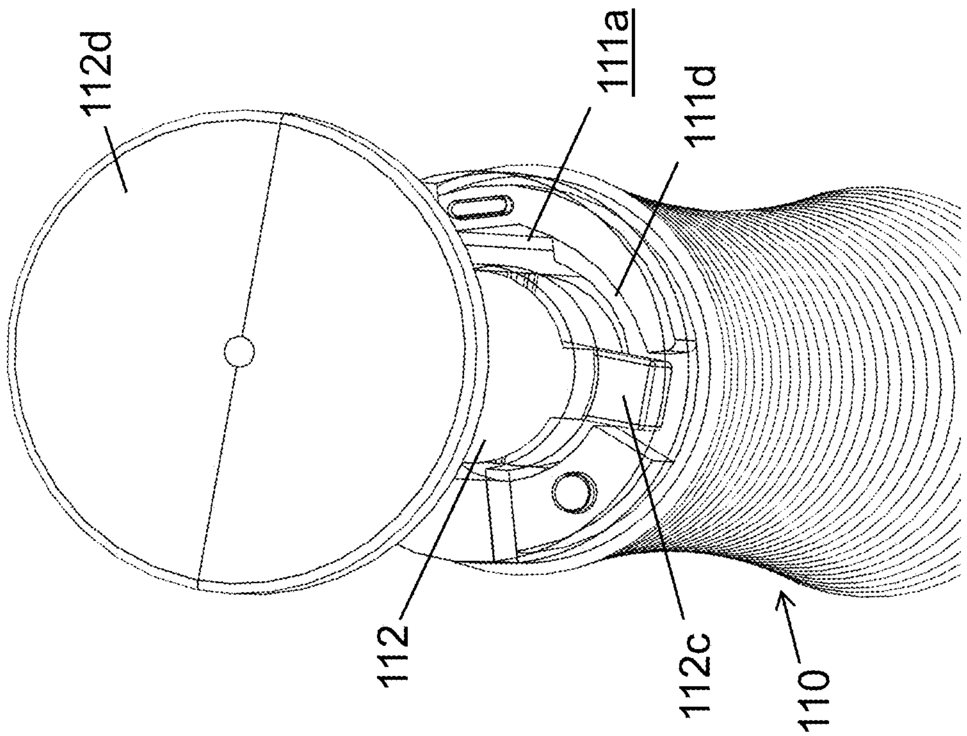
FIG. 10P is a top perspective view of the handle assembly in a locked position, according to an illustrative embodiment.
Figure 10O:
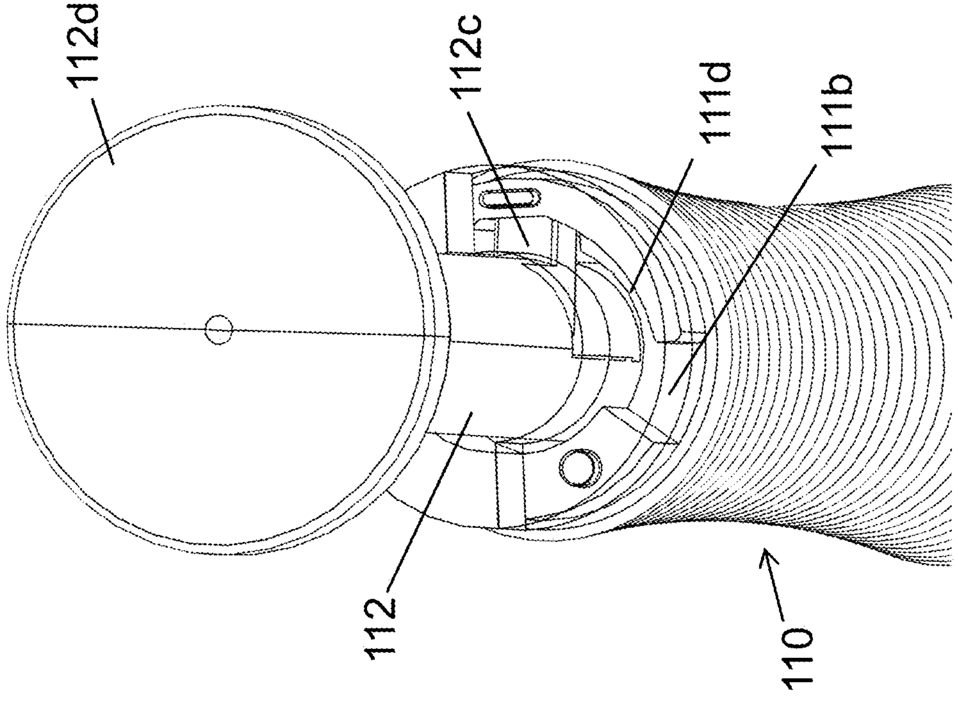
FIG. 10O is a top perspective view of the handle assembly in an unlocked position, according to an illustrative embodiment.

FIGS. 10O-10P illustrate additional variations of the tissue marking device 100. FIG. 10D and FIG. 10E illustrate a partially exploded view of the tissue marking device 100 with the plunger 112 removed from the handle assembly 110 for purposes of illustration. During manufacturing and/or assembly of the tissue marking device 100, at least a portion of the plunger 112 may generally be inserted into or otherwise disposed within the handle assembly 110 such that the plunger is generally incapable of being separated therefrom. By way of non-limiting example, the handle assembly 110 may be a multi-piece (e.g., two-half) design with the pieces mated to one another after at least a portion of the plunger 112 is inserted into or otherwise disposed therein. The handle assembly may also be of unitary construction. By way of further non-limiting example, in a variation, the handle assembly 110 may include a collar 110*a* (refer to FIG. 10J) configured to retain at least a portion of the plunger 112 within the handle assembly 110.

FIGS. 10F-10H illustrate additional aspects of plunger 112 according to another variation. The plunger 112 may include a head portion 112*d* at a proximal end. In variations, the head portion 112*d* may have a greater cross-sectional dimension than a body portion (e.g., defined by first and second members 112*a*, 112*b*, or unitary construction). In such variations, the head portion 112*d* may also have a greater cross-sectional dimension than the handle assembly 110.

The plunger can be selectively to in a full release position, a partial release position, or a fully retracted position. In some variations, the head portion 112 of the plunger 112 may be engaged by a user for selectively moving the plunger, such as for selectively positioning the tissue marking device 100 in a full release position, a partial release position, or a fully retracted position. The proximal end of the plunger, e.g., including the head portion 112 of the plunger 112, may, in variations, be positioned away from the handle assembly 110 (i.e., spaced apart from the handle assembly) when the tissue marking device 100 in a fully retracted position (refer to FIG. 10K). The proximal end of the plunger, e.g. including the head portion 112 of the plunger 112, may, in variations, be positioned closer to the handle assembly 110 (i.e., spaced apart from the handle assembly less than in the fully retracted position) when the tissue marking device 100 in a partial release position (refer to FIG. 10L). The head portion 112 of the plunger 112 may, in variations, abut or be positioned adjacent to the handle assembly 110 when the tissue marking device 100 in a full release position (refer to FIG. 10M).

In a variation, the plunger 112 may be a unitary and monolithically-formed plunger. In other variations, the plunger 112 may include a first member 112*a* and a second member 112*b*, such as is illustrated in FIGS. 10E-10H. The first and second members 112*a*, 112*b* may be mated together by any suitable means to form the plunger 112. FIG. 10F illustrates additional aspects of the first member 112*a* according to another variation.

The plunger can include a channel extending therethrough. In some variations, he channel may extend through a head portion of the plunger. In some variations, the channel can be configured to permit a thread to pass therethrough. In some variations, the channel may extend through the head portion of the plunger. In some variations, the channel may extend through a sidewall of the plunger. In some variations, the channel may extend through both the head portion of the plunger and a sidewall of the plunger.

In some variations, the channel may include one or more thread engagement features configured retain the thread in position within the plunger, such as is illustrated in FIG. 10H and explained herein.

In a variation, at least a portion of the first member 112*a* may define a portion of a channel 112*e* extending therethrough. The channel 112*e* may generally be configured to permit the thread 104 to pass therethrough. In a variation, the channel 112*e* may extend through the head portion 112*d* of the plunger 112. In another variation, the channel 112*e* may extend through a sidewall of the plunger 112. In yet another variation, the channel 112*e* may extend through both the head portion 112*d* of the plunger 112 and a sidewall of the plunger 112. As such, the thread 104 may generally extend through the plunger 112 (e.g., through the channel 112*e* thereof) and extend out of the plunger 112 through the head portion 112*d* or the sidewall of the plunger.

In a variation, the first member 112*a* may include one or more thread engagement features 123. The thread engagement feature(s) 123 may generally be configured to to retain the thread 104 in position within the plunger 112 (e.g., create a mechanical lock), such as is illustrated in FIG. 10H and explained herein.

FIG. 10G illustrates additional aspects of the second member 112*b* of the plunger 112 according to another variation. In a variation, at least a portion of the second member 112*b* may define a portion of a channel 112*e* extending therethrough. When the first and second members 112*a*, 112*b* of the plunger 112 are mated, the channel 112*e* may be formed (refer to FIG. 10J). As described above, the channel 112*e* may generally be configured to permit the thread 104 to pass therethrough. In a variation, the second member 112*b* may include one or more thread engagement features 125. The thread engagement feature(s) 125 may generally be configured to create a mechanical lock so as to retain the thread 104 in position within the plunger 112, such as is illustrated in FIG. 10H and explained herein.

In some variations, the plunger can include a handle engaging element. The handle engaging element may be positioned at the distal end thereof. The handle engaging element may be positioned adjacent to thread engagement feature(s). In a variation, the thread engagement feature(s) may be positioned on the handle engaging element. As explained herein, the handle engaging element may be configured to interface with the handle assembly (e.g., the inner wall thereof), such as is illustrated in FIG. 10J and explained herein. The handle engaging element may generally be of any suitable size and shape for creating the above-described interface lock with the handle assembly (e.g., the inner wall thereof). By way of non-limiting example, in variations, the handle engaging element may be a protrusion or foot (e.g., an "L-shaped" foot) extending outwardly away from the second member. In variations, the handle engaging element may extend outwardly away from the plunger within the handle, thereby effectively increasing a cross-sectional dimension of the second member so as to facilitate the above-described interface with the handle assembly, such as is illustrated in FIG. 10J and explained herein. The thread engagement feature of the plunger can be configured to interface with the handle assembly, or engage in an element within the handle assembly, to lock in position, thereby fully locking the hook and thread in position within a tissue. The element in the handle assembly can be a cavity. The cavity can extent partially into the inner wall of the handle assembly. The cavity can extent fully through the wall of the handle assembly. The handle assembly can be configured to include a receiving element in which the handle engaging element mates, and/or locks.

In a variation, the second member 112*b* may include an handle engaging element 112*c*. The handle engaging element 112*c* of the second member 112*b* may be positioned at the distal end thereof. In a variation, the handle engaging element 112*c* of the second member 112*b* may be positioned adjacent thread engagement feature(s) 125 of the second member. In a variation, the thread engagement feature(s) 125 of the second member 112*b* may be positioned on the handle engaging element 112*c*. As explained herein, the handle engaging element 112*c* may be configured to interface with the handle assembly 110 (e.g., the inner wall thereof), such as is illustrated in FIG. 10J and explained herein. The handle engaging element 112*c* of the second member 112*b* may generally be of any suitable size and shape for creating the above-described interface lock with the handle assembly 110 (e.g., the inner wall thereof). By way of non-limiting example, in variations, the handle engaging element 112*c* of the second member 112*b* may be a protrusion or foot (e.g., an "L-shaped" foot) extending outwardly away from the second member 112*b*. In variations, the handle engaging element 112*c* may extend outwardly away from the second member 112*b*, thereby effectively increasing a cross-sectional dimension of the second member 112*b* so as to facilitate the above-described interface with the handle assembly 110, such as is illustrated in FIG. 10J and explained herein.

FIG. 10H illustrates the first and second members 112*a*, 112*b* of the plunger 112 mated together according to another variation. In variations, the first member 112*a* may generally include one or more thread engagement features 123, and the second member 112*b* may generally include one or more thread engagement features 125. For example, in the variation illustrated in FIG. 10H, the first member 112*a* includes two thread engagement features 123*a*, 123, and the second member 112*b* includes one thread engagement feature 125, though other variations are not so limited. In a variation, the first member 112*a* may include one thread engagement feature 123. In a variation, the first member 112*a* may include two thread engagement features 123. In a variation, the first member 112*a* may include three thread engagement features 123. In a variation, the first member 112*a* may include four or more thread engagement features 123. In a variation, the second member 112*b* may include one thread engagement feature 125. In a variation, the second member 112*b* may include two thread engagement features 125. In a variation, the second member 112*b* may include three thread engagement features 125. In a variation, the second member 112*b* may include four or more thread engagement features 125. In variations, the thread engagement feature(s) 123 of the first member 112*a* may generally be spaced apart from the thread engagement feature(s) 125 of the second member 112*b*. For example, in the variation illustrated in FIG. 10H, the thread engagement features 123*a*, 123 of the first member 112*a* are vertically spaced apart from one another, and the thread engagement feature 125 of the second member 112*b* is positioned vertically between the thread engagement features 123*a*, 123 of the first member 112*a*, though other variations are not so limited. In variations in which the first member 112*a* and/or the second member 112*b* includes multiple thread engagement features, the thread engagement features of the first member may generally be interleaved with the thread engagement features of the second member.

As described above, the thread engagement features 123, 125 of the first and second members 112*a*, 112*b* may generally be configured to create a mechanical lock so as to retain the thread 104 in position within the plunger 112. By way of non-limiting example, the thread engagement features 123, 125 of the first and second members 112*a*, 112*b* may be configured to impart a force (e.g., a compressive force) upon the thread 104 as the thread passes thereby or therethrough. The mechanical lock imparted by the thread engagement features 123, 125 may be created due to the interface between the handle engaging element 112*c* of the plunger 112 and the handle assembly 110 (e.g., the inner wall thereof), such as is illustrated in FIG. 10J and explained herein. The thread engagement features 123, 125 of the first and second members 112*a*, 112*b* may generally be of any suitable size and shape for creating the above-described mechanical lock with the thread 104. By way of non-limiting example, in variations, the thread engagement feature(s) 123 of the first member 112*a* and/or the thread engagement feature(s) 125 of the second member 112*b* may be protrusions or ridges extending outwardly away from corresponding ones of the first and second members 112*a*, 112*b*. In such variations, the thread engagement feature(s) 123 of the first member 112*a* in the form of protrusions or ridges may generally extend in a direction toward the second member 112*b*, and the thread engagement feature(s) 125 of the second member 112*b* may in the form of protrusions or ridges may generally extend in a direction toward the first member 112*a*. In a variation, the thread engagement feature (s) 125 of the second member 112*b* may be protrusions or ridges extending outwardly away from the handle engaging element 112*c* of the second member 112*b*.

The thread engagement features can be formed of unitary construction, without a first member 112*a* and second member 112*b*. That is to say, the engagement members can be formed in a plunger that does not include two independent parts, and of unitary construction. Likewise, the locking mechanism can be formed of unitary construction in the plunger.

When fully deployed, the retention mechanism as well as the hooks are deployed such that the hook assembly is embedded in the tissue of the patient at the desired location. In some examples, the retention mechanism may prevent the hook body or hook assembly from retracting back into the needle once the hook assembly has been deployed.

FIG. 10I illustrates additional aspects of the handle assembly 110 according to another variation. As described above, the handle assembly 110 may include a handle body 111. The handle body 111 may include an handle engaging element 111*c*. The handle engaging element 111*c* of the handle body 111 may generally be positioned between the proximal and distal ends thereof. In a variation, the handle engaging element 111*c* may be positioned a selected distance from the proximal end of the handle body 111 corresponding to a length of a portion of the plunger 112. More specifically, the handle engaging element 111*c* of the handle body 111 may be selectively positioned such that the handle engaging element 111*c* of the handle body 111 is configured to engage or interface with (e.g., by receiving and/or retaining) the handle engaging element 112*c* of the plunger 112 when the plunger is in the full release position, such as is illustrated in FIG. 10M and explained herein.

Conversely, the handle engaging element 111*c* of the handle body 111 may be selectively positioned such that the handle engaging element 111*c* of the handle body 111 does not engage or interface with (e.g., does not receive and/or retain) the handle engaging element 112*c* of the plunger 112 when the tissue marking device 100 is in the fully retracted position (refer to FIG. 10K) or a partial release position (refer to FIG. 10L), as explained herein. The handle engaging element 111*c* of the handle body 111 may generally be of any suitable size and shape for engaging with the handle engaging element 112*c* of the plunger 112 as described above. By way of non-limiting example, in variations, the handle engaging element 111*c* of the handle body 111 may be a notch or cavity extending inwardly into the handle body 111. By way of further non-limiting example, in variations, the handle engaging element 111*c* of the handle body 111 may be an aperture or window extending through the handle body 111. In the aforementioned variations, the handle engaging element 111*c* may extend inwardly into or through the handle body 111 so as to facilitate the above-described receipt and/or retainment of the handle engaging element 112*c* of the plunger 112, such as is illustrated in FIG. 10M and explained herein.

With reference to FIG. 10J, the above-described interface between the handle engaging element 112*c* of the plunger 112 and the handle assembly 110 (e.g., the inner wall of the handle body 111) is illustrated according to another variation. As the plunger 112 is moved through the handle assembly 110, the tissue marking device 100 may transition from a fully retracted position (refer to FIG. 10K) to a partial release position (refer to FIG. 10L), and the plunger 112 may interface with the handle assembly 110 in each position. More specifically, there may exist an interference between the handle engaging element 112*c* of the plunger 112 and the inner wall of the handle body 111 in each position. Such interface and/or interference may generally cause the thread engagement feature(s) 123, 125 of the first and second members 112*a*, 112*b* of the plunger 112 to create a mechanical lock and/or impart a force (e.g., a compressive force) upon the thread 104 so as to retain the thread in position within the plunger 112 as the thread passes by or through the thread engagement features, as explained herein.

As illustrated in FIG. 10K and as explained above, the tissue marking device 100 can be in a fully retracted position. The plunger 112 may be moved within the handle assembly 110 such that the tissue marking device 100 is transitioned into a partial release position as illustrated in FIG. 10L. In each of the fully retracted position and the partial release position, the handle engaging element 112*c* of the plunger 112 may interface with the inner wall of the handle body 111 of the handle assembly 110 as described above. As such, the thread 104 may be retained (e.g., via pinching) by the thread engagement feature(s) as described above. The plunger 112 may be further moved within the handle assembly 110 such that the tissue marking device 100 is transitioned into the full release position as illustrated in FIG. 10M. In the full release position, the handle engaging element 112*c* of the plunger 112 may discontinue interfacing with the inner wall of the handle body 111 of the handle assembly 110 as described above and may, instead, engage with the handle engaging element 111*c* of the handle body (e.g., by being received or retained thereby) as described above. As such, the thread 104 may be released from retainment (e.g., via releasing of the pinching) by the thread engagement feature(s) as described above. As may be understood with continued reference to FIG. 10K and FIG. 10L, the handle engaging element 112*c* of the plunger 112 may generally be configured to interface with the handle body 111 of the handle assembly 110 (e.g., the inner wall of the handle body 111) and generally may not engage with the handle engaging element 111*c* of the handle body 111 when the tissue marking device 100 is in the fully retracted position (refer to FIG. 10K) or a partial release position (refer to FIG. 10L). Conversely, as may be understood with reference to FIG. 10M, the handle engaging element 112*c* of the plunger 112 may generally be configured to engage with the handle engaging element 111*c* of the handle body 111 and generally may not interface with the handle body 111 of the handle assembly 110 when the tissue marking device 100 is in the fully release position.

FIG. 10N is a top view of the handle assembly 110 and illustrates additional aspects of the proximal end of the handle assembly according to another variation. FIG. 10O and FIG. 10P show the tissue marking device 100 in the fully retracted position, with the plunger 112 selectively rotated between an unlocked position (refer to FIG. 10O) and a locked position (refer to FIG. 10P). In the locked position, the plunger 112 is generally incapable of being moved within the handle assembly 110 from the fully retracted position. In the unlocked position, on the other hand, the plunger 112 is generally capable of being moved within the handle assembly 110 from the fully retracted position to a partial release position or the full release position. The plunger 112 may be selectively transitioned from the unlocked position to the locked position, such is illustrated between FIG. 10O and FIG. 10P. To transition the plunger 112 from the unlocked position to the locked position, the plunger 112 may generally be moved or rotated (e.g., clockwise). As the plunger 112 is moved or rotated from the unlocked position to the locked position, the handle engaging element 112*c* of the plunger 112 may translate across a ramp or retaining ridge 111*d* of the handle body 111. In variations, the ramp or retaining ridge 111*d* may extend inwardly from the inner wall of the handle body 111, thereby effectively decreasing a cross-sectional dimension of the handle body 111 at the proximal end of the handle assembly 110 such that the handle engaging element 112*c* of the plunger 112 rests thereupon and the plunger is incapable of being moved within the handle assembly 110 from the fully retracted position, such as is illustrated in FIG. 10P.

In variations, the ramp or retaining ridge 111*d* may extend from adjacent an unlocking feature 111*a* of the handle body 111 and may terminate at a locking feature 111*b* of the handle body 111. In variations, the ramp or retaining ridge 111*d* of the handle body 111 may be tapered from adjacent the unlocking feature 111*a* of the handle body 111 to the locking feature 111*b* of the handle body 111, such as is illustrated in FIG. 10N. Put another way, the ramp or retaining ridge 111*d* may extend inwardly from the inner wall of the handle body 111 such that the cross-sectional dimension of the handle body 111 across the ramp or retaining ridge 111*d* gradually decreases as the ramp or retaining ridge extends from the from adjacent the unlocking feature 111*a* of the handle body to the locking feature 111*b* of the handle body. The ramp or retaining ridge 111*d* may, in variations, be configured to assist in building up the above-described interface and/or interference between the handle engaging element 112*c* of the plunger 112 and the inner wall of the handle body 111.

The locking feature 111*b* of the handle body 111 may generally be configured to engage or interface with (e.g., by receiving and/or retaining) the handle engaging element 112*c* of the plunger 112. The locking feature 111*b* of the handle body 111 may generally be of any suitable size and shape for engaging or interfacing with the handle engaging element 112*c* of the plunger 112 so as to prevent or retard the plunger 112 from being capable of being moved within the handle assembly 110 from the fully retracted position as described above. By way of non-limiting example, in variations, the locking feature 111*b* of the handle body 111 may be a notch or cavity extending inwardly into the handle body 111 at the proximal end of the handle assembly 100. By way of further non-limiting example, in variations, the locking feature 111*b* of the handle body 111 may be an aperture or window extending through the handle body 111 at the proximal end of the handle assembly 100. In the aforementioned variations, the locking feature 111*b* may extend inwardly into or through the handle body 111 so as to facilitate the above-described receipt and/or retainment of the handle engaging element 112*c* of the plunger 112, such as is illustrated in FIG. 10P. The unlocking feature 111*a* of the handle body 111, on the other hand, may generally be configured not to engage with or interface with the handle engaging element 112*c* of the plunger 112. The unlocking feature 111*a* of the handle body 111 may generally be of any suitable size and shape for permitting the plunger 112 to be capable of being moved within the handle assembly 110 from the fully retracted position to a partial release position or the full release position as described above. By way of non-limiting example, in variations, the unlocking feature 111*a* of the handle body 111 may be a slot sized to permit the handle engaging element 112*c* of the plunger 112 to pass therethrough, such as is illustrated in FIG. 10O. In a variation, the plunger 112 may rotated about 90° to transition the plunger from the unlocked position to the locked position, or vice versa, though other variations are not so limited.

Figure 10Q:
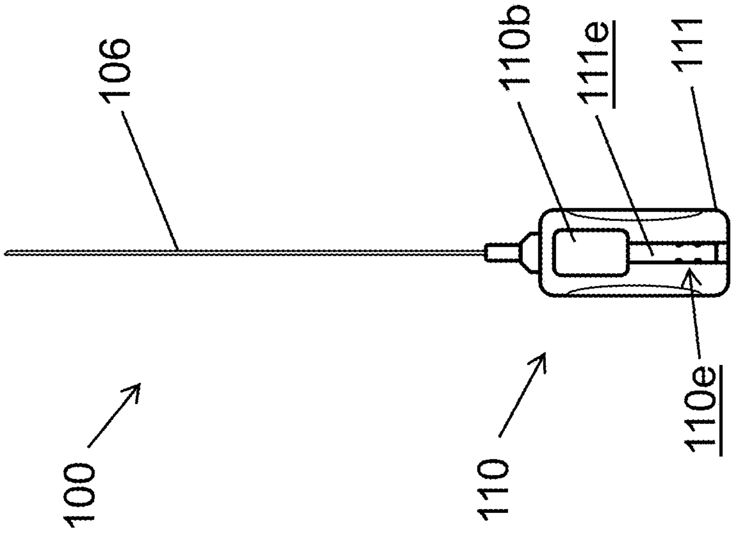
FIG. 10Q is a diagram of a tissue marking device, according to an illustrative embodiment.
Figure 10R:
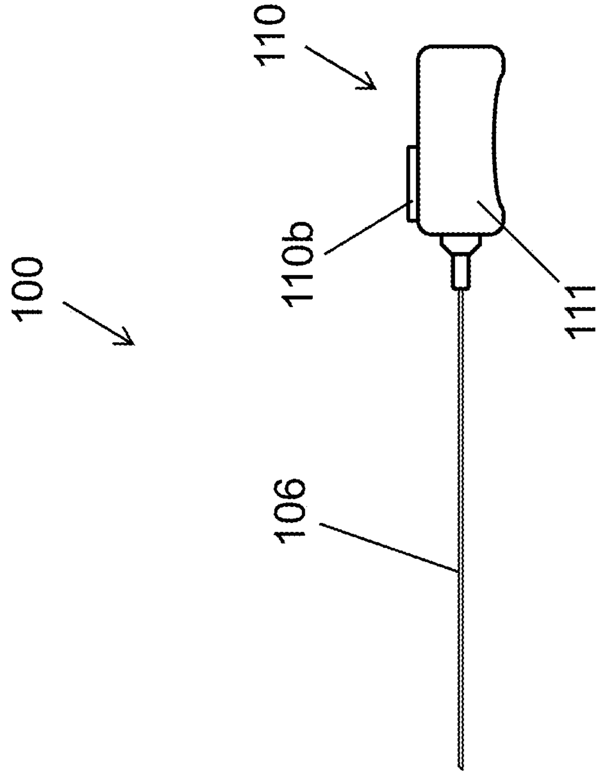
FIG. 10R is a side view of the tissue marking device of FIG. 10Q, according to an illustrative embodiment.

FIG. 10Q and FIG. 10R illustrate an additional variation of the tissue marking device 100. FIG. 10Q is a top view of the tissue marking device 100, and FIG. 10R is a side view of the tissue marking device. In the variation illustrated in FIG. 10Q and FIG. 10R, the handle assembly 110 may include a lever or pusher 110*b*. In a variation, the lever or pusher 110*b* may be at least partially disposed within the handle body 111. In a variation, the lever or pusher 110*b* may be at least partially disposed within a slot 111*e* defined in the handle body 111. In variations, the lever or pusher 110*b* may be operably affixed or otherwise connected to the stylet or the needle 106. The lever or pusher 110*b* may be configured to selectively translate (e.g., by sliding) along the handle body 111 in either the proximal and/or the distal directions. As may be appreciated, translation of the lever or pusher 110*b* axially along the handle body 111 (e.g., within the slot 111*e* thereof) may selectively advance the stylet out of the needle 106, which may, in certain variations, cause and the hooks and/or retention mechanism to expand or deploy because they are no longer compressed by the needle 106, as described herein. Conversely, translation of the lever or pusher 110*b* axially along the handle body 111 (e.g., within the slot 111*e* thereof) in the opposite direction may selectively retract the stylet into the needle 106 as desired. The use of a lever or pusher 110*b* as described herein may be preferable for certain users, namely for ultrasound. Such a lever or pusher 110*b* may also provide an ergonomic means by which a user can engage with and selectively move the tissue marking device 100 between the deployed and retracted positions, including conveniently through the use of a single action (e.g., thumb depression). In variations, the length of the slot 111*e* may be configured to correspond to the distance required to move the tissue marking device 100 between the deployed and retracted positions. The handle body 111 may, in variations, include one or more features 110*e* configured to engage with the lever or pusher 110*b* so as to lock the lever or pusher in a specific axial position, as described herein.

Figure 11A:
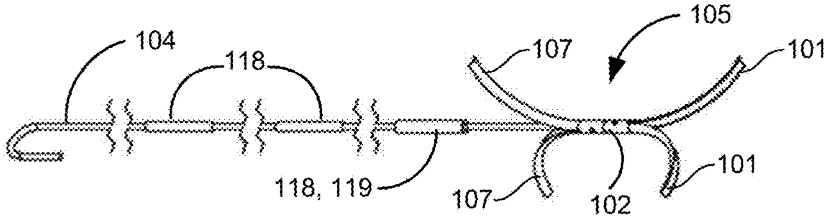
FIG. 11A is a diagram of a thread with orthogonal hooks, according to an illustrative embodiment.

FIGS. 11A-11G illustrates examples of hook assemblies 105. In some examples, as illustrated in FIG. 11A, the hook assembly 105 may be arranged where the hooks 101 and/or the retention mechanisms 107 are orthogonal from one another. The hooks 101 and/or retention mechanisms 107 being orthogonal from one another provides an enhanced cross-section. In at least one example, the enhanced cross-section can provide better visualization under various imaging mechanisms. In some examples, the enhanced cross-section can provide increased anchoring force to have minimum migration of the hook assembly 105 within the patient from the time of lesion localization to removal in surgery so that the hook assembly 105 can remain in the patient for an extended period of time, for example up to seven days.

Figures 11B, 11C, 11D, 11E, 11F, 11G:
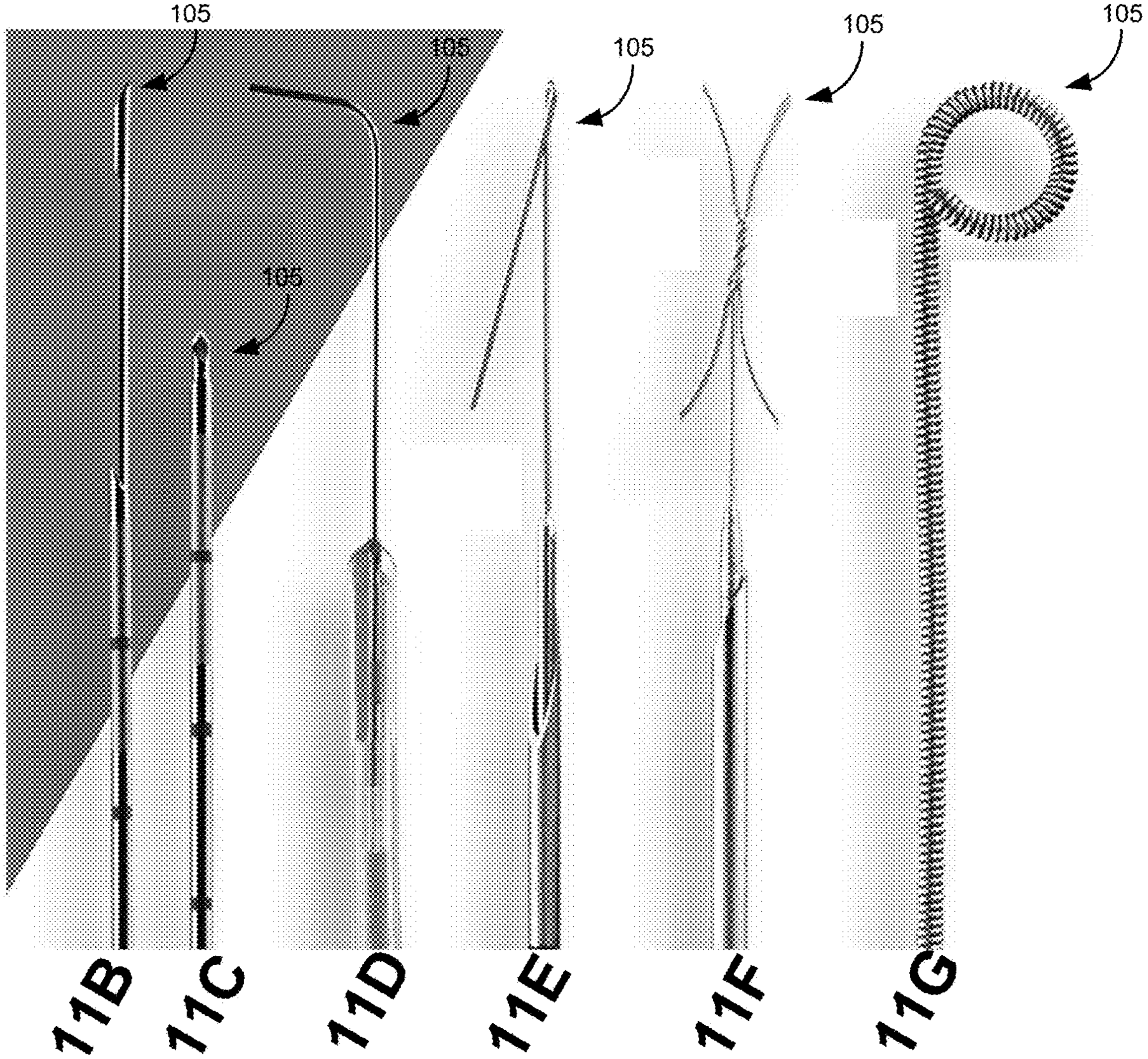
FIG. 11B-11G illustrate examples of hook assemblies, according to illustrative embodiments.

FIGS. 11B-11G illustrate different examples of shapes of hook assemblies 105. FIG. 11B illustrates a hook assembly 105 with the shape of a biopsy needle having a hollow core. FIG. 11C illustrates a hook assembly 105 with the shape of a biopsy needle having a hollow core. FIG. 11D illustrates a hook assembly 105 with an orthogonal curve. FIG. 11E illustrates a hook assembly 105 where the hook assembly 105 is looped back onto itself where the end of the hook assembly 105 is disposed at an angle to the hook assembly 105 extending from the thread 104. As illustrated in FIG. 11F, the hook assembly 105 can be formed substantially in an X shape. FIG. 11G illustrates a hook assembly 105 in the form of a coil. In some examples, as illustrated in FIG. 11G, the hook assembly 105 can be formed in a substantially circular loop.

Figure 12A:
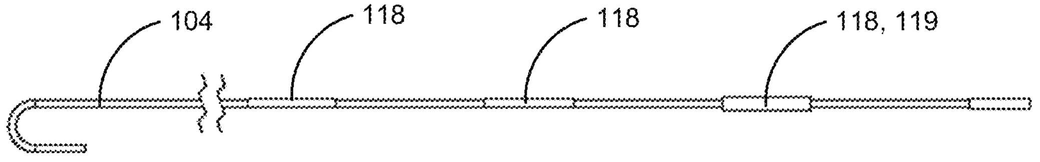
FIG. 12A-12C are diagrams of a thread with marker bands, according to illustrative embodiments.
Figure 12B:
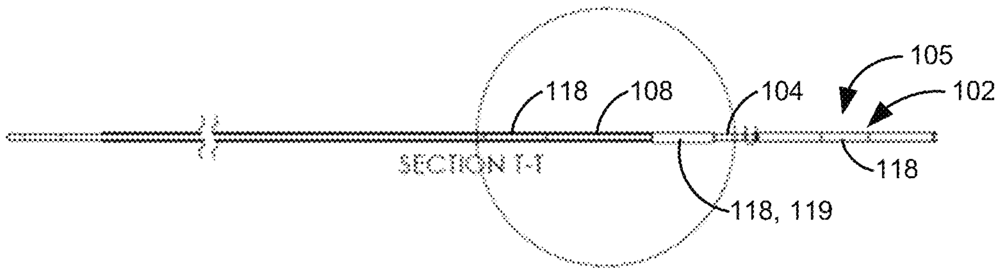
Figure 12C:
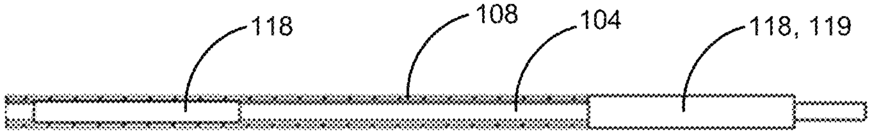

FIGS. 12A-12C illustrate examples of a thread 104 with one or more marker bands 118. As discussed above, the marker bands 118 may be placed within a predetermined distance from one another along the thread 104 to indicate a set distance from where the thread connects to the hook body 102, such as the center of the hook body 102. In some examples, as illustrated in FIG. 12B, the hook body 102 may include a marker band 118 disposed in and/or along the hook body 102 to mark, for example, the center of the hook body 102. In at least one example, the marker bands 118 may be disposed a distance of 1 centimeter from one another. In some examples, the marker bands 118 may include one or more marker bands 118 disposed on the hook assembly 105 such as on the hook body 102. In some examples, the marker bands 118 may be disposed equidistant from one another. In other examples, the marker bands 118 may be disposed at differing distances from one another. The distances between the marker bands 118 are predetermined such that the user can measure the distance from the hook assembly 105 using the marker bands 118.

In at least one example, the marker bands 118 may include platinum-iridium. In some examples, the marker bands 118 may include nitinol. In some examples, the marker bands 118 may include material such that the marker bands 118 may be visible by an imaging mechanism. For example, the material of the marker bands 118 may be fluorescent. In at least one example, one or more of the marker bands 118 may each extend radially from the thread 104 and/or the hook assembly 105 such that the marker bands 118 can serve as a tactile guide. For example, the marker bands 118 may include a palpable bead. The palpable beads may be placed at 1 centimeter intervals to produce a rapid visual reference to the lesion and provide an excellent reference point for the surgeon.

In at least one example, the hook assembly 105 can be detected by one or more imaging modalities at any stage of partial deployment. In some examples, the hook assembly 105 can be detected by one or more imaging modalities at any stage of full deployment. In at least one example, one or more of the marker bands 118 can be detected by one or more imaging modalities at any stage of partial deployment. In some examples, one or more of the marker bands 118 can be detected by one or more imaging modalities at any stage of full deployment.

In some examples, the imaging modalities may include mammography. For example, the needle 106 can be placed in the breast of the patient. The needle 106 may include measurement markings to judge depth. An x-ray from a single plane at a time may be taken to determine whether the needle 106 extends through the mass. The needle 106 can then be removed, and another x-ray may be taken to confirm the hook assembly 105 is positioned correctly, for example slightly past the mass. The marker bands 118 can assist in confirming the relative placement of the hook assembly 105.

In some examples, the imaging modalities may include tomosynthesis. For example, the needle 106 can be placed in the breast of the patient. The needle 106 may include measurement markings to judge depth. Images, such as x-ray images, from multiple angles or planes may be taken to determine whether the needle 106 extends through the mass. By taking images from multiple angles, a three-dimensional map of the anatomy of the patient and the marker bands 118 may be produced. The needle 106 can then be removed, and another set of images may be taken to confirm the hook assembly 105 is positioned correctly, for example slightly past the mass. The marker bands 118 can assist in confirming the relative placement of the hook assembly 105.

In some examples, the imaging modalities may include ultrasound. For example, the needle 106 can be placed in the breast of the patient, and the user can have real-time feedback on the relative location of the needle 106 with the ultrasound imaging. When the hook assembly 105 is deployed, the needle 106 can be removed, and an image, for example an x-ray taken in a mammography suite, may be taken to confirm the hook assembly 105 is positioned correctly, for example slightly past the mass. The marker bands 118 can assist in confirming the relative placement of the hook assembly 105.

The marker bands 118 are each separated, for example along the thread 104, a predetermined distance. Accordingly, the marker bands 118 can accurately be used as a measuring tool. When the stylet 108 pushes the hook assembly 105 out of the needle 106, the thread 104 may bend or kink. To prevent such bending, in at least one example as illustrated in FIGS. 12A-12C, the stylet 108 may be provided over a number of the marker bands 118 on the thread 104 to abut and push against the front marker band 119. The front marker band 119 may be the marker band 118 most proximal to the hook assembly 105. In at least one example, when the hook assembly 105 is in restrained within the needle 106, the retention mechanism(s) 107 may be disposed proximate to and/or abut against the front marker band 119. The distance between the hook assembly 105 such as the retention mechanism(s) 107 and front marker band 119 can be a set distance. Placing the front marker band 119 at a distance where the retention mechanism(s) 107 of the hook assembly 105 when restrained in the needle 106 abuts against the front marker band 119 allows for direct transmission of force from the stylet 108 to the front marker band 119 and to the hook assembly 105. If the distance is not precisely defined, then the thread 104 may buckle or bend undesirably.

The front marker band 119 may have a larger diameter and extend radially from the thread 104 a greater amount than the subsequent marker bands 118. As illustrated in FIG. 12C, the stylet 108 may extend over the marker bands 118 and the thread 104 until the end of the stylet 108 abuts the front marker band 119. The stylet 108 can then push against the front marker band 119 to deploy and push the hook assembly 105 out of the needle 106.

In at least one example, instead of abutting the front marker band 119, the stylet 108 may extend over all of the marker bands 118 including the front marker band 119 and abut and push against a portion of the hook assembly 105. In at least one example, the thread 104 may include an extension portion disposed proximate to the hook assembly 105 between the hook assembly 105 and the front marker band 119. The extension portion may extend radially from the thread 104 and is operable to abut against the stylet 108 to deploy the hook assembly 105.

In at least one example, the stylet 108 is operable to abut the front marker band 119 to push the marker band 119 and hook assembly 105 out of the needle, but can detach from the front marker band 119 so that the stylet 108 can be retracted and removed from the patient along with the needle 106, leaving the hook assembly 105 and a portion of the thread 104. In at least one example, the front marker band 119 may have an end squared off to abut against the stylet 108. In some examples, to enable the hook assembly 105, the thread 104, and/or the front marker band 119 to rotate along with the stylet 108, the end of the front marker band 119 may include a mating feature to correspond with a mating feature at the end of the stylet 108. For example, the mating features may include one or more extensions operable to abut one another upon rotation and enable rotation of the front marker band 119 along with the stylet 108. In at least one example, the mating features may include crown-shaped extensions, rectangular-shaped extensions, or any other suitable shaped extensions.

Figure 13A:
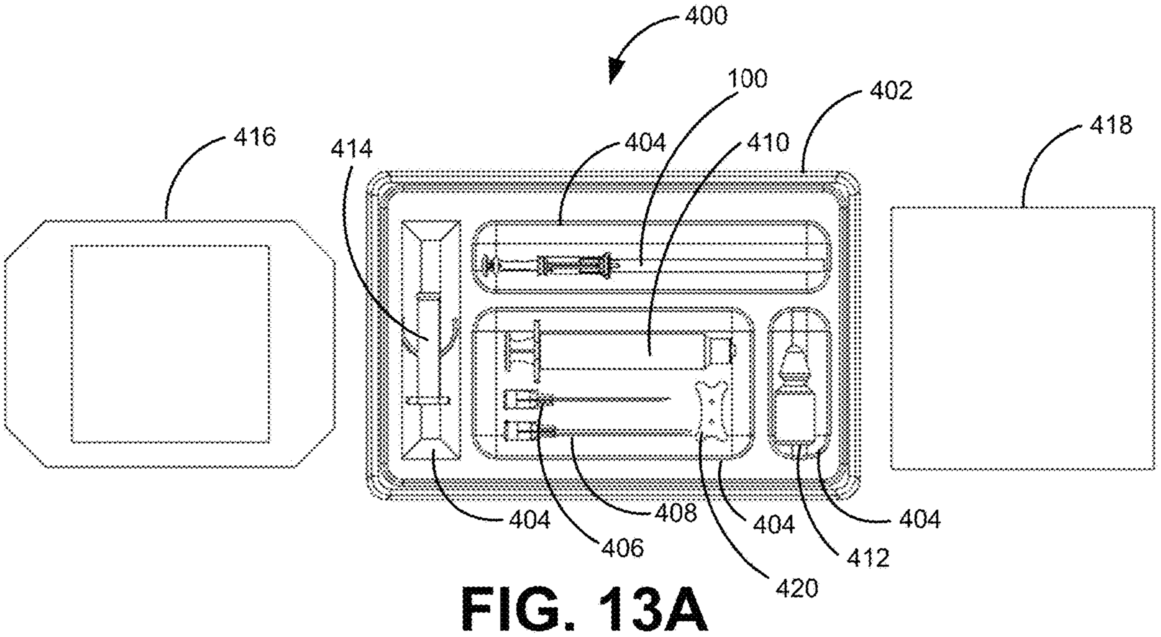
FIGS. 13A and 13B are diagrams of a kit with a tissue marking device, according to an illustrative embodiment.
Figure 13B:
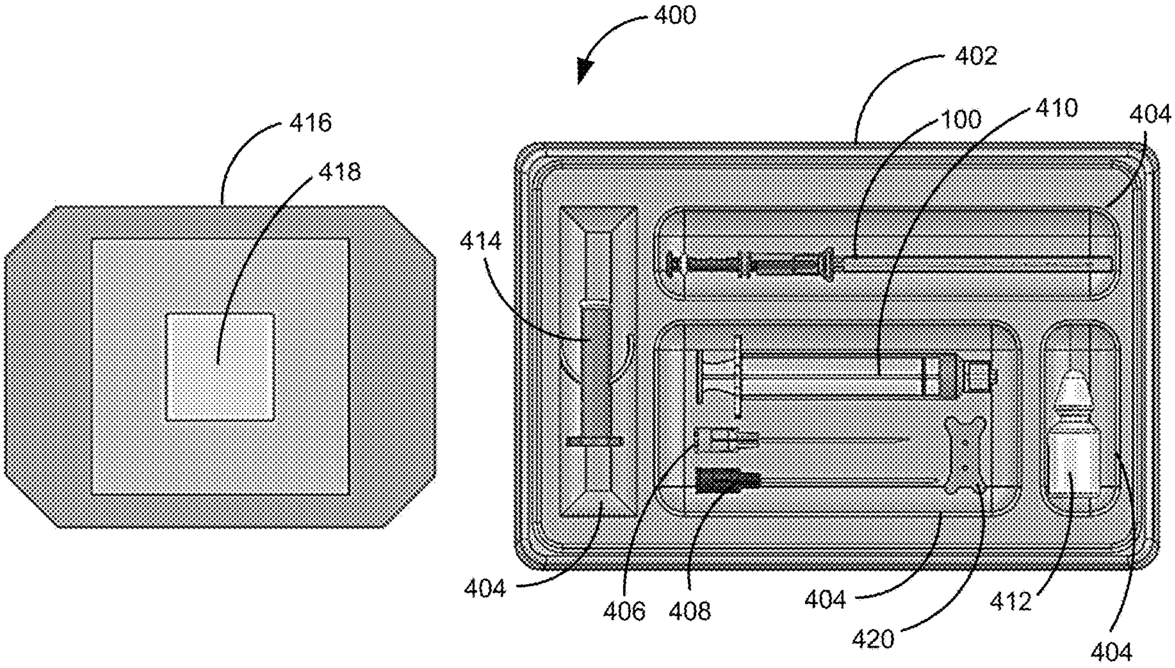

FIGS. 13A and 13B illustrate examples of kits 400 operable to contain and provide the tissue marking device 100 and/or any other suitable or desirable components to be used with the tissue marking device 100. For example, as illustrated in FIGS. 13A and 13B, the kit 400 can also include an 18 gauge needle 406 and/or a 25 gauge needle 408 operable to replace the needle 104 of the tissue marking device 100 as needed. In at least one example, the kit 400 can include a syringe 410 such as a 5 milliliter syringe with a male luer. The kit 400 can also include anesthetic 412 to numb the area where the needle 104 is to be injected into the patient. In at least one example, the anesthetic 412 can be lidocaine, and can be provided in a vial such as a 5 milliliter vial. The kit 400 can include an applicator 414. The applicator 414 can be operable to apply solution such as alcohol in preparation of surgery. For example, the applicator 414 can include an alcohol swab. In some examples, the applicator 414 can include a ChloraPrep applicator to provide, for example, a solution of 2% chlorhexidine gluconate (CHG) and 70% isopropyl alcohol (IPA). In some examples, the kit 400 can include a dressing 416 such as a film dressing to cover the puncture point from the needle 106 as well as to cover the thread 104 extending from the puncture point of the patient. For example, the dressing 416 can be Tegaderm. The kit 400 can also contain gauze 418 to help cover the puncture point. As illustrated in FIG. 13A, the dressing 416 and the gauze 418 can be separately provided. In other examples, as illustrated in FIG. 13B, the dressing 416 and the gauze 418 can be combined as one component. In some examples, the kit 400 can include a thread retention mechanism 420 operable to secure and gather excess thread 104 extending from the patient. The thread retention mechanism 420 is discussed further below in FIGS. 14-16C.

The kit 400 can include a container 402 such as a tray to contain the tissue marking device 100 and corresponding components 406-418. In some examples, as illustrated in FIGS. 13A and 13B, the container 402 can form recesses 404 operable to receive the components 406-420. The recesses 404 can be shaped and/or sized to correspond to and/or receive any or all of the components 406-420.

Figure 14:
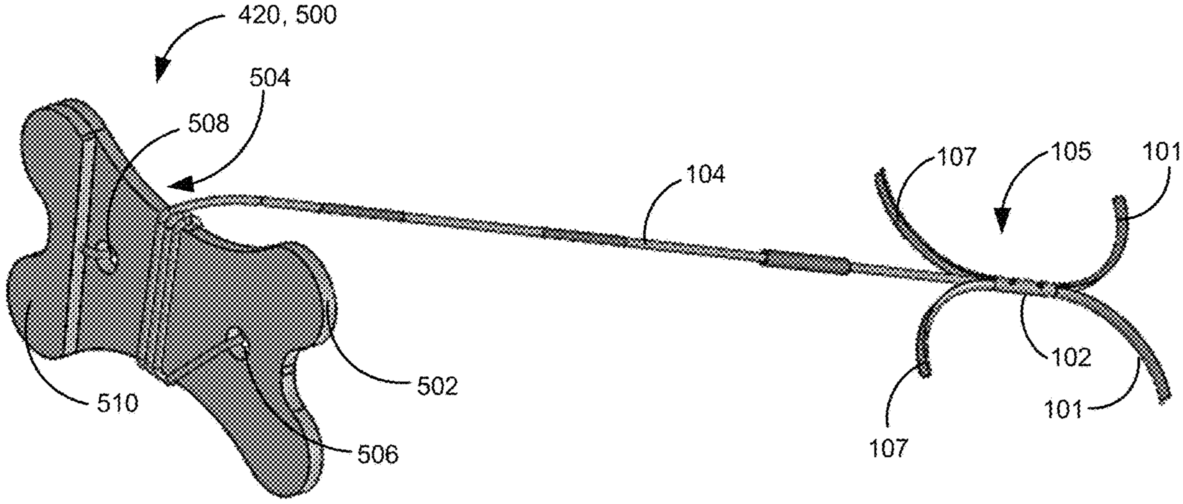
FIG. 14 is a diagram of a thread retention mechanism, according to an illustrative embodiment.

FIG. 14-16C illustrates aspects of thread retention mechanisms 420 and use thereof, according so some variations. As illustrated in FIG. 14, the thread retention mechanism 500 has a body 502 which, in at least one example, can be formed in the shape of a dog bone. In other examples, the body 502 can be formed in a substantially rectangular shape, oval shape, or any other suitable shape. The body 502 can include a waist 504 operable to receive any excess of the thread 104 extending from the patient. The thread 104 can be wrapped around the waist 504 of the body 502 as many times as desirable to control the amount of thread 104 being pressed against the tissue of the patient over an extended period of time.

The body 502 can form at least one hole 506, 508 to assist in securing the thread 104 so that the thread 104 does not easily loosen and/or release from the thread retention mechanism 500. As illustrated in FIG. 14, the hole 506 can be disposed on the opposing side of the waist 504 from the hole 508 along the longitudinal direction of the body 502. In at least one example, the thread 104 can be wrapped around the waist 504, passed through the hole 506 to one side of the body 502, and then passed through the hole 508 to the opposite side of the body 502.

Additionally, in at least one example, the thread retention mechanism 500 can secure the end of the thread 104 to prevent the end of the thread 104 from pressing against and/or poke the patient causing discomfort. By securing the thread 104, the thread 104 can be managed over the period of time before surgery, for example up to seven days in advance of surgery. As illustrated in FIG. 14, the thread retention mechanism 500 can include a flap 510 operable to fold over the body 502 and secure the end of the thread 104 such that the thread 104 does not become loose unless desired. For example, the flap 510 may include an adhesive to secure the flap 510 to the body 502 and secure the thread 104. In at least one example, the end of the thread 104 can be fed through the hole 506 to one side of the body 502, fed through hole 508 to the opposing side of the body 502, and secured by the flap 510. Then the remaining thread 104 can be wrapped around the waist 504 until the desired length of the thread 104 is achieved. For example, the thread 104 can be wrapped around the thread retention mechanism 500 until the thread retention mechanism 500 is positioned at the point of exit of the thread 104. With the thread retention mechanism 500, a user can easily secure the thread 104 without any expertise. Additionally, with the thread 104 being secured by the thread retention mechanism 500, and in some examples along with a dressing covering the thread 104, undesired movement of the hook assembly 105 after deployment in the target tissue can be minimized or prevented as the thread 104 may not be inadvertently pulled. Additionally, the likelihood of infection may be reduced. The hook assembly 105 may then remain in place for an extended period of time prior to surgery, for example up to seven days.

FIGS. 15A-15F illustrate another example of the thread retention mechanism 420. The thread retention mechanism 600 includes a body 602. The body 602, as illustrated in FIGS. 15A-15F, can have a substantially circular shape. In other examples, the body 602 can have other suitable shapes such as rectangular, triangular, or oval. In at least one example, as illustrated in FIGS. 15A-15F, the thread retention mechanism 600 can include an adhesive layer 603 operable to adhere to the patient. The adhesive layer 603 can include any suitable adhesive that is biocompatible and can maintain adherence to the patient for a period of time, for example up to seven days, until surgery. In at least one example, the adhesive layer 603 can be antimicrobial. In some examples, a cover 604 can be provided to cover the adhesive layer 603 until the thread retention mechanism 600 is ready to be applied to the patient. The cover 604 can then be removed or peeled off to expose the adhesive layer 603.

A spool 606 can extend from the body 602. The spool 606 can be operable to receive the thread 104 such that the thread 104 can be wrapped around the spool 606. The body 602 and/or the spool 606 can form an aperture 610 through which the thread 104 can be passed from below the thread retention mechanism 600. In other words, the thread 104 can be passed through the aperture 610 from the opposing side of the body 602 from the spool 606, across the body 602, and through the spool 606. The thread 104 can pass from the side of the body 602 with the adhesive layer 603 to the side of the body 602 without the adhesive layer 603.

Figure 15A:
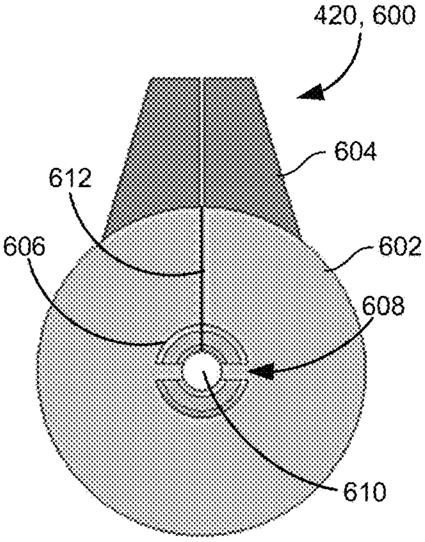
FIGS. 15A-15F are diagrams of a thread retention mechanism, according to illustrative embodiments.
Figure 15B:
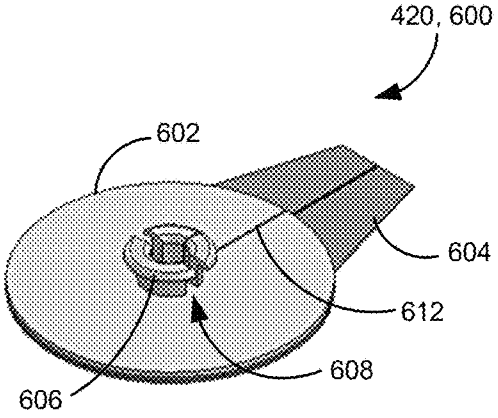
Figure 15C:
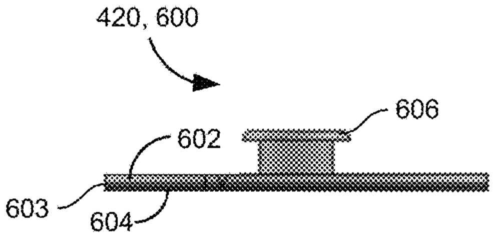
Figure 15D:
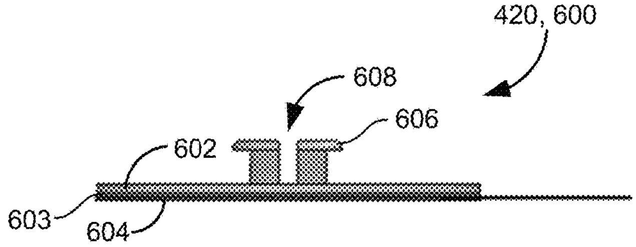
Figure 15E:
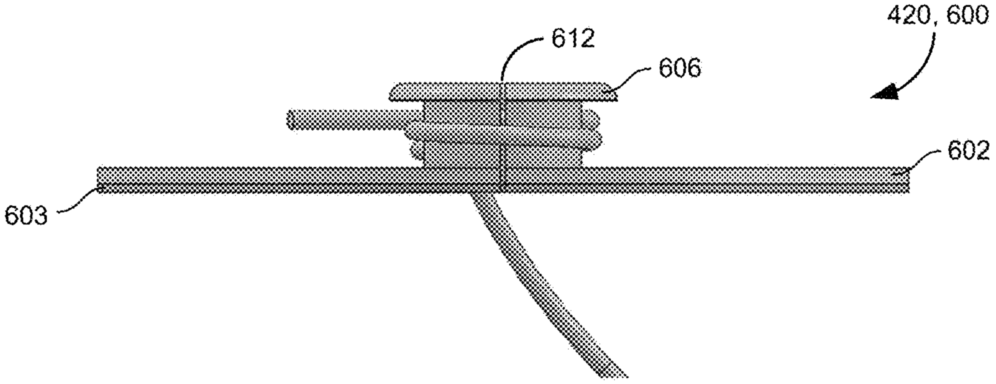
Figure 15F:
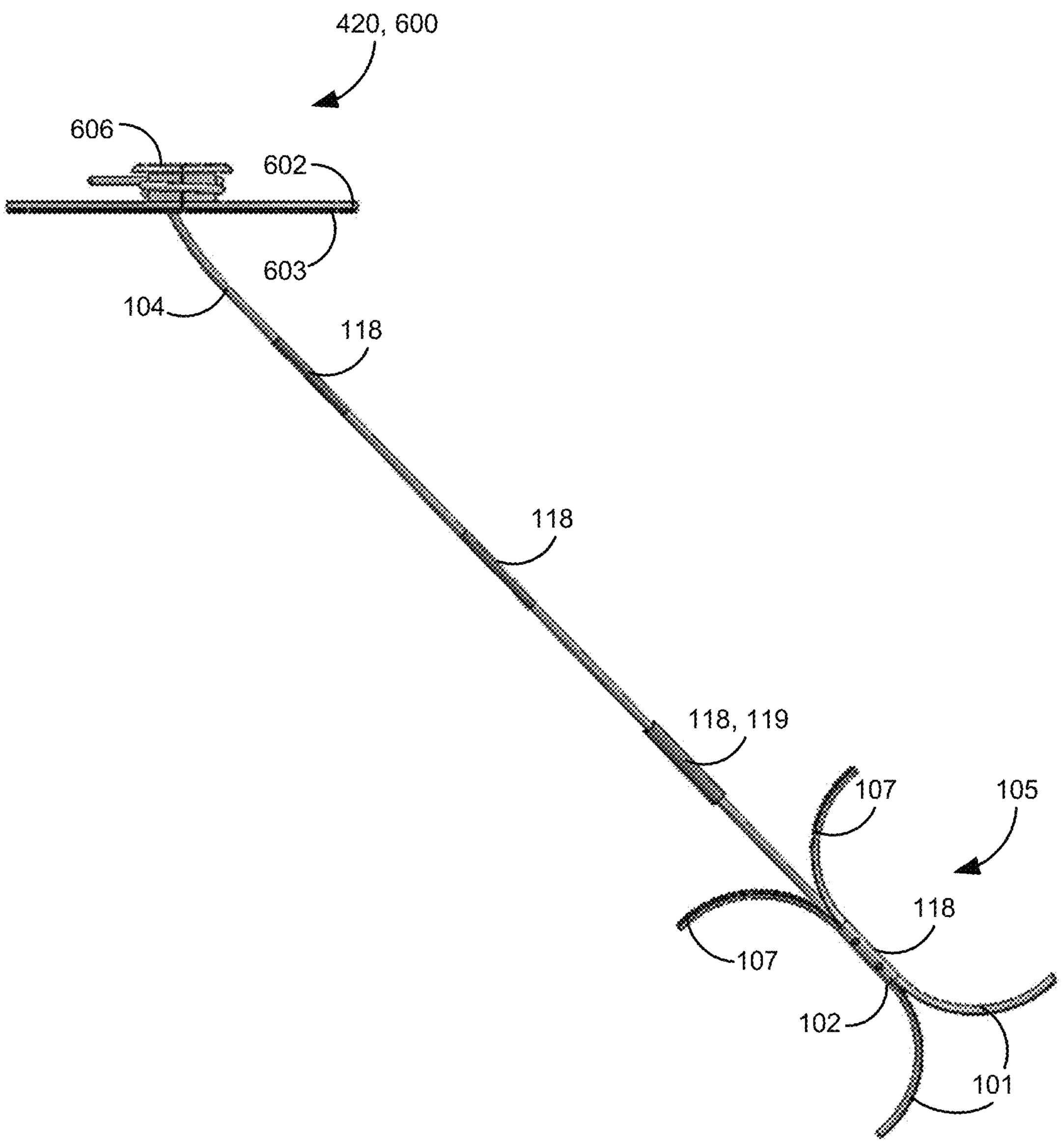

As illustrated in FIGS. 15A, 15B, and 15D, the spool 606 can form a passage 608 sized to receive the thread 104. The passage 608 can split the spool 606 into two sections. The thread 104, after passing through the aperture 610, can pass through the passage 608 in the spool 606, and the thread 104 can then be wrapped around the spool 606 until the excess thread 104 is retained. The end of the thread 104 can be passed back into the passage 608 of the spool 606 to prevent the thread from uncoiling from the spool 606. Additionally, in at least one example, the end of the thread 104 can be passed back into the passage 608 to prevent the end of the thread 104 from irritating and/or poking the patient.

As the adhesive layer 603 can be adhered to the patient, for example near the point of exit for the thread 104 from the patient, and the thread retention mechanism 420 can retain any excess thread 104, the securement process of the thread 104 can be standardized. Accordingly, the chance of infection can be reduced, and the likelihood of the thread 104 becoming loose during the period between placement and surgery is limited. Additionally, with the thread 104 being secured by the thread retention mechanism 600, and in some examples along with a dressing covering the thread 104, undesired movement of the hook assembly 105 after deployment in the target tissue can be minimized or prevented as the thread 104 may not be inadvertently pulled. The hook assembly 105 may then remain in place for an extended period of time prior to surgery, for example up to seven days.

Figure 16A:
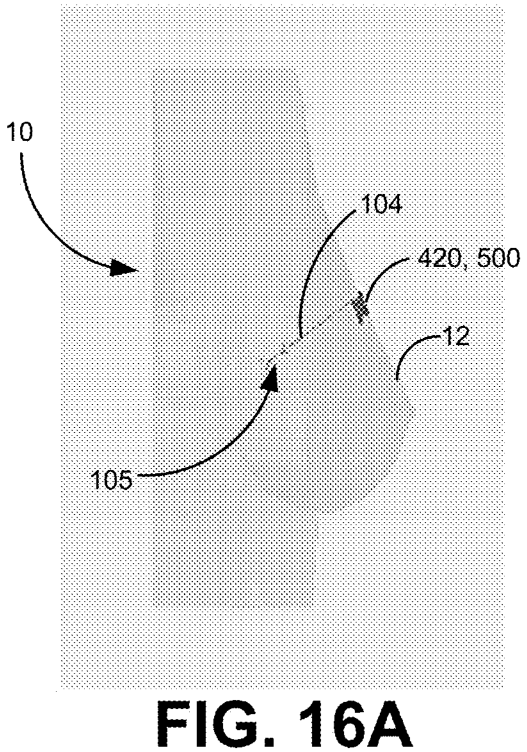
FIGS. 16A-16C are diagrams of thread retention mechanisms utilized on a patient, according to illustrative embodiments.
Figure 16B:
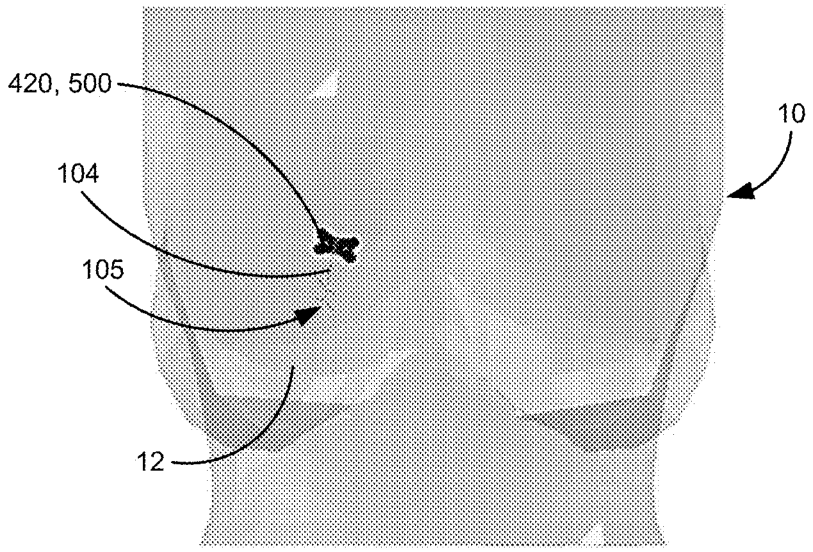
Figure 16C:
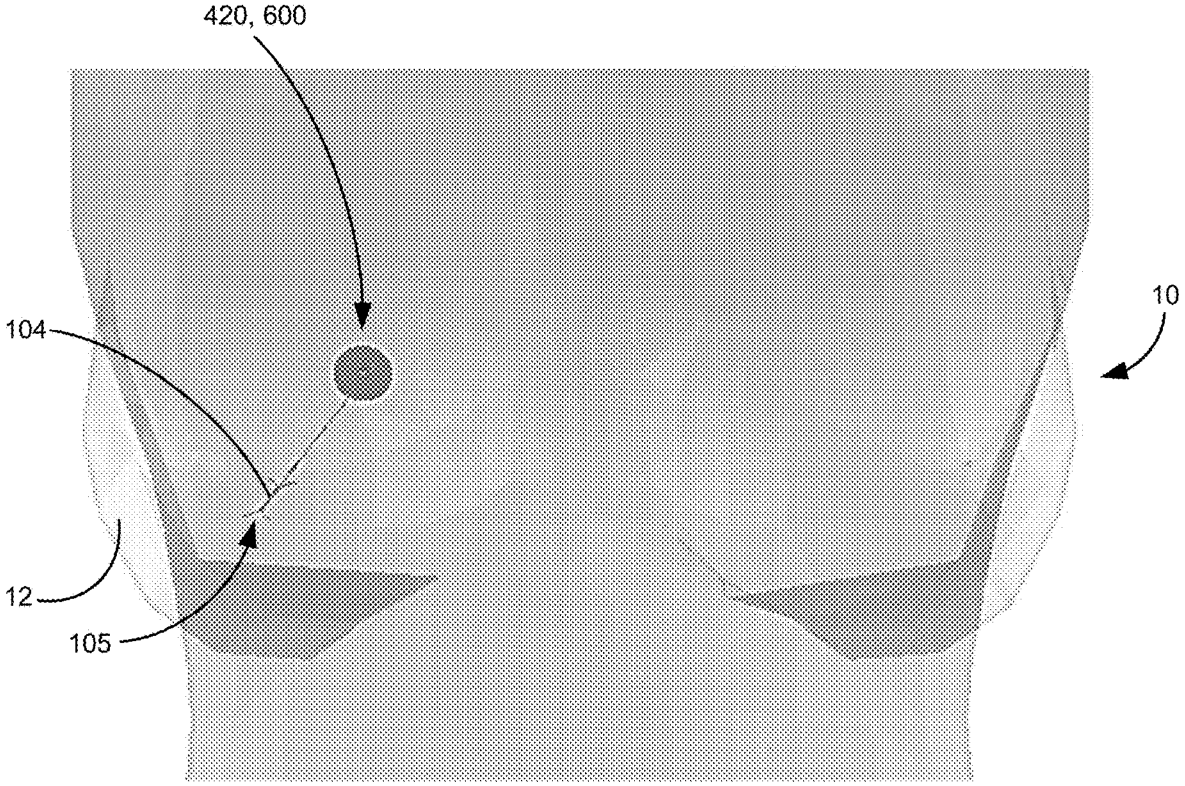

FIGS. 16A-16C illustrate hook assembly 105, the thread 104, and the thread retention mechanism 420, 500, 600 deployed within and on the patient 10. As illustrated in FIGS. 16A-16C, the hook assembly 105 is deployed and secured in the breast tissue 12 of the patient 10. In such a use, the thread 104 of the tissue marking device 100 can include breast lesion localization wire intended for use during breast lesion surgery as a guide for the surgeon to follow in the excision of the lesion. The thread 104 extends from the hook assembly 105 from within the tissue 12 to external the tissue 12. To secure any excess thread 104 as well as the end of the thread 104, the thread 104 can be wrapped around and secured by the thread retention mechanism 420, 500, 600. In at least one example, as illustrated in FIGS. 16A-16C, the thread retention mechanism 420 can secure the thread 104 at the point of exit from the tissue 12 to prevent the thread 104 from impacting daily life over the period of time prior to surgery. Additionally, the thread 104 being secured at the point of exit from the tissue 12 can prevent the thread 104 and/or the thread retention mechanism 420 from being adhered to the dressing. Accordingly, when the dressing is removed, the thread 104 is not pulled along with the dressing which could cause pain to the patient 10 and/or move the location of the hook assembly 105. For example, it is imperative to avoid moving the location of the hook assembly 105 once deployed so the tissue marking device 100 can adequately localize breast lesions and guide the surgeon to the lesion for removal.

Figure 17A:
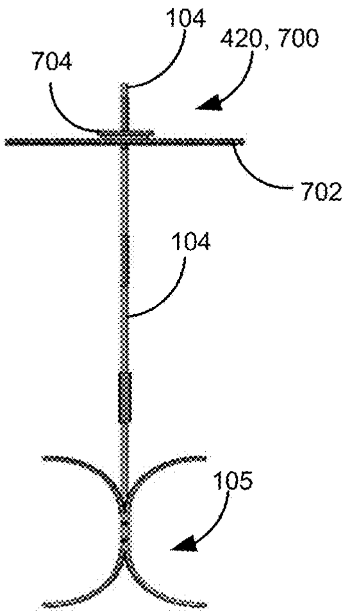
FIGS. 17A-17J are diagrams of a thread retention mechanism, according to illustrative embodiments.

FIGS. 17A-17J illustrate an example of a thread retention mechanism 420, 700. The thread retention mechanism 700, as illustrated in FIG. 17A, includes a body 702 and a thread receiving component 704 coupled with and/or extending from the body 702. After the hook assembly 105 is deployed into the patient, at least a portion of the thread 104 can be received in the thread receiving component 704. The body 702 can abut against the patient. In at least one example, the body 702 can include an adhesive component (not shown) which can adhere the body 702 of the thread retention mechanism 700 onto the patient to prevent the thread retention mechanism 700 from moving and/or pulling the thread 104 and subsequently the hook assembly 105. Accordingly, the hook assembly 105 can remain in the deployed position and placement for a period of time before surgery, for example up to between five to seven days.

In some examples, the thread 104 can be threaded through the thread receiving component 704 through an aperture or hole in the body 702 and the thread receiving component 704. In some examples, the body 702 and/or the thread receiving component 704 may include a channel through which the thread 104 can pass into the thread receiving component 704. With the channel, the thread 104 does not need to be threaded through an aperture or a hole, and can be inserted into the thread receiving component 704. In some examples, the thread 104 can be slid into the thread receiving component 704.

In at least one example, at least a portion of the thread 104 can be wrapped around the thread receiving component 704 in that the thread receiving component 704 can serve as a spool and retain any excess thread 104. In some examples, a separate spool may be provided such that at least a portion of the thread 104 can be wrapped around the spool to retain any excess thread 104.

Figure 17B:
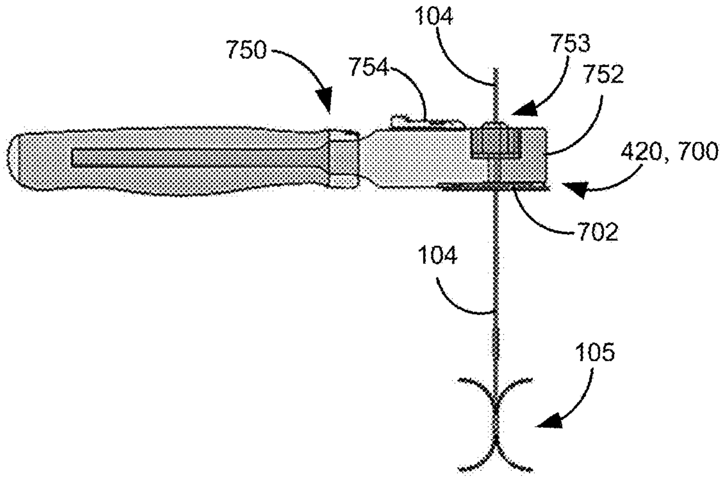
Figure 17C:
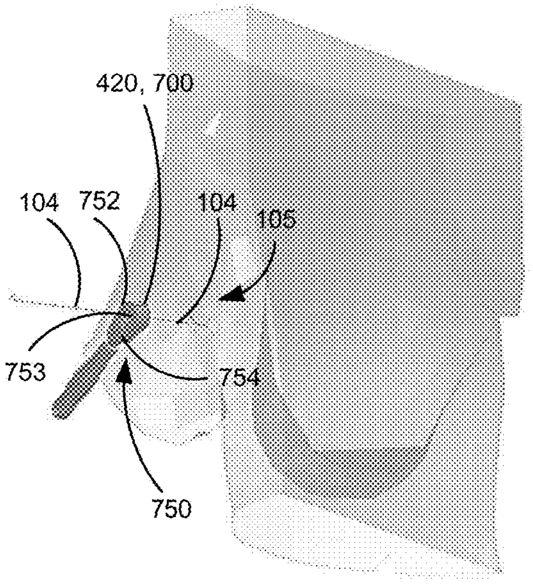

As illustrated in FIG. 17B-17F, after the thread 104 is received in the thread receiving component 704, the portion of the thread 104 disposed in the thread receiving component 704 can be secured in the thread receiving component 704. As such, the thread 104 is secured and cannot be shifted independently or removed from the thread retention mechanism 420. In some examples, as illustrated in FIG. 17B, a tool 750 can be utilized to secure the thread 104. The tool 750 can include a head 752 operable to receive at least a portion of the thread receiving component 704 and at least a portion of the excess thread 104 extending from the thread retention mechanism 700. The thread 104 can pass through a receiver 753 in the head 752. The receiver 753, in some examples, can include an aperture such that the thread 104 is threaded through the aperture. In some examples, the receiver 753 can include a channel such that the thread 104 can be slid into the receiver 753.

In at least one example, the tool 750 can secure the thread 104 in the thread retention mechanism 700 by deforming the thread receiving component 704. For example, the tool 750 may crimp the thread receiving component 704 such that the body of the thread receiving component 704 pinches the thread 104 and prevents the thread 104 from moving.

Figure 17D:
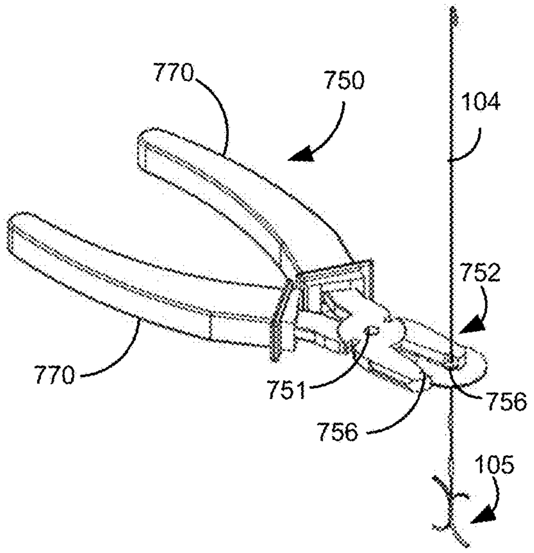
Figure 17E:
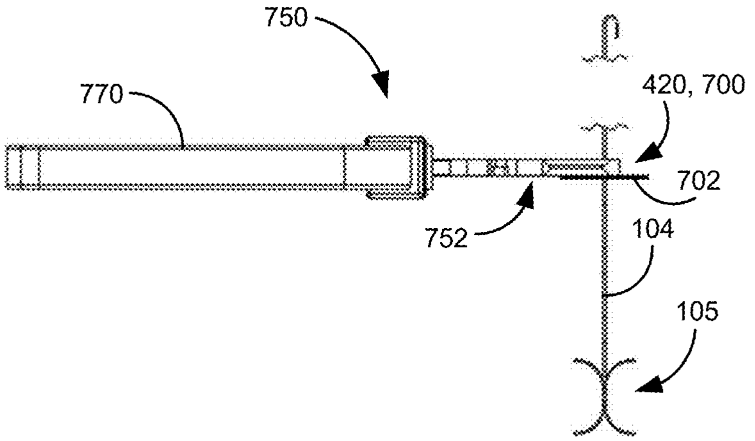
Figure 17F:
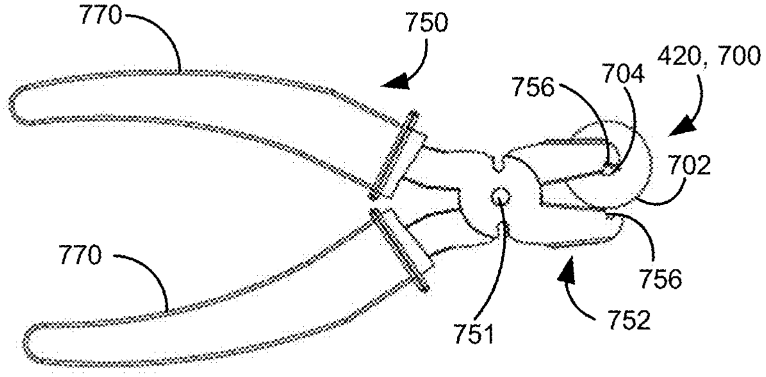

FIGS. 17D-17F illustrate an example of a tool 750 operable to secure the thread 104 in the thread retention mechanism 700 by deforming the thread receiving component 704.

As illustrated in FIGS. 17D-17F, the head 752 of the tool 750 can include a deformation portion 756 operable to receive the thread receiving component 704. In at least one example, the head 752 can include two portions which can be brought together by handle portions 770. When the handle portions 770 are brought closer together, the two portions of the head 752 also move closer together. In some examples, the tool 750 can pivot along a pivot point 751. The pivot point 751 can include a screw or a securement device which allows the head 752 and the handle portions 770 to pivot and move synchronously. In some examples, the tool 750 can be substantially similar to the form of pliers. In some examples, the tool 750 can be substantially similar to the form of wire strippers.

The deformation portion 756 can include recesses formed into each of the two portions of the head 752. The recesses of the deformation portion 756 can be substantially semi-circular such that when the two portions of the head 752 are brought together, the recesses form substantially a circle. While the deformation portion 756 as illustrated in FIGS. 17D-17F form substantially a circle, the deformation portion 756 can form any other suitable shape such as rectangular, triangular, or oval. The deformation portion 756 is sized and shaped so that when two portions of the head 752 are brought together, the deformation portion 756 abuts against the thread receiving component 704. Adding additional force to the tool 750 in bringing the two portions of the head 752 together can deform the thread receiving component 704, securing the thread 104 in the thread retention mechanism 700.

After the thread 104 is secured, in some examples, the tool 750 can be removed. The user can test that the thread 104 is secured by lightly pulling the thread retention mechanism 700 from the patient. However, to ensure that the hook assembly 105 does not move, the pulling force must be very gentle.

Figure 17G:
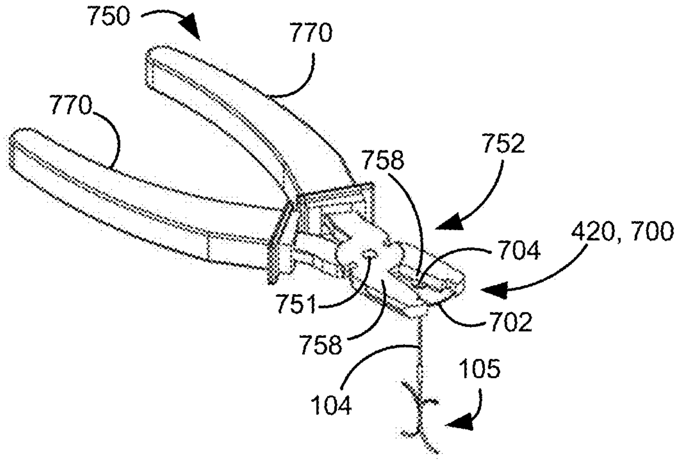
Figure 17H:
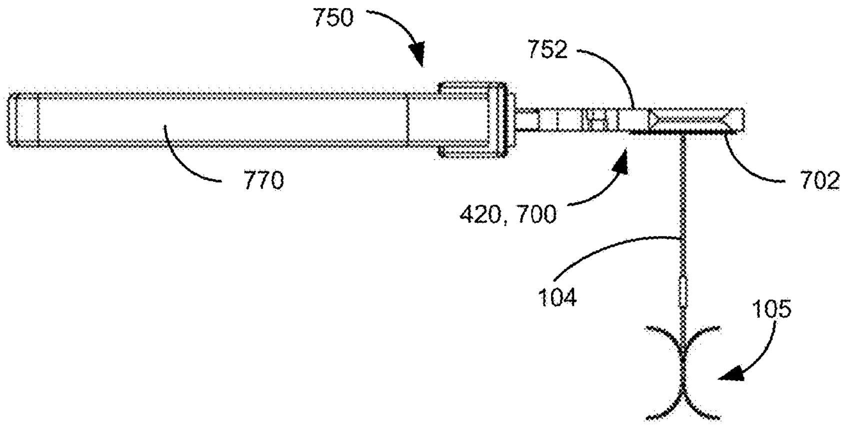
Figure 17I:
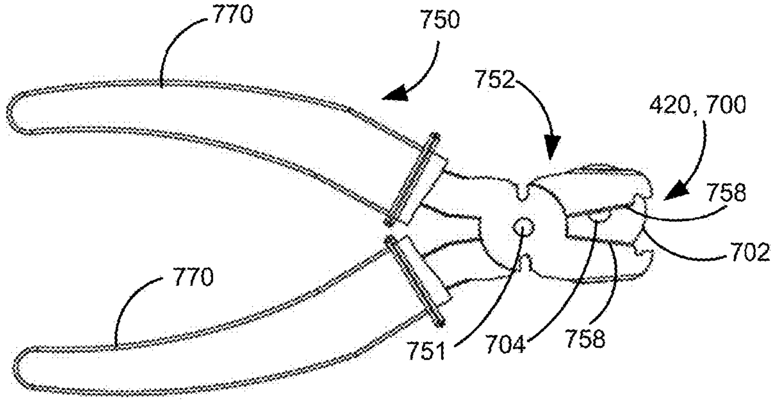

After the thread 104 is secured, the excess thread 104 can be cut so that no excess thread 104 extends from the patient. The thread 104 can be cut at the thread receiving component 704 such that little to no thread 104 extends from the thread receiving component 704 of the thread retention mechanism 700. In at least one example, the thread 104 can be cut with the same tool 750 that secured the thread 104. For example, as illustrated in FIGS. 17G-17I, the tool 750 that was used to secure the thread 104 in the thread retention mechanism 700 can also be utilized to cut the thread 104. The head 752 can include one or more blades 758. For example, as illustrated in FIGS. 17G-17I, each of the two portions of the head 752 can include a blade 758 such that when the two portions of the head 752 are brought together, the blades 758 on each portion of the head 752 also come together. In some examples, the blades 758 can be disposed proximate to the deformation portion 756 towards the handle portions 770 along the head 752. In some examples, the blades 758 can be disposed proximate to the deformation portion 756 away from the handle portions 770 along the head 752. When the blades 758 are brought together, the blades 758 can cut the thread 104. In some examples, the head 752 can be configured such that the head 752 can rest against the body 702 of the thread retention mechanism 700, and the blades 758 are positioned at a height to cut the thread 104 along the top of the thread receiving component 704. With such a configuration, the user can easily cut the thread 104 at the desired length to avoid excess thread 104.

In some examples, the thread 104 can be secured and cut with the tool 750 in one step. For example, a switch 754 can be actuated which can secure the thread 104 by deforming the thread receiving component 704 and cut the excess thread extending from the thread receiving component 704 without the need of any additional steps. In some examples, the thread 104 can be cut with a different cutting tool such as scissors, a blade, and/or any other suitable tool that can cut the thread 104.

Figure 17J:
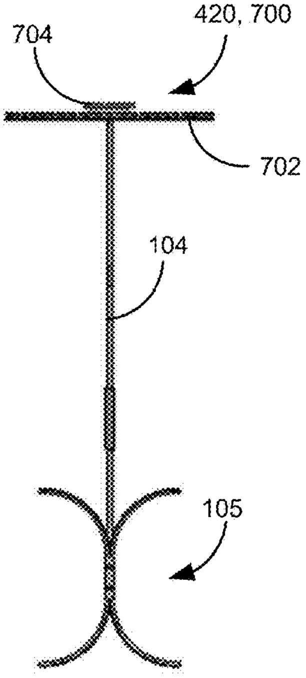

As illustrated in FIG. 17J, the thread 104 is secured in the thread receiving component 704, and the excess thread extending from the thread receiving component 704 has been cut and removed. Accordingly, there is no excess thread 104 or any components extending from the patient, and the hook assembly 105 can be comfortably deployed and in position for a period of time before surgery, for example up to seven days.

Figure 22:
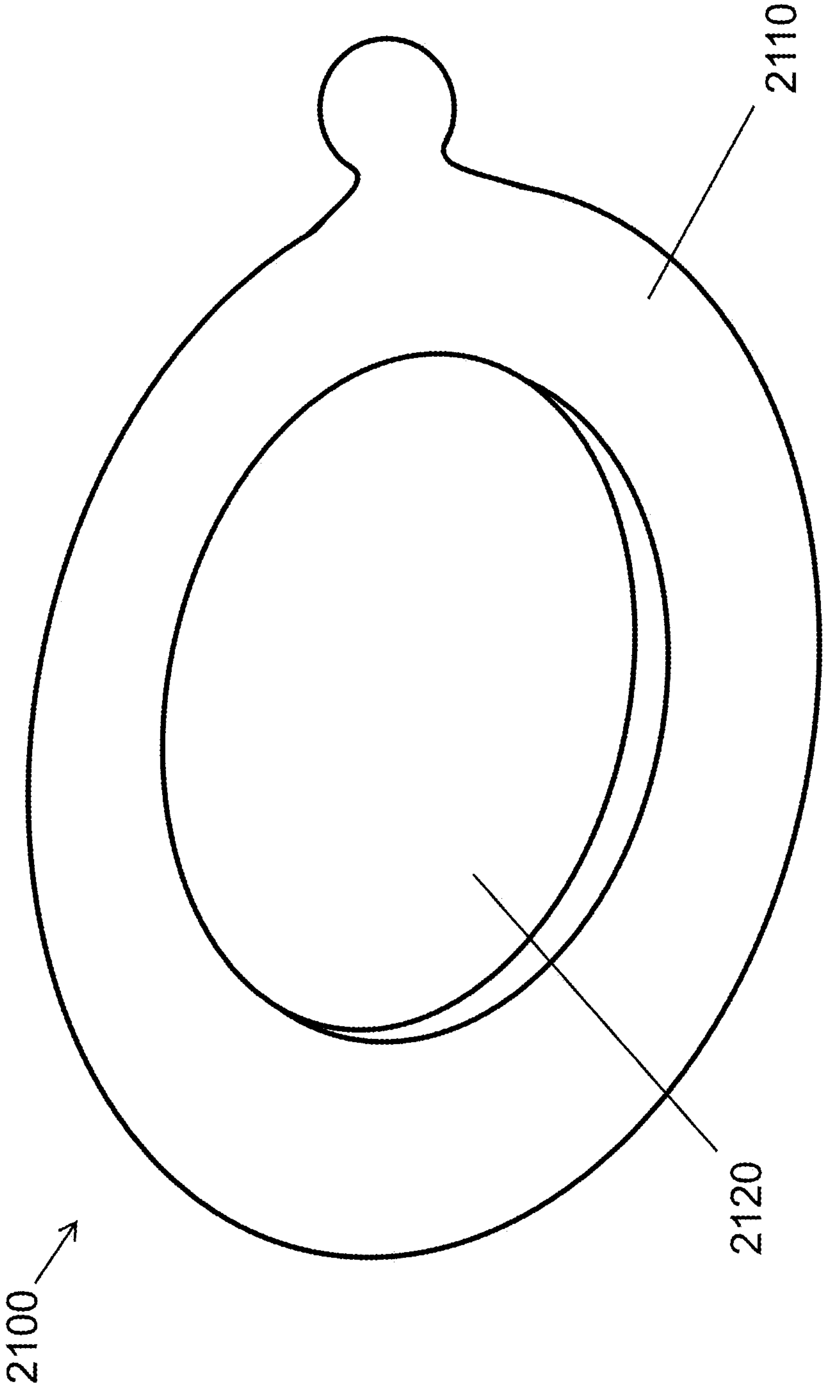
FIG. 22 is a perspective view of an adhesive thread retention mechanism, according to an illustrative embodiment.

FIG. 22 illustrates an example of a thread retention mechanism 2100. The thread retention mechanism 2100, as illustrated in FIG. 22, may include an outer portion 2110 and an inner portion 2120. After the hook assembly 105 is deployed into the patient, at least a portion of the thread 104 (e.g., a coiled portion of the thread external the patient) can be covered by the thread retention mechanism 2100. The thread retention mechanism 2100 may contain and/or retain the thread 104 against the patient. Accordingly, in variations, the thread retention mechanism 2100 may advantageously permit the hook assembly 105 to remain in the deployed position and placement for a period of time before surgery, for example up to between five to seven days.

In a variation, the thread retention mechanism 2100 may be in the form of a bandage, such as is illustrated in FIG. 22. In such a variation, the outer portion 2110 (e.g., about the perimeter) of the thread retention mechanism 2100 may include an adhesive component 2112 which can adhere the thread retention mechanism 2100 onto the patient, such as is illustrated by way of non-limiting example in FIGS. 22A-22D. The adhesive component 2112 may include an adhesive, such as a water-tight or waterproof adhesive. In such variations, the adhesive component 2112 of the outer portion 2110 can adhere the thread retention mechanism 2100 onto the patient to prevent the thread retention mechanism 2100 from moving and/or pulling the thread 104 and subsequently the hook assembly 105. In a variation, all or less than all of the outer portion 2110 of the thread retention mechanism 2100 may include the adhesive component 2112 thereon. Put another way, the adhesive component 2112 may be disposed on all or less than all of the outer portion 2110 of the thread retention mechanism 2100. The adhesive component 2112 disposed on the outer portion 2110 of the thread retention mechanism 2100 may generally include adhesive suitable for adhering to the patient's skin and for retaining the thread retention mechanism thereto.

The inner portion 2120 of the thread retention mechanism 2100 may be configured to contact the thread 104 so as to retain the thread in abutment with or proximity to the patient. In a variation, the inner portion 2120 of the thread retention mechanism 2100 may include an adhesive disposed thereon. In such a variation, the adhesive disposed on the inner portion 2120 of the thread retention mechanism 2100 may generally be configured so as to assist in maintaining the thread 104 (e.g., a coiled portion of the thread external the patient) in abutment with or proximity to the patient while also avoiding undesired over-attachment to the thread 104 that could cause moving and/or pulling of the thread 104 and subsequently the hook assembly 105 when the thread retention mechanism 2100 is removed. In variations in which the inner portion 2120 of the thread retention mechanism 2100 includes an adhesive, the adhesive present on the inner portion may generally be of lesser adhesiveness (e.g., of lesser adhesive quality and/or of lesser adhesive strength) than the adhesive present on the outer portion 2120 of the thread retention mechanism 2100. In other variations, the inner portion 2120 of the thread retention mechanism 2100 may be devoid of any adhesive, such as is illustrated by way of non-limiting example in FIGS. 22A-22D. The inner portion 2120 of the thread retention mechanism 2100 may, in variations, be tented so as to provide adequate space for the thread 104 therebeneath. Put another way, the inner portion 2120 of the thread retention mechanism 2100 may be raised above the outer portion 2110 of the thread retention mechanism, such as is illustrated by way of non-limiting example in FIG. 22.

Figure 23A:
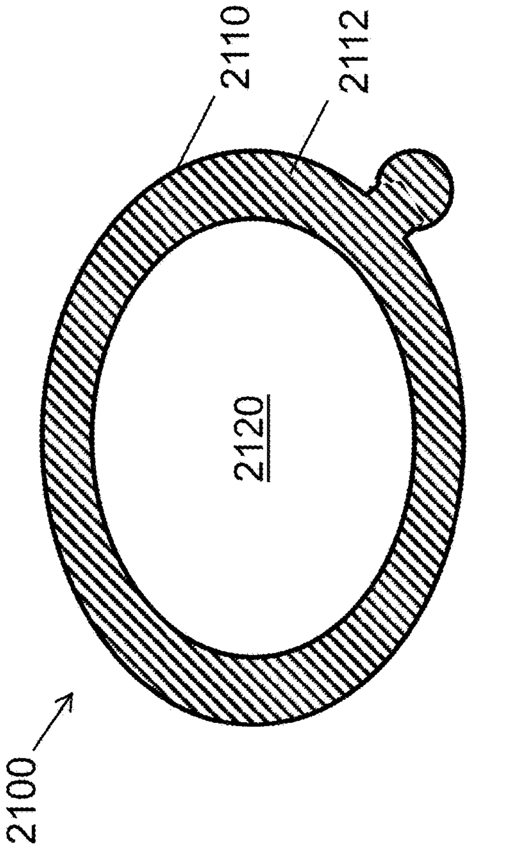
FIGS. 23A-23D are bottom views of various adhesive thread retention mechanisms, according to illustrative embodiments.
Figure 23B:
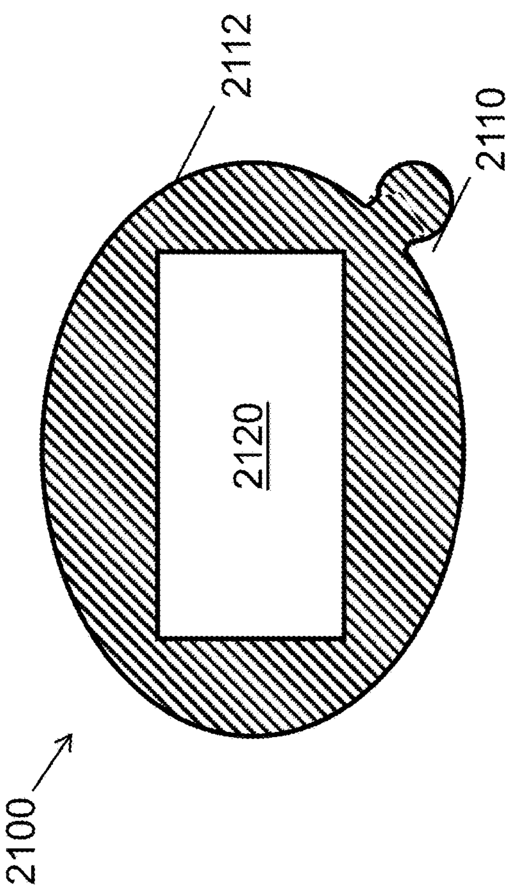
Figure 23C:
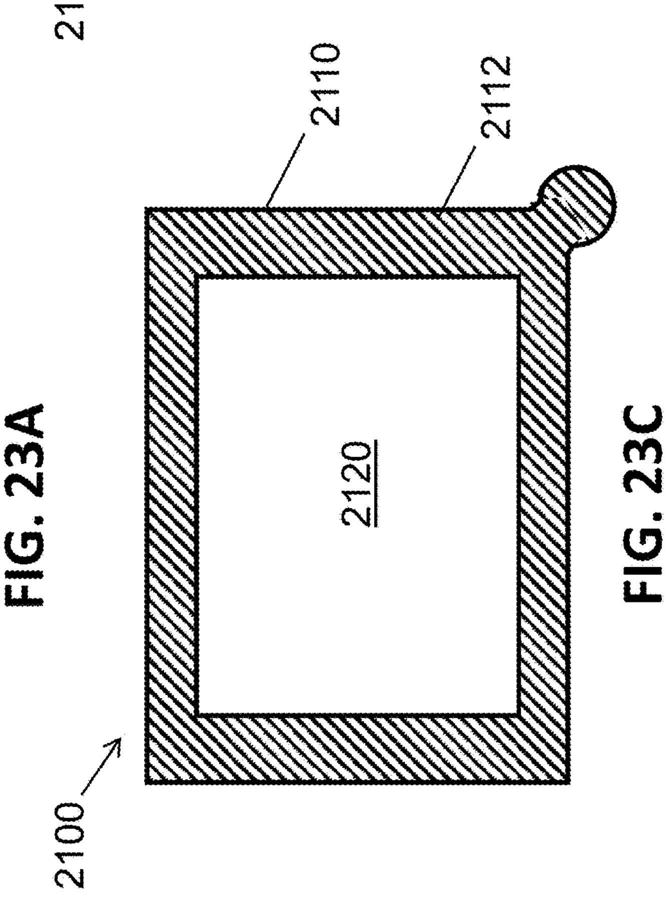
Figure 23D:
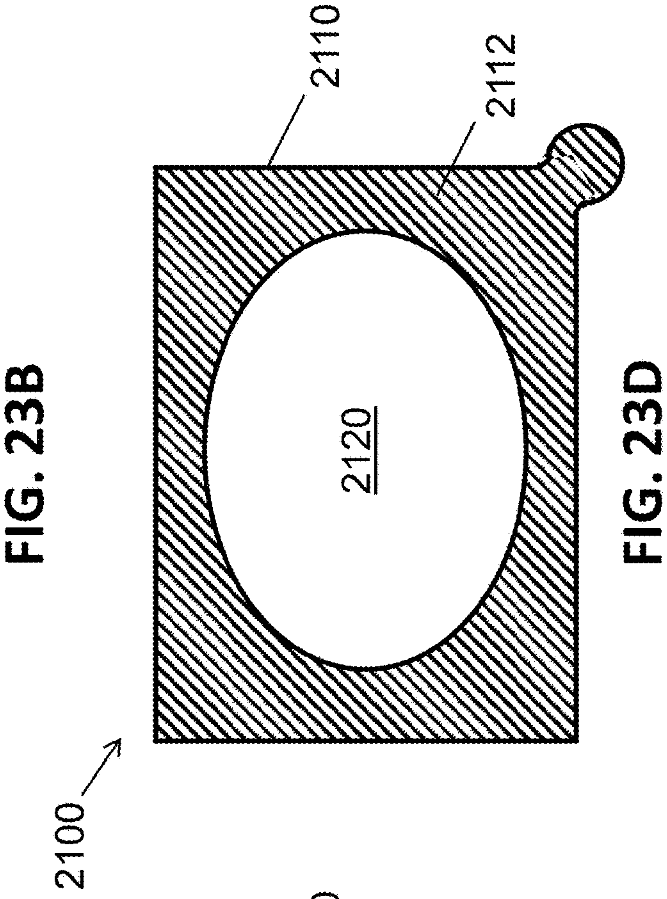

In variations in which the thread 104 is configured to coil upon itself, the thread retention mechanism 2100 may be smaller than the type of retention mechanism (e.g., 4"×4" Tegaderm patches) typically employed. By way of non-limiting example, the thread retention mechanism 2100 may have a diameter of less than or equal to 2" (e.g., a 2" circular bandage), with the outer portion 2110 having a diameter of less than or equal to 0.375" and the inner portion 2120 having a diameter of less than or equal to 1.25". The thread retention mechanism 2100 (including the inner portion 2120 and the outer portion 2110 thereof) may be of any desired shape and/or size to suit a particular application. By way of further non-limiting example, the outer portion 2110 of the thread retention mechanism 2100 may be of a generally circular shape (such as is illustrated in FIGS. 23A-B), a generally rectangular shape (such as is illustrated in FIGS. 23C-D), or any other desired shape, and the inner portion 2120 of the thread retention mechanism 2100 may be of a generally circular shape (such as is illustrated in FIG. 23A and FIG. 23D), a generally rectangular shape (such as is illustrated in FIG. 23B and FIG. 23C), or any other desired shape.

In a variation, a non-adhesive component (e.g., gauze) may be situated between the inner portion 2120 of the thread retention mechanism 2100 and the thread 104 so as to prevent direct contact between the thread and the thread retention mechanism 2100.

The below description and described figures discuss components which, individually or any combination of the components, can be incorporated and/or combined with any of the features discussed above for FIGS. 1A-23D.

Figure 24A:
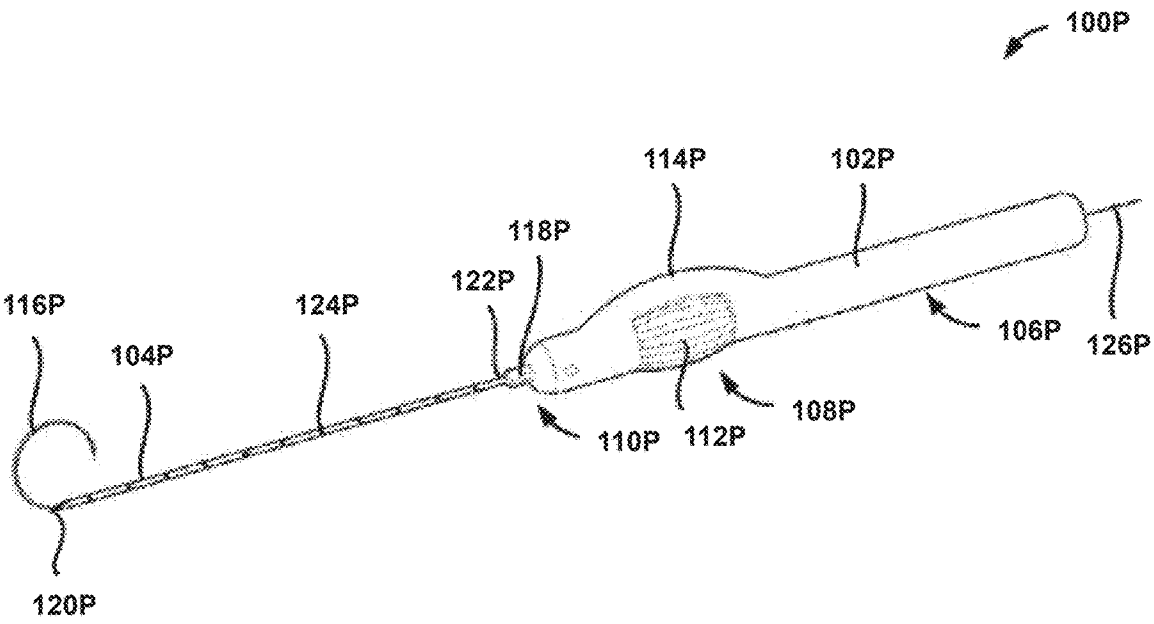
FIGS. 24A-24C, 25A-25C, 26A-26F, 27A-27F, 28A-28C, 29A-29E, 30A-30F, 31, and 32 are diagrams of components of tissue marking device(s), according to illustrative embodiments.
Figure 24B:
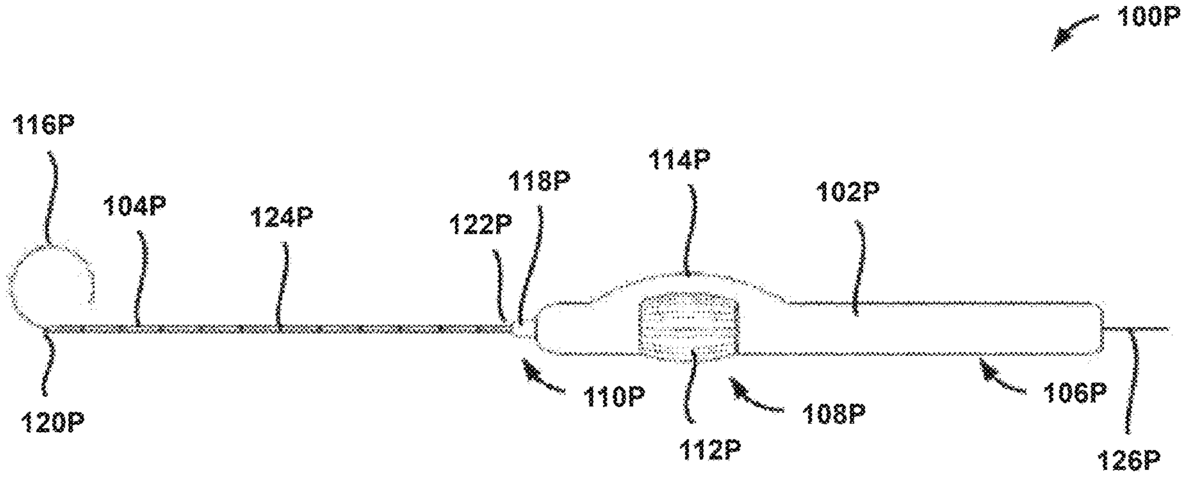
Figure 24C:
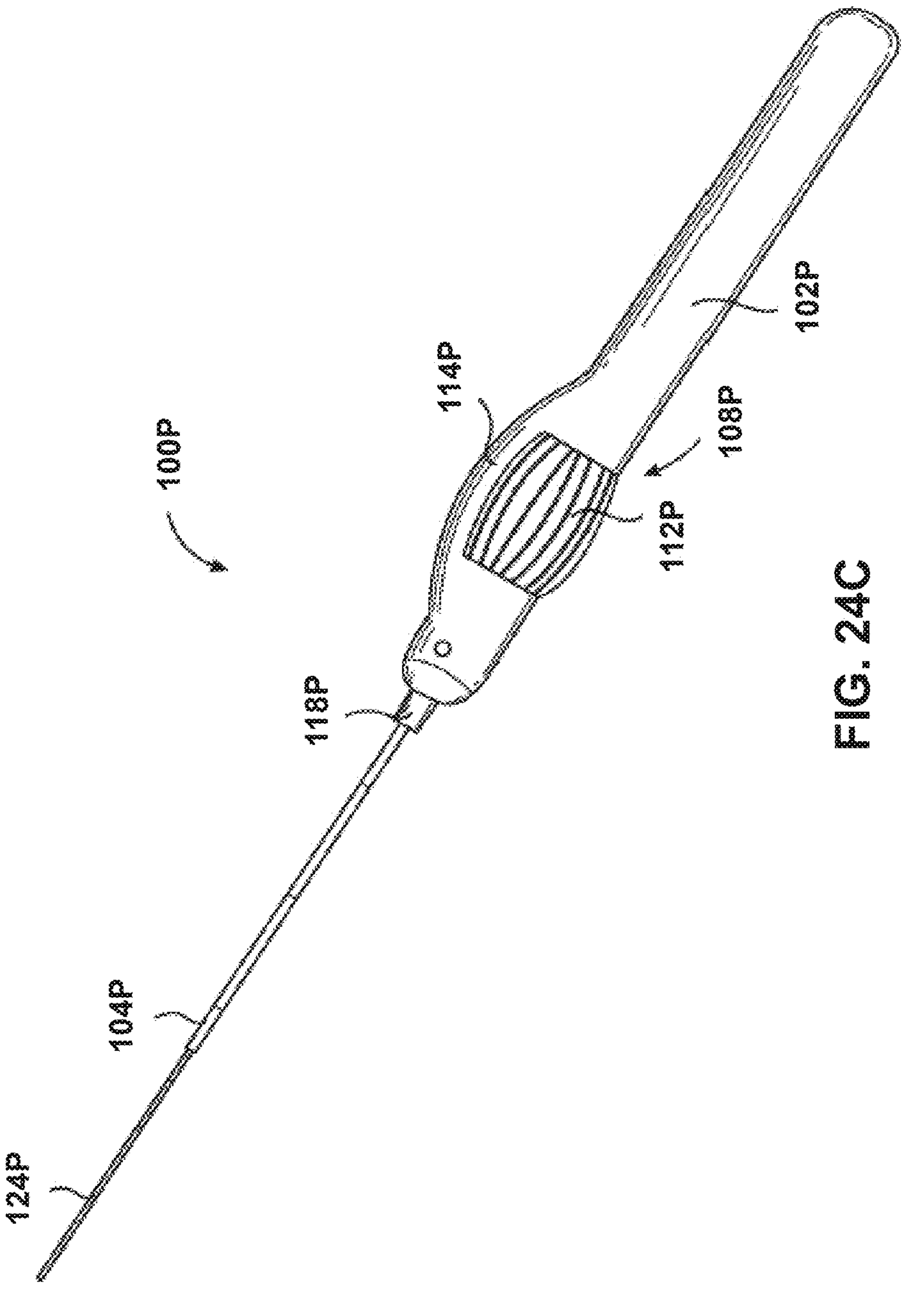

FIGS. 24A, 24B, and 24C illustrate that a tissue localization device 100P can include a handle 102P coupled to a delivery needle 104P. The handle 102P can include a handle grip 106P, a knob portion 108P, and a handle nose 110P. The handle grip 106 can be a portion of the handle 102P configured to be grasped or held by a user such as a surgeon, radiologist or other imaging professional. The handle grip 106P can be sized or shaped for a user to grasp the handle 102P with one hand. The handle grip 106P can be shaped as a cylinder, a tube, a rod, or combinations thereof. In other variations, the handle grip 106P can be shaped as an elongate ovoid, prism, ellipsoid, cone, or combinations thereof. The handle grip 106P can have finger grooves, holes, indentations, or combinations thereof.

The handle grip 106P can be connected to or contiguous with a knob portion 108P. The knob portion 108P can be a portion of the handle 102P housing a knob 112P for controlling the tissue localization device 100P. The knob portion 108P can include an orientation arch 114P. The orientation arch 114P can be a curved protuberance extending out from a surface of the handle 102P. The orientation arch 114P can help a user properly orient the tissue localization device 100P by informing the user of the deployed curvature of a localization element 116P. For example, the orientation arch 114P can have a half-oval or bow-shaped curvature denoting a direction and/or plane of curvature of the localization element 116P when deployed.

The knob 112P can be barrel or ellipsoid-shaped component for controlling the deployment or retraction of the localization element 116P. The knob 112P can be a separate component attached to the handle 102P at the knob portion 108P. The knob 112P can be positioned in proximity to the orientation arch 114P. The knob 112P can have longitudinal ridges or grooves. The longitudinal ridges or grooves of the knob 112P can allow a user to more easily rotate the knob 112P. The knob 112P can be rotated in a clockwise direction, a counterclockwise direction, or combinations thereof. The knob 112P can freely rotate until the localization element 116P is deployed out of the tissue localization device 100P. A user can hold the handle grip 106P of the handle 102P with one hand and use the fingers of the same hand to rotate the knob 112P to control the deployment or retraction of the localization element 116P.

The knob portion 108P can be connected to or contiguous with the handle nose 110P. The handle nose 110P can be a portion of the handle 102P coupled to or housing a portion of the delivery needle 104P. The handle nose 110P can include a nozzle or luer end 118P. The luer end 118P can fixedly secure a packaging needle cover tube (not shown) to the handle 102P. The luer end 118P can be cross-shaped, conical, rectangular, frustoconical, or combinations thereof.

The handle 102P, the knob 112P, or combinations thereof can be fabricated from or made of a polymer such as an injection molded polymer. For example, the handle 102P, the knob 112P, or combinations thereof can be composed of or comprise acrylonitrile butadiene styrene (ABS) plastic, polycarbonate, polypropylene (PP), or combinations thereof. The handle 102P can also be fabricated from or include parts fabricated from glass-filled polymers, metals or metal alloys such as stainless steel, or combinations thereof.

The handle 102P can have a longitudinal dimension of between 100.0 mm and 200.00 mm. For example, the handle 102P can have a longitudinal dimension of approximately 155.0 mm. When the handle grip 106P is shaped as a cylinder, the handle grip 106P can have a diameter between 9.0 mm and 13.0 mm. For example, the handle grip 106P can have a diameter of approximately 11.0 mm.

The delivery needle 104P can include a needle tip 120P and a needle base 122P. The needle tip 120P can be an end of the delivery needle 104P for puncturing the skin of a patient and deploying the localization element 116P. The delivery needle 104P can have a needle lumen. The needle lumen can be a hollow cavity within the delivery needle 104P for storing or housing the localization element 116P, a tracking wire 126P, a portion therein, or combinations thereof.

The needle tip 120P can have a beveled or deflected tip or point. The needle tip 120P can also include a blade, a sharpened edge, or a cutting edge. For example, the needle tip 120P can include a hypodermic point bevel, an intradermal point bevel, a deflected point septum, or combinations thereof. The needle tip 120P can also have a bevel angle of between 15 degrees and 45 degrees.

The needle base 122P can be partially housed or secured by the luer end 118, the handle nose 110P, other internal handle components, or combinations thereof. The delivery needle 104P can include one or more depth markers 124P in between the needle tip 120P and the needle base 122P. The depth markers 124P can be markings, etchings, or surface indentations on the surface of the delivery needle 104P in between the needle tip 120P and the needle base 122P. The depth markers 124P can assist a user, such as a surgeon, radiologist or other imaging professional, to insert the delivery needle 104P into the tissue site of the patient. The depth markers 124P can be separated by increments of millimeters, centimeters, inches, or combinations thereof.

The delivery needle 104P can be made of metal, a metal alloy such as stainless steel, or a rigid medical grade polymer. The delivery needle 104P can have a diameter of between 0.5 mm and 1.5 mm. The delivery needle 104P can have a diameter of approximately 1.0 mm.

The delivery needle 104P, for example when made from a rigid medical polymer, can include or be covered by a radiopaque material or coating. The radiopaque material or coating can include gold or gold coating, platinum or platinum coating, tungsten or tungsten coating, iridium or iridium coating, tantalum or tantalum coating, barium sulfate, rhodium, or combinations thereof.

The delivery needle can have an echogenic surface such as can be generated by sandblasting or beadblasting on portions of the needle, such as at the distal tip, for example, to enhance visualization of the needle or portions thereof during clinical ultrasound imaging.

FIGS. 24A and 24B illustrate that the localization element 116P can be curved or loop-shaped when deployed. The localization element 116P can be a flexible wire or length of metal, polymer, or combinations thereof combinations thereof. The localization element 116P can take on an arcuate, curvilinear, or looping shape when deployed out of the delivery needle 104P. The localization element 116P can penetrate tissue and serve as a boundary or guidance marker for a tissue mass for subsequent removal and/or analysis.

FIGS. 24A and 24B also illustrate that the tissue localization device 100 can include a tracking wire 126P. The tracking wire 126P can be coupled or connected to the localization element 116P. The tracking wire 126P can be made of metal, a metal alloy such as stainless steel, or a medical grade polymer, a stainless steel cable with polymer jacketing, a polymer thread, a polymer tube, or combinations thereof. The tracking wire 126P can include or be covered by a radiopaque material, for example, for enhanced visualization of the tracking wire 126 when imaged.

The tracking wire 126P can be used to track the deployment or insertion path of the delivery needle 104P, the localization element 116P, or combinations thereof combinations thereof into the patient. The tracking wire 126P, or a portion therein, can be housed within the handle 102P when the localization element 116P is not deployed or not fully deployed. A segment of the tracking wire 126P can also be located outside the handle 102P when the localization element 116P is not deployed or not fully deployed. For example, a segment of the tracking wire 126P can extend out of an end of the handle 102P proximate to the handle grip 106P when the localization element 116P is not deployed or not fully deployed.

Figure 25A:
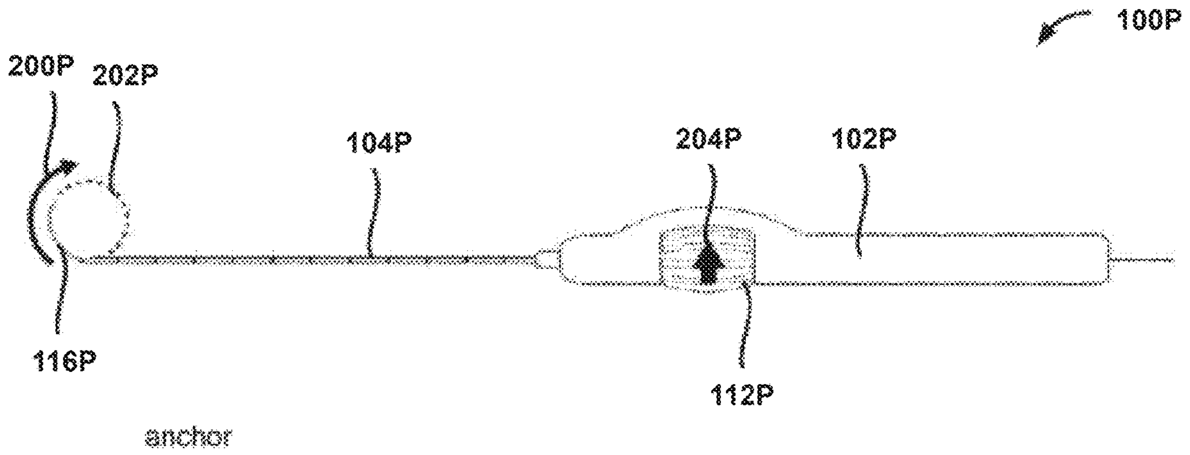

FIG. 25A illustrates that the localization element 116P can have a deployment trajectory 200P when deployed from the delivery needle 104P. The deployment trajectory 200P can include a substantially two-dimensional or planar trajectory along a substantially two-dimensional plane. For example, the deployment trajectory 200P can include a substantially two-dimensional trajectory along a plane bisecting a longitudinal axis of the tissue localization device 100P. In other variations, the deployment trajectory 200P can include a three-dimensional trajectory.

The localization element 116P can follow its deployment trajectory 200P to achieve a predetermined shape 202P. The predetermined shape 202P can include a circular shape, an oval, a spiral shape, or combinations thereof combinations thereof. In other variations, the predetermined shape 202P can include a triangular shape, a rectangular shape, a trapezoidal shape, or combinations thereof combinations thereof. The deployment trajectory 200P can be a trajectory or path mimicking or following such a predetermined shape 202P. For example, the localization element 116P can have the predetermined shape 202P of a two-dimensional circle and the localization element 116P can emerge from the delivery needle 104P in a circular trajectory.

For example, the localization element 116P can have predetermined shape 202P of a circle or loop having a diameter of between 10.0 to 40.0 mm. The localization element 116P can have a predetermined shape 202P of a circle or loop having a diameter of approximately 25.0 mm.

FIG. 25A illustrates that the localization element 116P can be deployed from the delivery needle 104P when the knob 112P is turned in a first rotational direction 204P. The first rotational direction 204P can include a clockwise rotational direction or a counterclockwise rotational direction when viewed along the longitudinal axis of the tissue localization device 100P from the handle grip 106P to the handle nose 110P.

For example, the localization element 116P can exit or emerge out of the needle tip 120P of the delivery needle 104P when the knob 112P is turned in the first rotational direction 204P. The localization element 116P can exit or emerge out of the needle tip 120P in a reverse loop trajectory representing the deployment trajectory 200P of the localization element 116P. The reverse loop trajectory can be a substantially circular trajectory curving backward toward the needle base 122P of the delivery needle 104P. The localization element 116P can initially curve upward or in a direction toward the apex or top of the orientation arch 114P before looping backwards toward the needle base 122P. In other variations, the localization element 116P can initially curve downward or in a direction away from the apex or top of the orientation arch 114P before looping backwards toward the needle base 122P.

Figure 25B:
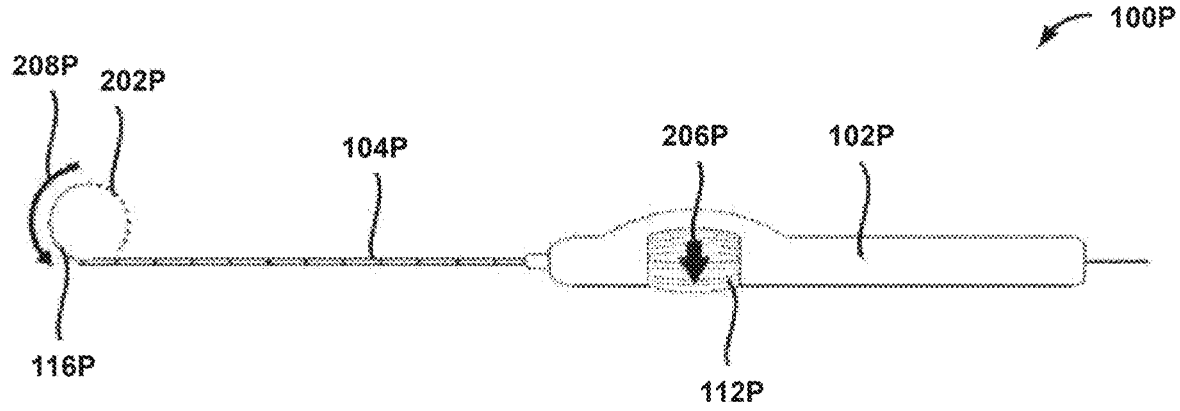

FIG. 25B illustrates that the localization element 116P can be retracted into the delivery needle 104P when the knob 112P is turned in a second rotational direction 206P. The second rotational direction 208P can be a different rotational direction than the first rotational direction 204P. The second rational direction can include a counterclockwise rotational direction or a clockwise rotational direction when viewed along the longitudinal axis of the tissue localization device 100P from the handle grip 106P to the handle nose 110P.

The localization element 116P can have a retraction trajectory 208P when retracting back into the delivery needle 104P. The retraction trajectory 208P can be the reverse or opposite of the deployment trajectory 200P. For example, when the deployment trajectory 200P is an upward curving loop trajectory as shown in FIG. 25A, the retraction trajectory 208P is a downward curving loop trajectory as shown in FIG. 25B. The retraction trajectory 208P can be a substantially two-dimensional trajectory, a three-dimensional trajectory, or combinations thereof combinations thereof.

The localization element 116P can re-enter or retract back into the needle tip 120P of the delivery needle 104P when the knob 112P is turned in the second rotational direction 208P. The localization element 116P can re-enter or retract back into the needle tip 120P by reversing or retracing the deployment trajectory 200P of the localization element 116P.

Figure 25C:
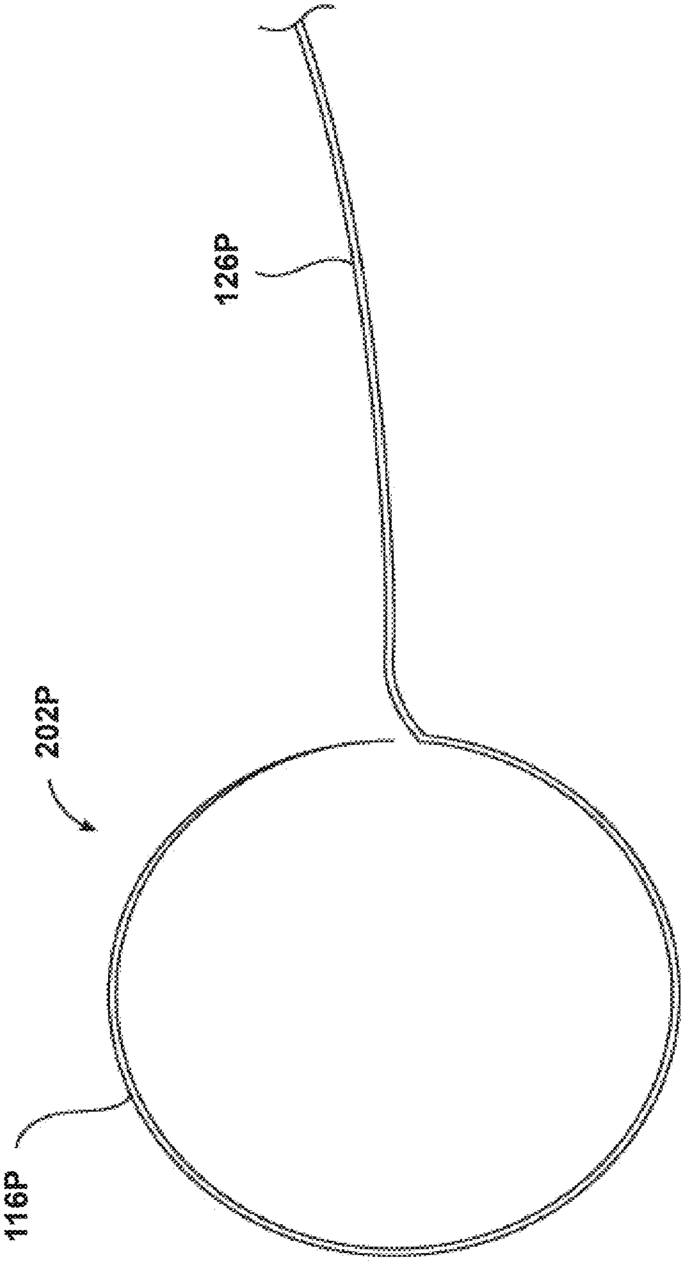

FIG. 25C illustrates that the localization element 116P can be in a circular shape representing the predetermined shape 202P. The localization element 116P can have a predetermined shape 20P2 set by using shape memory techniques, heating techniques, bending techniques, or combinations thereof combinations thereof. The localization element 116P can be composed of or fabricated from spring steel, a nickel-titanium alloy such as Nitinol™, a shape memory polymer, stainless steel, or combinations thereof combinations thereof.

The localization element 116P can include or be covered by a radiopaque material or coating. The radiopaque material or coating can include gold or gold coating, platinum or platinum coating, tungsten or tungsten coating, iridium or iridium coating, tantalum or tantalum coating, barium sulfate, rhodium, hydrophilic and other lubricious coatings, or combinations thereof.

Figure 26A:
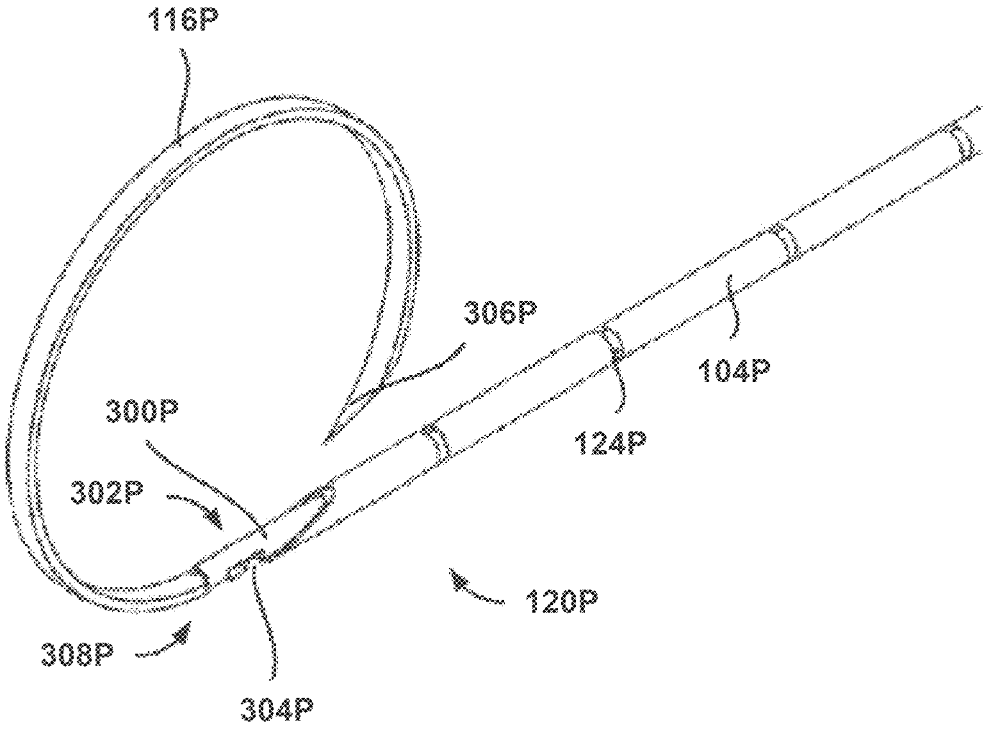

FIG. 26A illustrates that the tissue localization device 100P can include a pusher element or pusher element 300P. The pusher element 300P can be used by the tissue localization device 100P to deploy the localization element 116P. The pusher element 300P can be positioned inside the delivery needle 104P when the localization element 116P resides in the delivery needle 104P. The pusher element 300P can slidably move longitudinally within the delivery needle 104P. The pusher element 300P can be advanced longitudinally forward or longitudinally backward through the delivery needle 104P when a user turns the knob 112P in the first rotational direction 204P or the second rotational direction 208P, respectively. The pusher element 300P can be composed of or fabricated from a polymer, stainless steel, or combinations thereof.

The pusher element 300P can include a pusher tip 302P. The pusher tip 302P can be a portion of the pusher element 300P removeably attached to the localization element 116P. The pusher tip 302P can have a window 304P. The window 304P can be a partial opening or cutaway section along the pusher tip 302P.

The localization element 116P can include an element base 308P and an element tip 306P. The element base 308P can be a portion of the localization element 116P configured to be removeably attached to the pusher element 300P. The element tip 306P can be an end of the localization element 116P distal to the element base 308P. The element tip 306P can be configured to pierce or cut through patient tissue. The element tip 306P can have a beveled edge, a sharpened edge, a pointed tip, or combinations thereof.

Figure 26B:
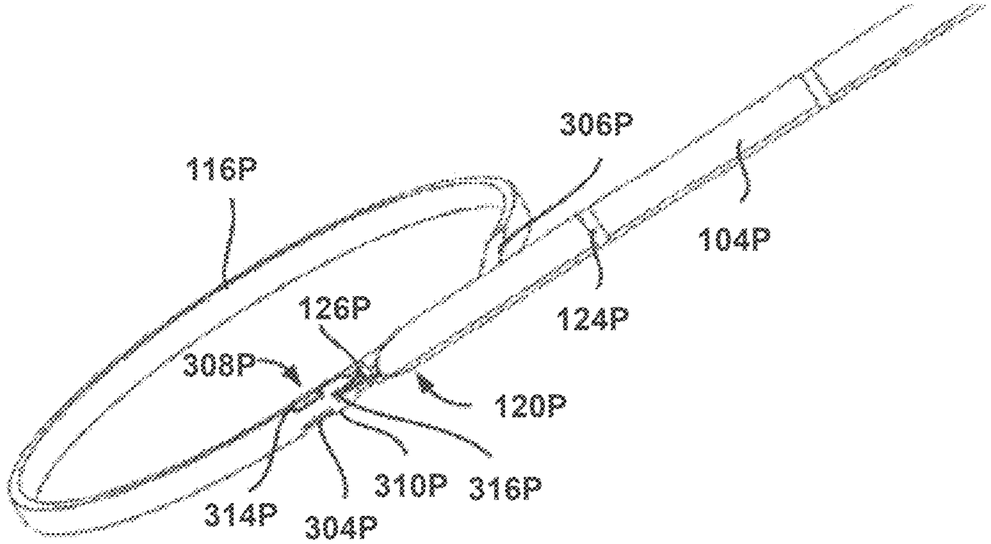

FIG. 26B illustrates that the element base 308P of the localization element 116P can include an eyelet frame 310P, a narrow portion 312P, and a shoulder 314P. The eyelet frame 310P can be connected to the shoulder 314P by the narrow portion 312P. The eyelet frame 310P can have an eyelet 316P. The eyelet 316P can be an opening or bore configured to receive the tracking wire 126P. The tracking wire 126P can be threaded through the eyelet 316P and the threaded end can be connected, for example by crimping via a ferrule or tied, to the remainder of the tracking wire 126P using a crimp sleeve, a tie, a knot, an adhesive, a coil, heat shrink polymer jacketing, or combinations thereof.

The eyelet frame 310P can fit within the window 304P of the pusher element 300P to allow the pusher element 300P to engage with the localization element 116P. The portion of the pusher element 300P distal to the window 304P can partially surround the narrow portion 312P of the element base 308P when the eyelet frame 310P is within the window 304P.

FIG. 26B illustrates that the pusher element 300P can advance the localization element 116P out of the delivery needle 104P by pushing on the shoulder 314P of the localization element 116P. The pusher element 300P can also retract or draw the localization element 116P into the delivery needle 104P by pulling on the eyelet frame 310P. The pusher element 300P can retract the localization element 116P back into the delivery needle 104P as long as the eyelet frame 310P, the narrow portion 312P, or combinations thereof do not disengage from the pusher tip 302P of the pusher element 300P. The eyelet frame 310P can disengage from the pusher tip 302P when the eyelet frame 310P is displaced out of the window 304P of the pusher element 300P. The narrow portion 312P can disengage from the pusher tip 302P when the narrow portion 312P and eyelet frame 310P are no longer surrounded by the distal portion of the pusher element 300P. When the localization element resides within tissue, the shape memory of the localization element causes the proximal portion of the localization element to pull away from the pusher tip 302P once the narrow portion 312P and eyelet frame 310 are no longer constrained by the pusher element 300P.

Figure 26C:
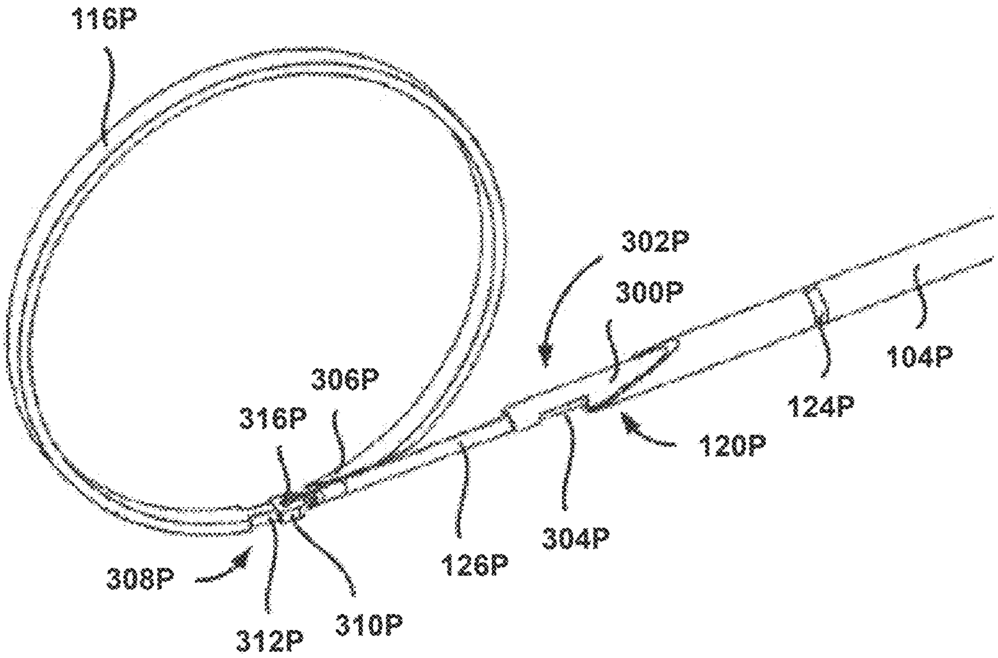
Figure 26D:
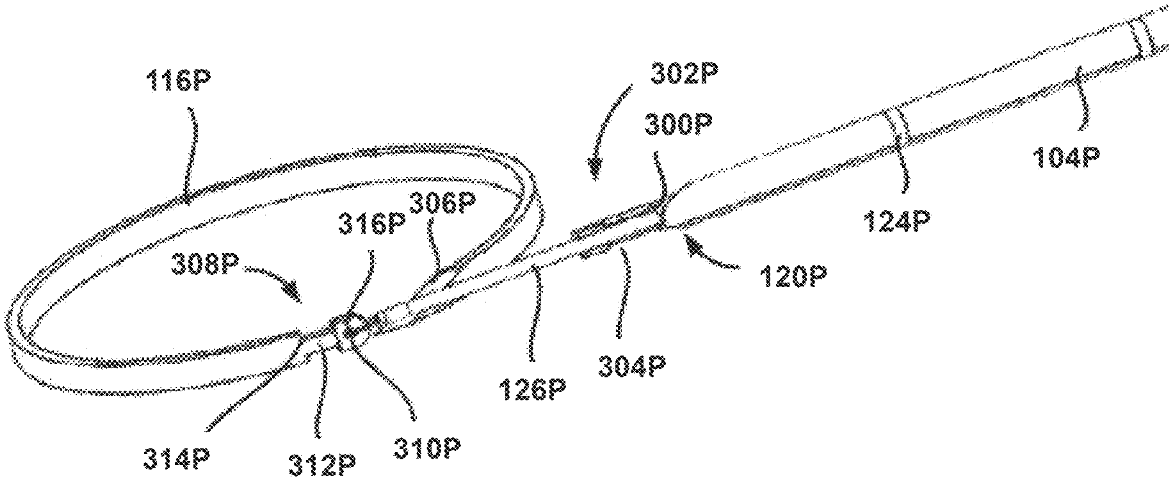
Figure 26E:
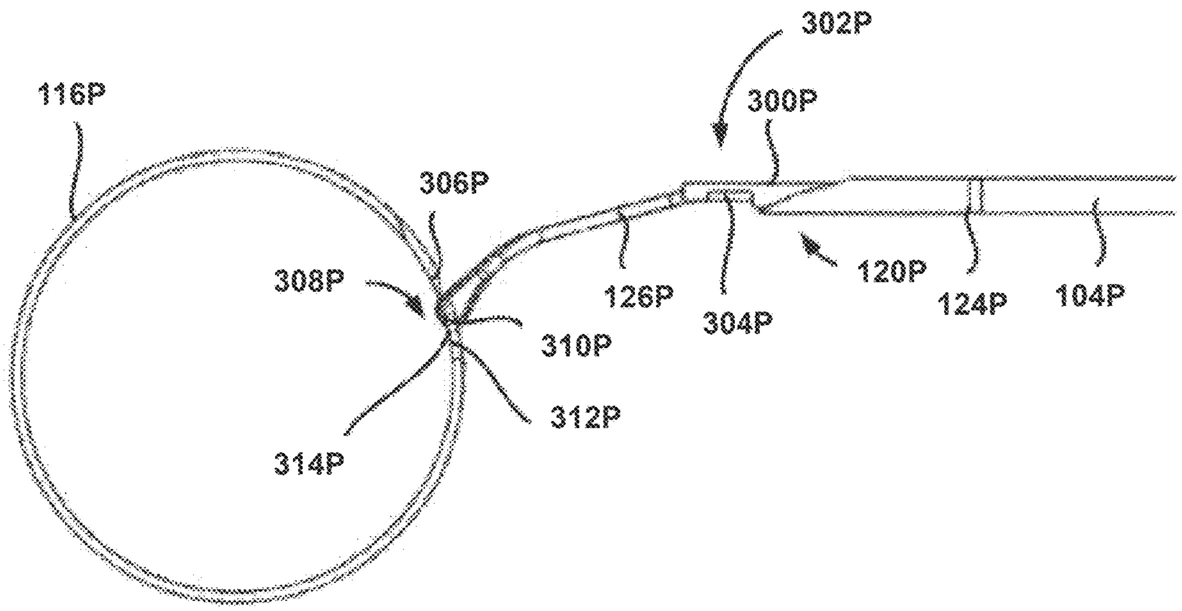
Figure 26F:
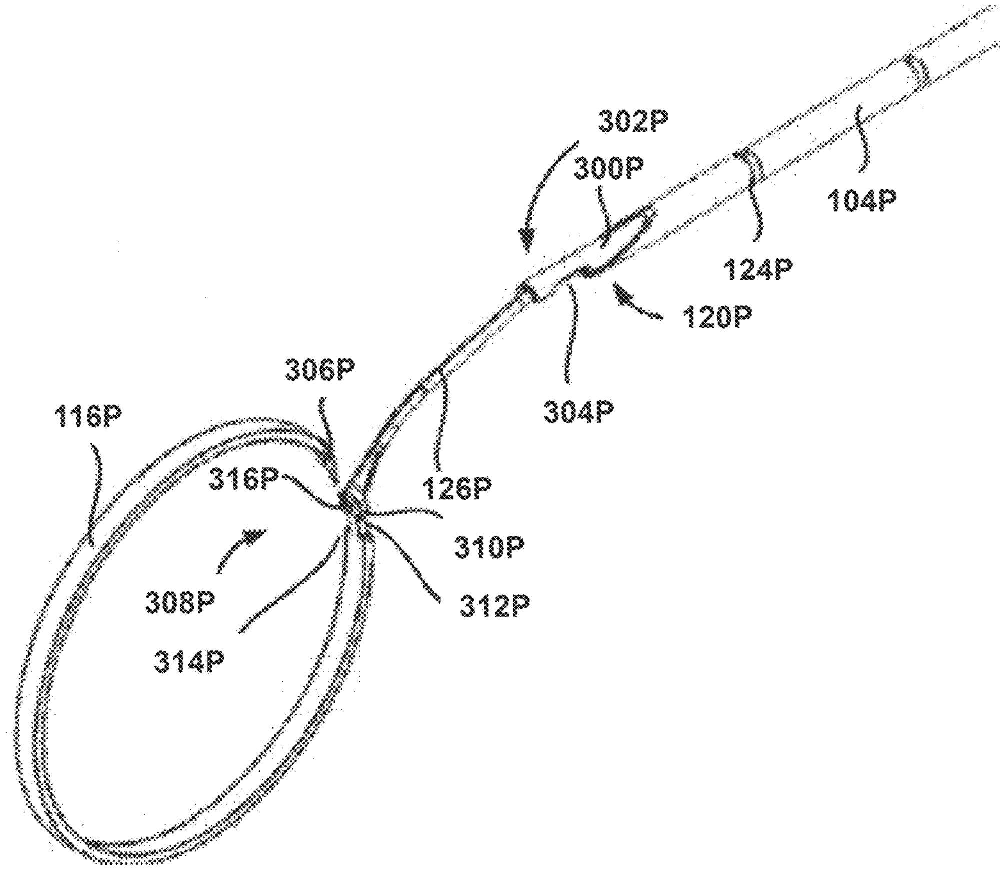

FIGS. 26C-26F illustrate that the localization element 116P can be deployed when the pusher tip 302P of the pusher element 300P no longer engages with the element base 308P. FIGS. 26C and 26D also illustrate that the tracking wire 126P can be pulled through the pusher element 300P, the delivery needle 104P, or combinations thereof once the localization element 116P is deployed. The tracking wire 126P can be pulled through the pusher element 300P, the delivery needle 104P, or combinations thereof when the user retracts the delivery needle 104P out of the patient after the localization element 116P is deployed. The entire length of the tracking wire 126P can be pulled through the handle 102P, the delivery needle 104P, the pusher element 300P, or combinations thereof once the user has fully retracted the delivery needle 104P out of the patient.

Figure 27A:
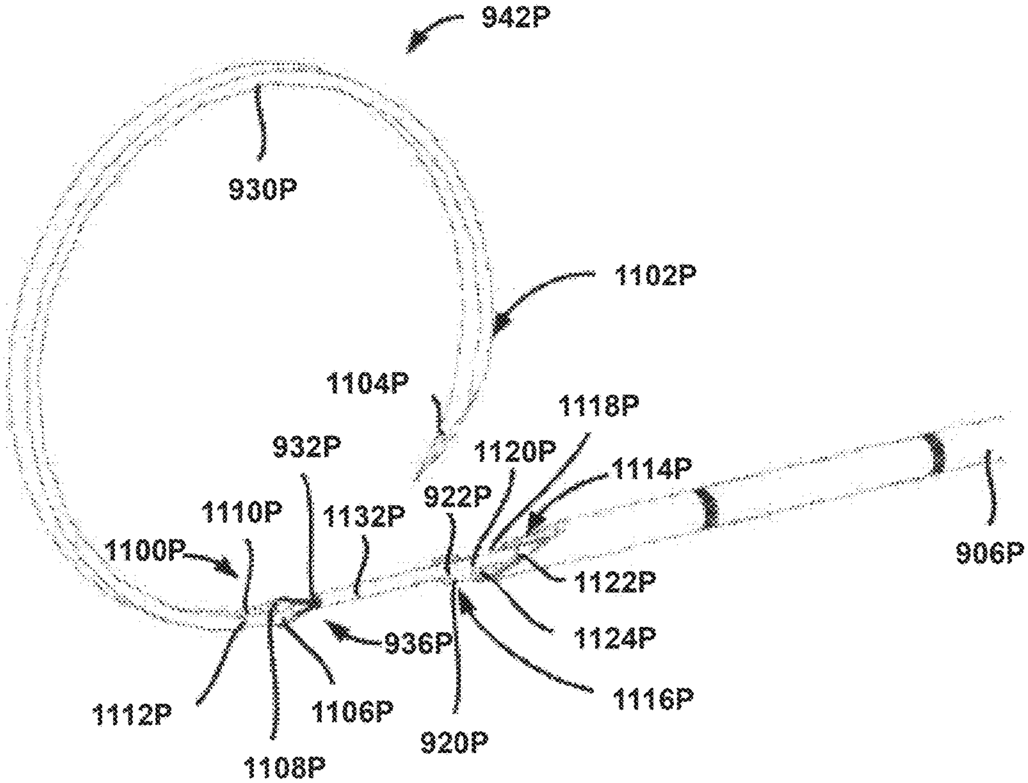
Figure 27B:
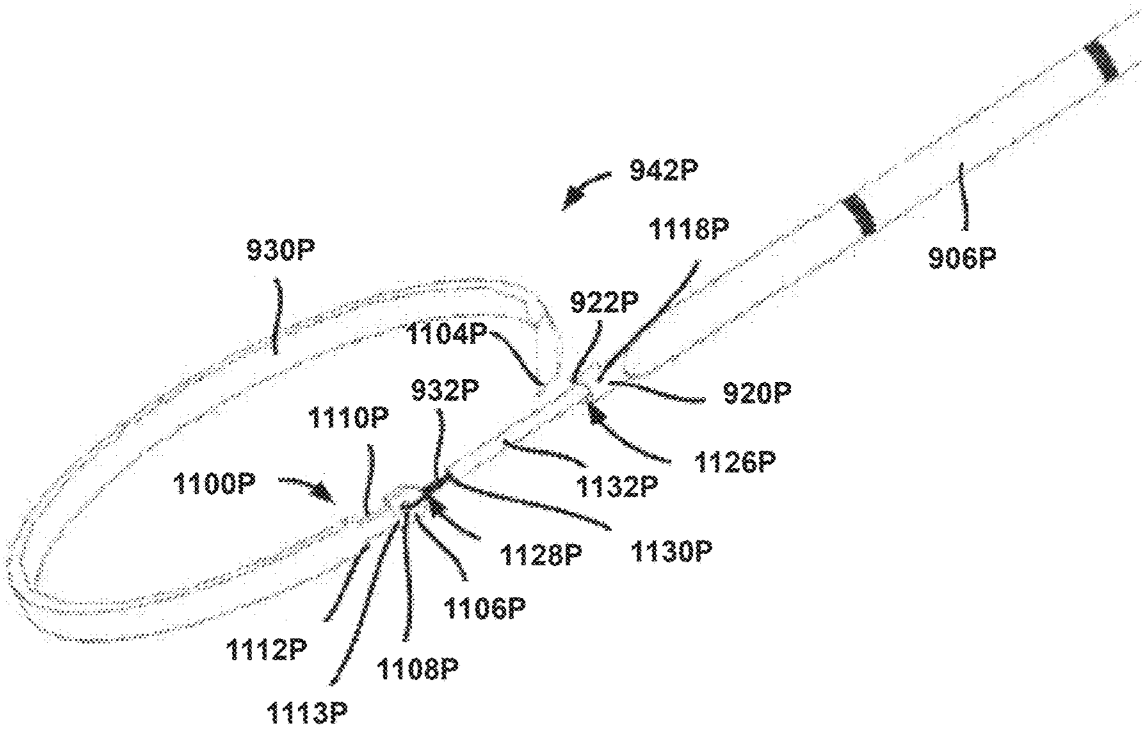

FIGS. 27A and 27B also illustrate that the tracking wire 932P can be coupled to the locator proximal end 1100 of the localization element 930P. The tracking wire 932P can be coupled or tied to the eyelet frame 1106P of the localization element 930P. The wire distal end 936P of the tracking wire 932P can be threaded through the aperture 1108P such that a loop 1128P forms around the eyelet frame 1106P. The wire distal end 936P can then be secured to another segment of the tracking wire 932P at an attachment site 1130P. For example, the wire distal end 936P can be secured to an attachment site 1130P along the wire distal segment 934P. More specifically, the wire distal end 936P can be welded or adhered with adhesive to another segment of the tracking wire 932P at a site serving as the attachment site 1130P. In other variations, the wire distal end 936P can be tied to another segment of the tracking wire 932P or crimped to another segment of the tracking wire 932P using a ferrule.

The tracking wire 932P can comprise or be composed of a metal or metal alloy such as stainless steel. The tracking wire 932P can comprise or be composed of a cable for flexibility, tensile strength, and low-profile. For example, the cable can be a 19-filament metal wire cable. In other variations, the tracking wire 932P can comprise or be composed of a braided cable such as a high-tensile strength braided suture used in such applications as orthopedic surgery.

A polymer jacketing 1132P can cover or ensheath at least part of the tracking wire 932P. The polymer jacketing 1132P can also cover or ensheath the attachment site 1130P. The polymer jacketing 1132P can be a heat-shrink polymer or tube wrapped around the tracking wire 932P. At least part of the tracking wire 932P can be positioned within the pusher lumen 1126P, the needle lumen 918P, and the handle lumen 1008P when the localization element 930P is detachably held by or detachably interlocks with the pusher element 920P. By jacketing the side-by-side portions of the tracking wire 932P, the tracking wire 932P behaves as one filament, making it easier for the clinician to handle the tracking wire 932P for example during coiling or subsequently during surgical specimen removal.

Once the localization element 930P has detached from the pusher element 920P, the tracking wire 932P can exit the pusher lumen 1126P and the needle lumen 918P as the delivery needle 906P is retracted away from the deployed localization element 930P. For example, the localization element 930P can be deployed out of the delivery needle 906P within the tissue of a patient. In this example, an operator of the tissue localization device 900P can slowly retract the delivery needle 906P out of the tissue of the patient. As the delivery needle 906P is retracted out of the patient, more of the tracking wire 932P can be exposed. As will discussed in the following sections, at least a segment of the tracking wire 932P can remain within the tissue of the patient after the delivery needle 906P is removed from the patient.

Figure 27C:
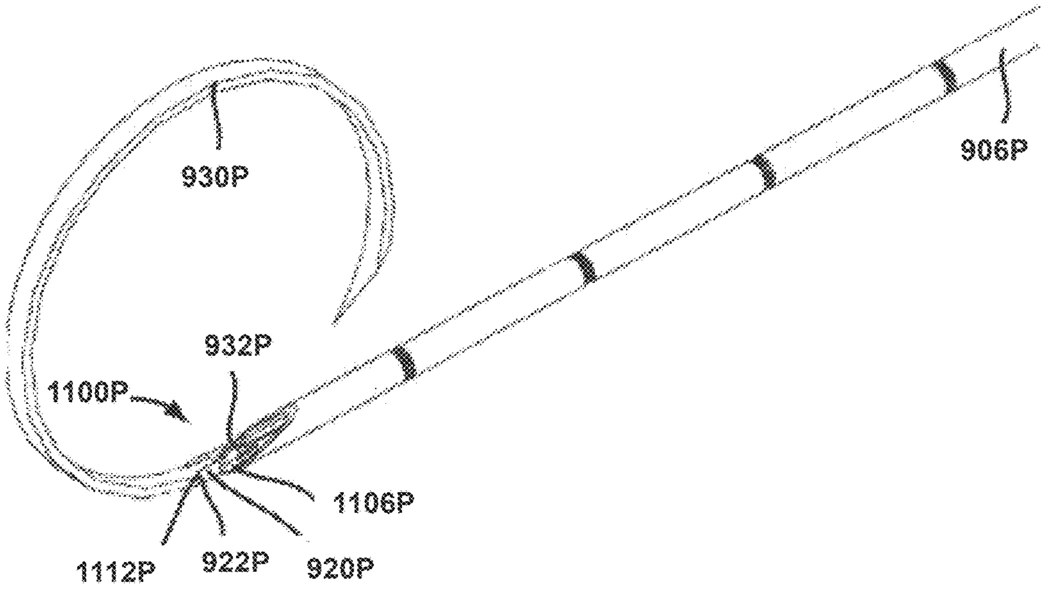
Figure 27D:
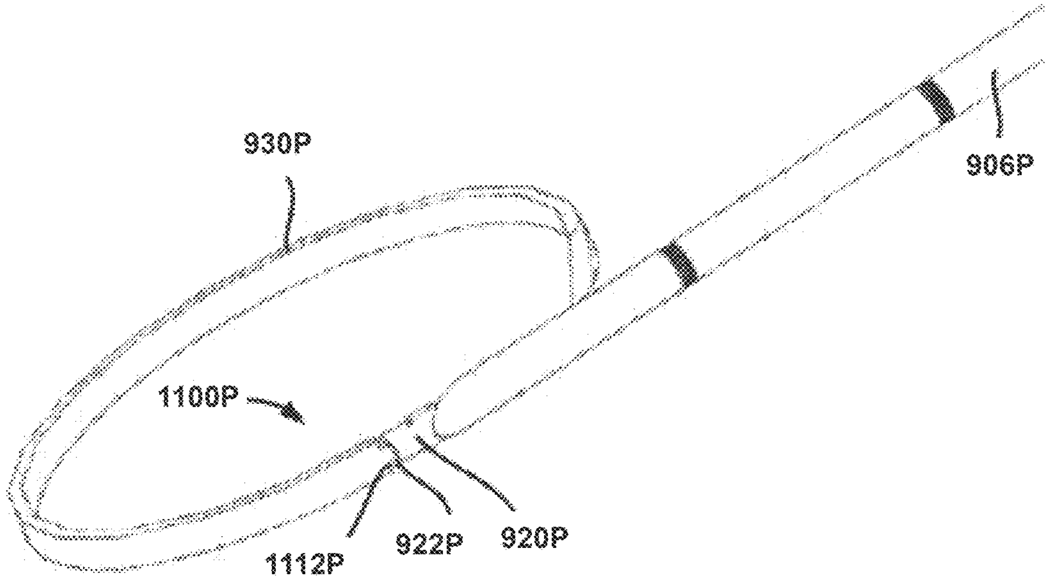

FIGS. 27C and 27D illustrate that the movement or translation of the localization element 930P can be controlled by the delivery control 904P when the eyelet frame 1106P is positioned within the delivery port 1118P. The localization element 930P can automatically detach or be dislodged from the pusher element 920P and the delivery needle 906P when at least part of the eyelet frame 1106P held by the delivery port 1118P is translated by the delivery control 904P out of the delivery needle 906P. For example, the localization element 930P can automatically separate, detach, or dislodge from the pusher element 920P when the eyelet frame 1106P is pushed out of the needle lumen 918P and the localization element 930P no longer constrained by the interior surface of the needle lumen 918P. The localization element 930P can be considered detached from the pusher element 920P when the eyelet frame 1106P is no longer positioned within the delivery port 1118P. The rotational orientation of the pusher element 920P as shown in FIG. 27D can improve automatic detachment of the localization element 930P from the pusher element 920P. This orientation facilitates the localization element 930P to move freely away from the pusher element 920P due to the inherent direction of motion imparted by the shape memory of the localization element. This orientation allows for automatic separation from the interlocking connection between the pusher element 920P and localization element 930P once the interlocking framework of the localization element 930P is no longer constrained by the bore of the delivery needle 906P.

The localization element 930P can be retracted back into the delivery needle 906P when at least a portion of the eyelet frame 1106P is still positioned within the delivery port 1118P.

Figure 27E:
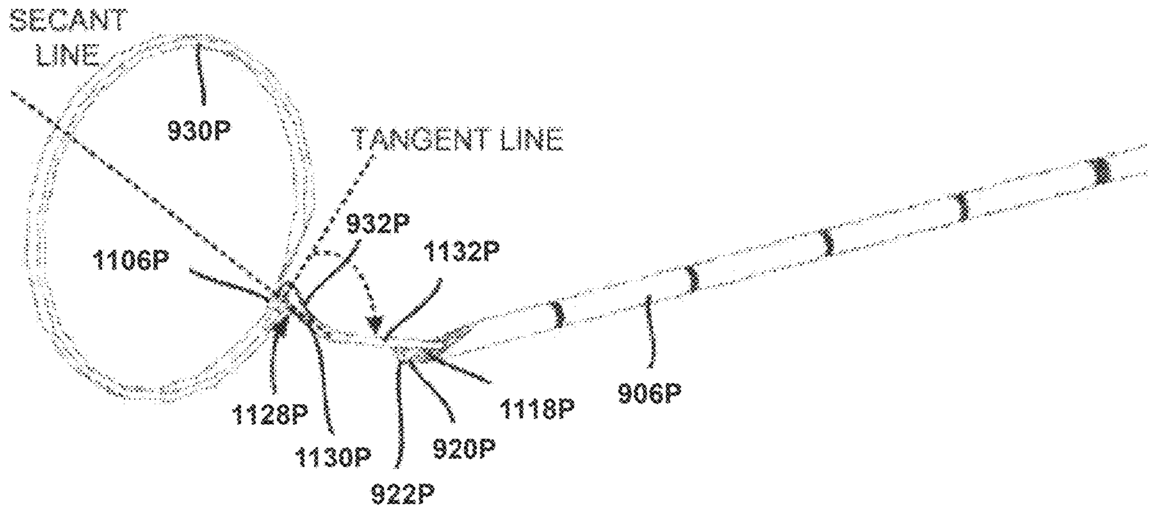
Figure 27F:
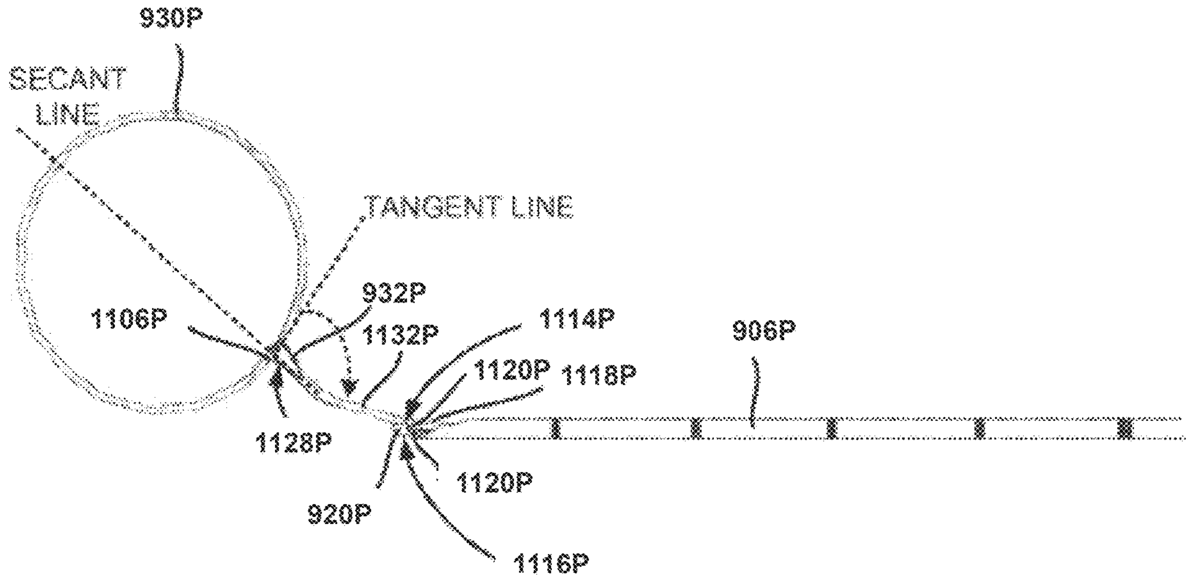

FIGS. 27E and 27F illustrate that the tracking wire 932P coupled to the locator proximal end 1100P can swivel or rotate relative to the localization element 930P when the localization element 930P is detached from the rest of the tissue localization device 900P. For example, the loop 1128P formed by the wire distal segment 934P can swivel or rotate relative to the eyelet frame 1106P.

FIGS. 27E and 27F illustrate that the spatial alignment of the tracking wire 932P can initially be positioned essentially tangential to a curvature of the deployed localization element 930P. For example, the localization element 930P can curl into a circular shape when in the deployed configuration 942P and the tracking wire 932P can initially be aligned tangent to the circular-shaped localization element 930P. FIGS. 27E and 27F also illustrate that the loop 1128P formed by the tracking wire 932P can subsequently swivel or rotate with respect to the eyelet frame 1106P typically due to movement of the proximal end of the localization element 930P as it becomes unconstrained by the needle lumen 918P. Once the loop 1128P swivels or rotates, the spatial alignment of the tracking wire 932P relative to the localization element 930P can change. For example, at least a segment of the tracking wire 932P can be aligned as a secant or in a non-tangential orientation relative to the circular-shaped localization element 930P once the loop 1128P formed by the wire distal segment 934P swivels or rotates.

The tracking wire 932P can automatically change its spatial alignment relative to the localization element 930P once the localization element 930P is detached from the rest of the delivery system of the tissue localization device 900P. For example, when the tracking wire 932P is aligned tangential to the curled localization element 930P, the localization element 930P can be more susceptible to inadvertent displacement within the tissue of the patient when the tracking wire 932P is pulled or when the patient moves. Changing the spatial alignment of the tracking wire 932P relative to the localization element 930P can make the deployed localization element 930P more difficult to displace within the tissue of the patient by pulling on the tracking wire 932P or when the patient moves. In addition, changing the alignment of the tracking wire 932P relative to the localization element 930P from a tangential alignment to a secant or non-tangential alignment can reduce the risk that the localization element 930P inadvertently retracts out of the tissue of the patient when the tracking wire 932P is being pulled by the patient or a health professional or when a patient moves.

Figure 28A:
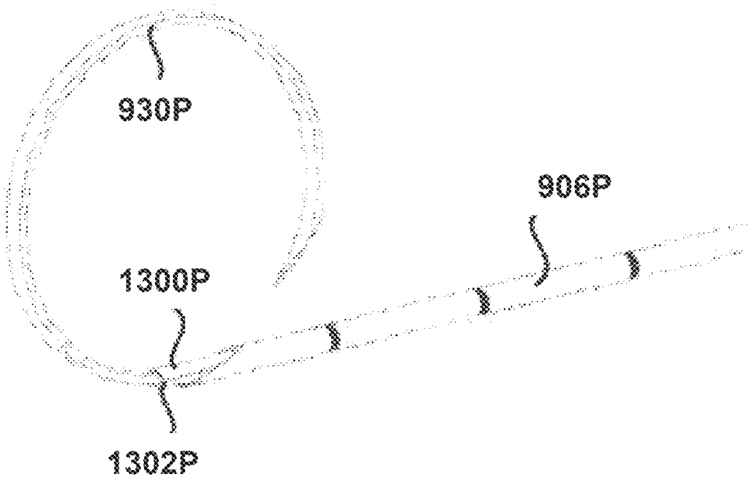

FIGS. 28A to 283C illustrate that the polymer liner 1200P can include a dorsal liner 1300P and a ventral liner 1302P. The dorsal liner 1300P and the ventral liner 1302P can combine to radially ensheath or surround the pusher element 920P. The polymer liner 1200P can have a liner distal segment 1304P. The liner distal segment 1304P can extend from the pusher distal end 922P to the proximal port side 1122P.

Figure 28B:
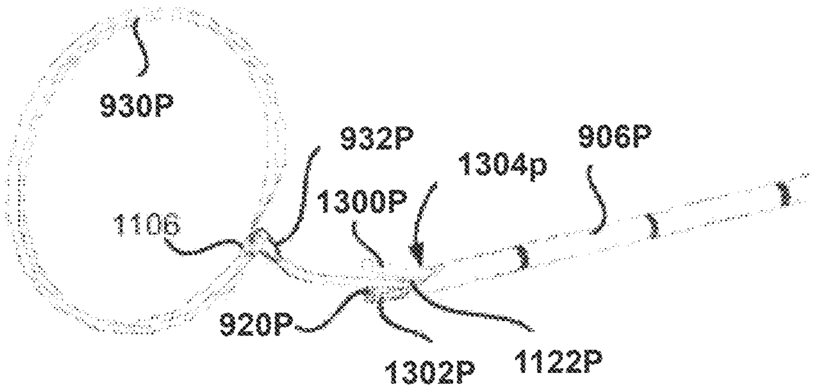
Figure 28C:
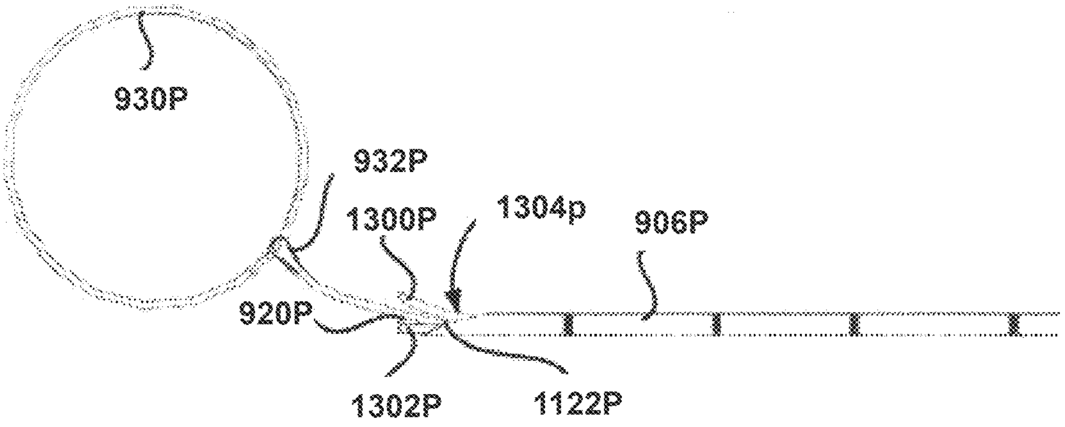

FIG. 28B illustrates that the dorsal liner 1300P can separate from the ventral liner 1302P when the liner distal segment 1304P is pushed or deployed out of the needle lumen 918P. The dorsal liner 1300P can separate from the ventral liner 1302P by curling away from the ventral liner 1302P. The dorsal liner 1300P can separate from the ventral liner 1302P when the localization element 930P detaches from the pusher element 920P. For example, because of the force acted upon the liner by the shape memory of the localization element, the eyelet frame 1106P can separate the dorsal liner 1300P from the ventral liner 1302P at the liner distal segment 1304P as the eyelet frame 1106P detaches or is physically displaced from the delivery port 1118P.

The dorsal liner 1300P can act as an additional safeguard against the inadvertent detachment of the localization element 930P from the pusher element 920P when the localization element 930P is being translated through the needle lumen 918P. For example, the dorsal liner 1300P along with the port base 1124P of the pusher element 920P can act as an additional layer of material to hold the eyelet frame 1106P within the delivery port 1118 when the localization element 930P is within the needle lumen 918P or in motion through the needle lumen 918P.

The polymer liner 1200P including the dorsal liner 1300P and the ventral liner 1302P can be, attached, in part, to the pusher element 920P. For example, the polymer liner 1200P can be attached to the pusher element 920P by UV cured adhesives. The polymer liner 1200P can be mechanically fitted to the pusher element 920P by methods such as crimping within the pusher plug 926P.

The dorsal liner 1300P can once again join with the ventral liner 1302P to radially ensheath or surround the pusher element 920P when the pusher element 920P is translated in the second longitudinal direction 1006P back into the needle lumen 918P. For example, the dorsal liner 1300P can once again join with the ventral liner 1302P when the localization element 930P, along with the pusher element 920P, is retracted back into the needle lumen 918P. Also, for example, the dorsal liner 1300P can again join with the ventral liner 1302P when the localization element 930P is completely deployed out of the delivery needle 906P and the empty pusher element 920P is retracted back into the needle lumen 918P.

Figure 29A:
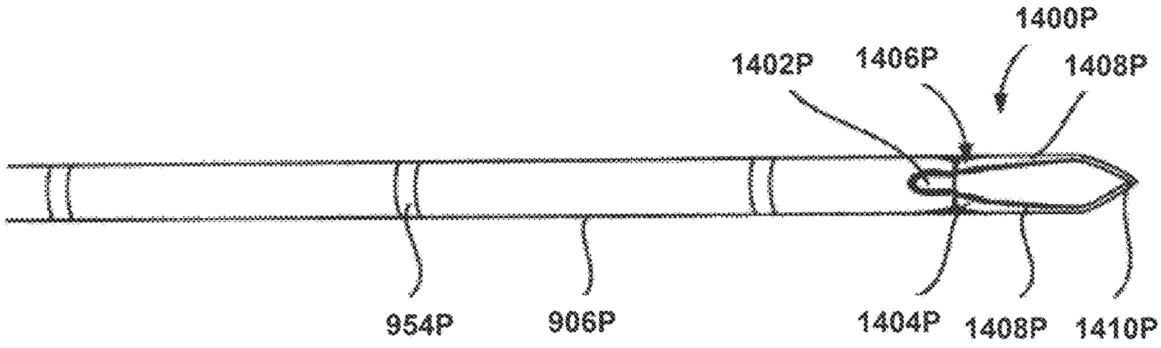
Figure 29B:
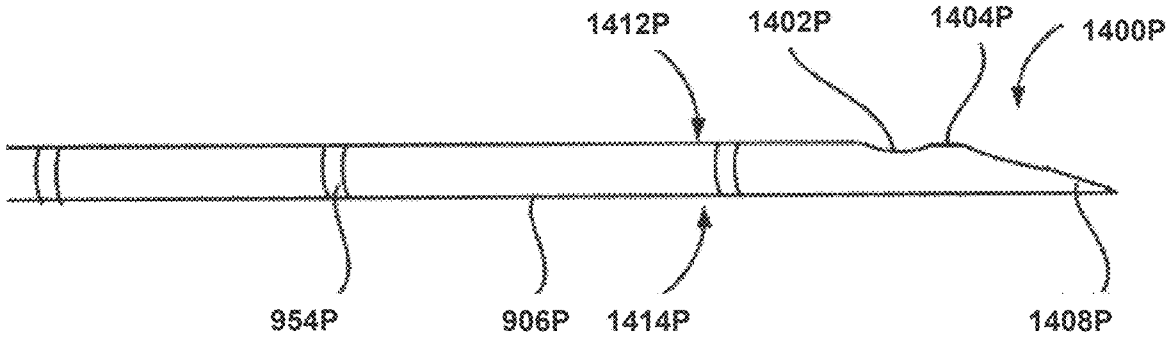

FIGS. 29A and 29B illustrate that the delivery needle 906P can have a beveled distal end 1400P and a needle dimple 1402P. The beveled distal end 1400P can be defined by a rounded edge 1404P along a proximal rim 1406P of the beveled distal end 1400P and two lateral sharpened edges 1408P converging into a needle tip 1410P.

The rounded edge 1404P can be positioned proximal to the two lateral sharpened edges 1408P and the needle tip 1410P. The two lateral sharpened edges 1408P and the needle tip 1410P can be configured to pierce through the dermis and into the underlying tissue of the patient. The proximal rim 1406P of the beveled distal end 1400P can be the portion of the beveled distal end 1400P not included as part of the two lateral sharpened edges 1408P and the needle tip 1401P. The rounded edge 1404P can be a surface feature of the proximal rim 1406P formed by smoothing or rounding out the edges of the proximal rim 1406P. The rounded edge 1404P can have a radius. The rounded edge 1404P can reduce the mechanical trauma to the localization element 930P caused by an otherwise sharp-edged beveled distal end 1400P.

The delivery needle 906P can have a needle dorsal side 1412P and a needle ventral side 1414P opposite the needle dorsal side 1412P. The needle dimple 1402P can be a concavity, divot, or flattened region along the needle dorsal side 1412P. The needle dimple 1402P can be shaped as a half-ellipsoid. In other variations, the needle dimple 1402P can be oval or oblong-shaped. The needle dimple 1402P can be proximal to the rounded edge 1404P of the beveled distal end 1400P.

Figure 29C:
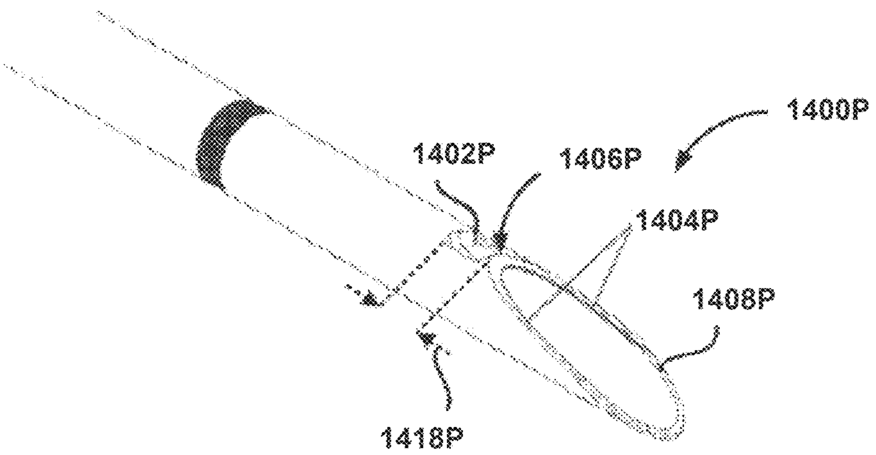

FIG. 29C illustrates that the needle dimple 1402P can have a dimple length 1418P. For example, the dimple length 1418P can be between approximately 0.5 mm and 1.5 mm.

Figure 29D:
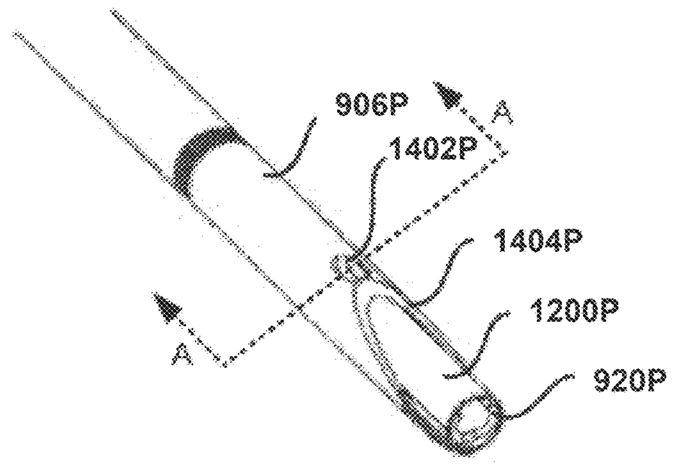

FIG. 29D illustrates that the pusher element 920P covered by the polymer liner 1200P can translate longitudinally out of the beveled distal end 1400P having the needle dimple 1402P. The pusher element 920P can be an elongate half-cylinder having a hollow interior. The needle dimple 1402P can allow the pusher element 920P to more easily exit the beveled distal end 1400P of the delivery needle 906P.

Figure 29E:
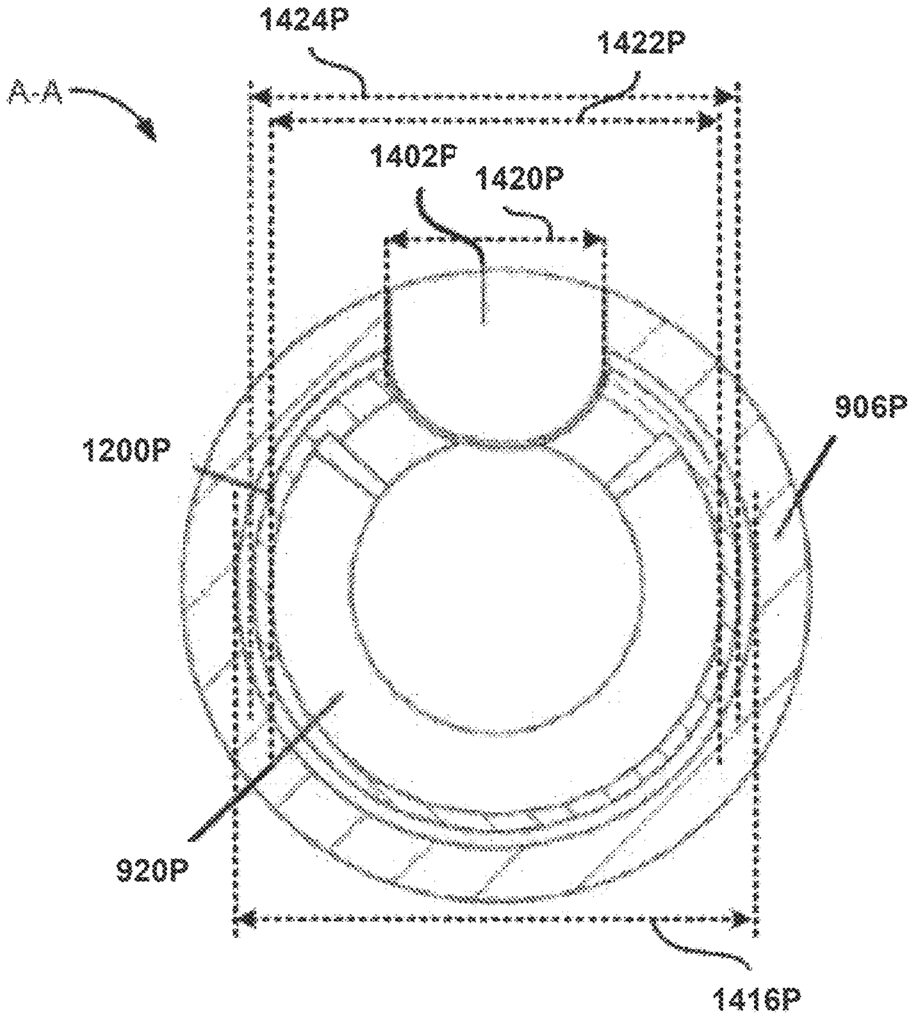

FIG. 29E illustrates that the needle lumen 918P can have a lumen diameter 1416P. For example, the lumen diameter 1416P can be between approximately 0.8 mm and 1.3 mm. FIG. 29E also illustrates that the needle dimple 1402P can have a dimple width 1420P. The dimple width 1420P can be between approximately 0.5 mm and 1.1 mm. The dimple width 1420P can be less than the lumen diameter 1416P such that the pusher element 920P can translate past the section of the delivery needle 906P defined by the needle dimple 1402P without being obstructed by the needle dimple 1402P.

When the dimple width 1420P is less than the lumen diameter 1416P, the lateral sides of the pusher element 920P can be unobstructed by the needle dimple 1402P as the pusher element 902P moves through the needle lumen 918P. The needle dimple 1402P can allow the localization element 930P to more easily exit the beveled distal end 1400P of the delivery needle 906P. For example, the needle dimple 1402P can reduce the likelihood of the eyelet frame 1106P from being inadvertently detached from the delivery port 1118P when the localization element 930P is being deployed out of the delivery needle 906P.

For example, the indentation of the needle dimple 1402P on the needle lumen 918P of the delivery needle 906P causes the localization element 930P to be pushed away from the beveled distal end 1400P of the delivery needle 906P as it is retracted or advanced. This reduces the friction and/or abrasion of the localization element 930P against the beveled distal end 1400P of the delivery needle 906P.

The needle dimple 1402P can allow the localization element 930P to be retracted into or deployed out of the beveled distal end 1400P of the delivery needle 906P when at least part of the localization element 930P has been deployed out of the delivery needle 906P. As another example, the needle dimple 1402P can ensure the delivery port 1118P holds the eyelet frame 1106P by pushing the eyelet frame 1106P further into the delivery port 1118P when the pusher element 920P is being retracted into the needle lumen 918P.

FIG. 29E also illustrates that the polymer liner 1200P can have a liner inner diameter 1422P and a liner outer diameter 1424P. The liner inner diameter 1422P can be between approximately 0.90 mm and 1.10 mm. For example, the liner inner diameter 1422P can be approximately 1.10 mm. The liner outer diameter 1424P can be between approximately 1.00 mm and 1.20 mm. For example, the liner outer diameter 1424P can be approximately 1.14 mm.

Figure 30A:
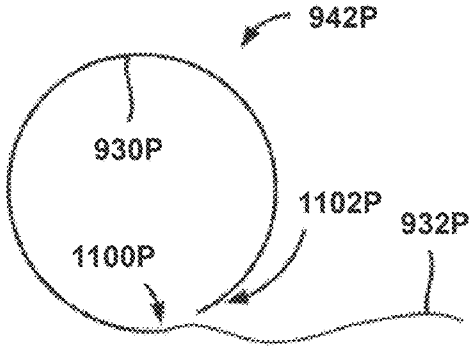

FIG. 30A illustrates that the tracking wire 932P can be coupled to the localization element 930P at the locator proximal end 1100P. For example, the tracking wire 932P can be looped around the eyelet frame 1106P of the localization element 930P. As shown in FIG. 30A, the localization element 930P can have a substantially circular deployed configuration 942P. The deployed configuration 942P can be a predetermined shape or configuration of the localization element 930P. For example, the deployed configuration 942P can be a shape memory configuration obtained by heat setting the localization element 930P during its manufacturing process. The localization element 930P can automatically transform into its deployed configuration 942P when deployed or detached from the rest of the tissue localization device 900P.

Figure 30B:
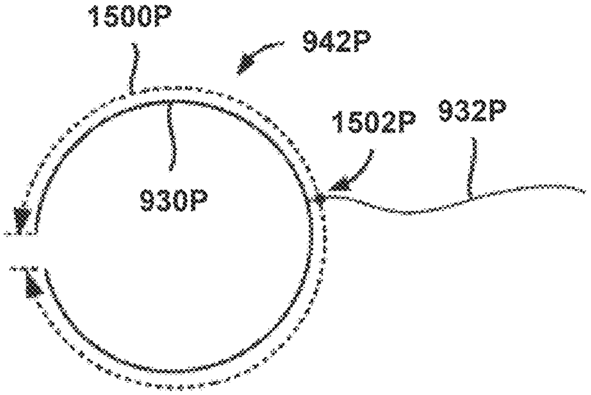

FIG. 30B illustrates that the localization element 930P can have a locator length 1500P. For example, when the localization element 930P is formed into a substantially circular deployed configuration 942P, the locator length 1500P can be a perimeter length. FIG. 30B illustrates that the tracking wire 932B can be coupled to the localization element 930P at a midpoint 1502P along the locator length 1500P. For example, the localization element 930P can have an aperture or notch defined at the midpoint 1502P and the tracking wire 932P can be looped through the aperture or notch and tied to the localization element 930P at the midpoint 1502P.

The tracking wire 932P can be coupled to the localization element 930P at a point in between the midpoint 1502P and the locator proximal end 1100P or in between the midpoint 1502P and the locator distal end 1102P. The tracking wire 932P can be coupled to the midpoint 1502P or another point along the length of the localization element 930P other than the locator proximal end 1100P to prevent the tracking wire 932P from inadvertently displacing or retracting the localization element 930P when the localization element 930P is deployed within the tissue of a patient. For example, the tracking wire 932P can inadvertently displace or retract the localization element 930P when a user pulls on the tracking wire 932P or the patient moves after the localization element 930P is deployed within the tissue of the patient.

Figure 30C:
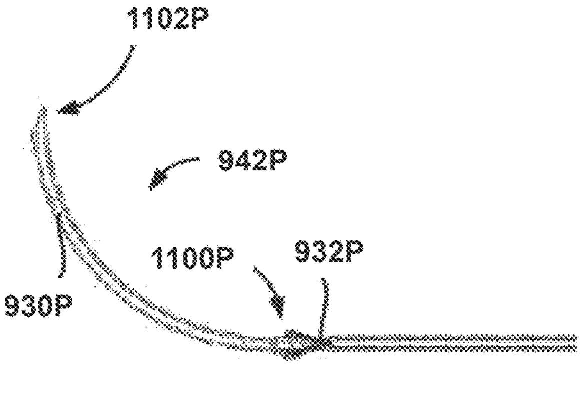
Figure 30D:
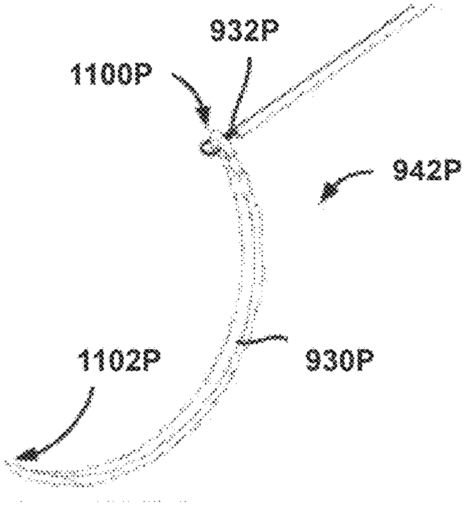

FIGS. 30C and 30D illustrate that the localization element 930P having a sickle or falciform-shaped deployed configuration 942P. The sickle or falciform shape can be a partial circular shape or crescent shape. As shown in FIG. 30C, the tracking wire 932P can be coupled to the sickle or falciform-shaped localization element 930P at the locator proximal end 1100P.

Figure 30E:
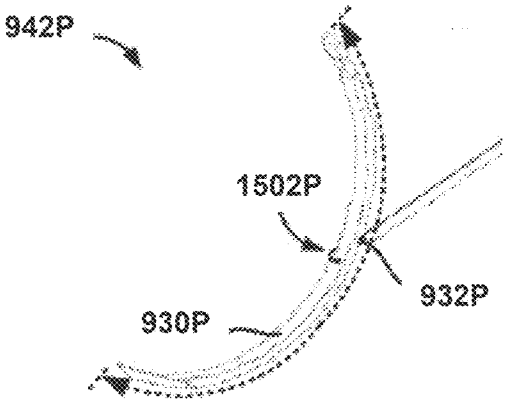

FIG. 30E illustrates that the tracking wire 932P can be coupled to the localization element 930P having the sickle or falciform-shaped deployed configuration 942P at a midpoint 1502P along the curved locator length 1500P of the localization element 930P. The different deployed shapes of the localization element 930P can allow the tissue localization device 900P to localize or demarcate tissue masses of different sizes and shapes.

Figure 30F:
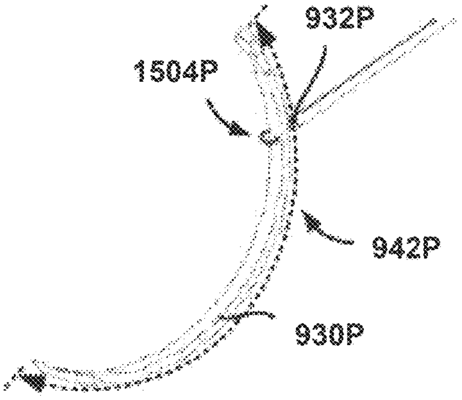

FIG. 30F illustrates that the tracking wire 932P can be coupled to the localization element 930P at an attachment point 1504P along the locator length 1500 in between the midpoint 1502P and the locator proximal end 1100P. For example, the attachment point 1504P can be located at a point one-quarter the locator length 1500P. The localization element 930P can have an aperture or notch defined at the attachment point 1504P and the tracking wire 932P can be looped through the aperture or notch and tied to the localization element 930P at the attachment point 1504P.

Figure 31:
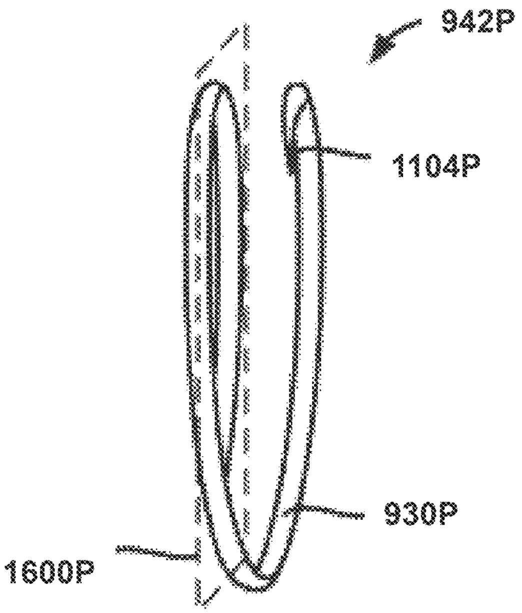

FIG. 31 illustrates that the localization element 930P can have a curvature plane 1600P when in the deployed configuration 942P. The curvature plane 1600P can be a two dimensional plane used to orient the localization element 930P. For example, in variations of the localization element 930P, the entire localization element 930P can be curved substantially in alignment with the curvature plane 1600P. FIG. 31 illustrates that at least part of the localization element 930P can be curved in alignment with the curvature plane 1600P and another part of the localization element 930P can be curved or otherwise oriented out of the curvature plane 1600P.

For example, the locator proximal end 1100P can be curved in alignment with the curvature plane 1600P and the locator distal end 1102P can be curved out of the curvature plane 1600P. As shown in FIG. 31, the localization element 930P can have a full or partial helical shape when in the deployed configuration 942P. A part of the localization element 930P can curve out of the curvature plane 1600P to localize or demarcate a suspect tissue mass in the patient's body in three-dimensions.

Figure 32:
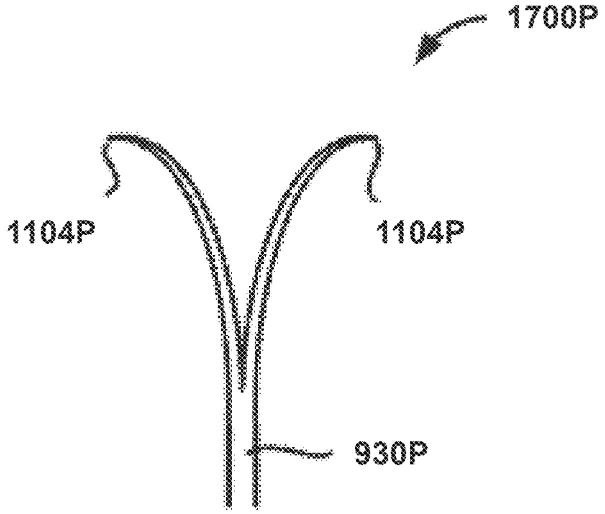

FIG. 32 illustrates that the localization element 930P can have a branched distal segment 1700P. As shown in FIG. 32, the branched distal segment 1700P can be an instance of the locator distal end 1102P having two or more sharpened locator tips 1104P. For example, when the branched distal segment 1700P has two sharpened locator tips 1104P, the two sharpened locator tips 1104P can diverge at an angle away from one another. The branched distal segment 1700P of the localization element 930P can allow the localization element 930P to more securely anchor into the tissue of the patient, and also can more fully delineate the tissue site in three dimensions.

EXAMPLES

Example 1

Pull Force Testing

Resistance capability towards traction force of the tissue marking device was examined. Turkey breast was used as a substitute for softer human breast tissue. Tissues were examined at room temperature. The tissues were compressed in a mammography unit using a compression force of 10 N. Four tissue marking devices (DFC "H" Hook) with a four arm configuration (two distal hooks and two proximal hooks) were inserted about 5 cm into the compressed tissues. Traction force was applied in each case for 1 second using an analogue Spring Scale starting with 50 g of pulling force (1000 g=9.81 Newton). Pulling force was increased in steps of 50 g. Table 1 below shows the pulling force observed to pull the device out of the tissue.

TABLE 1

DFC Hook Testing rev.02

| Sample # | Hook Description | Pull Force (Grams) |
|---|---|---|
| 2 | DFC (Nitinol - "H" Hook - rev.02) | 391.86 |
| 3 | DFC (Nitinol - "H" Hook - rev.02) | 385.68 |
| 4 | DFC (Nitinol - "H" Hook - rev.02) | 380.42 |
| 5 | DFC (Nitinol - "H" Hook - rev.02) | 415.12 |
| | * Average Pull Force | 393.27 |
| | Standard Deviation | 15.30 |

In general, the pull forces measured with the tissue marking devices tracked with or were greater than the localization devices currently available (see Kaul, et al., Dislocability of Localization Devices for Nonpalpable Breast Lesions: Experimental Results, Radiology Research and Practice, 2014).

Example 2

Compression Testing

To test any migration of the hook assembly in response to compression forces, a 3D printed test system with a motor and an electric cycle counter was created to hold and compress a breast equivalent gel. A hook body with a four arm configuration (two distal hooks and two proximal hooks) was injected into 1 inch of breast equivalent gel and pre and post compression measurements were taken with a caliper. The gel with the implanted hook body was compressed by 30% for each compression. A set of 100 compressions was performed and then a set of 1,000 compressions was performed to generally simulate normal activity for a patient. For each set, the hook body was assessed for movement from the position of the hook body before testing. Table 2 shows the movement observed before and after compressions.

TABLE 2

| Number of Cycles | Position of Hook before Testing | Position of Hook after Testing |
|---|---|---|
| 100 | 9.55 mm | 9.56 mm |
| 1000 | 9.56 mm | 9.59 mm |

The four arm hook body only migrated 0.01 mm after 100 compression cycles and 0.03 mm after 1000 compression cycles. Therefore, the four arm hook demonstrated minimal migration such that it may absorb compressions encountered in normal activity between the time of placing the hook assembly and surgery to remove the hook assembly and target tissue.

The particular variations disclosed above are illustrative only, as the variations may be modified and practiced in different but equivalent manners apparent to those skilled in the art having the benefit of the teachings herein. It is therefore evident that the particular variations disclosed above may be altered or modified, and all such variations are considered within the scope and spirit of the application. Accordingly, the protection sought herein is as set forth in the description. Although the present variations are shown above, they are not limited to just these variations, but are amenable to various changes and modifications without departing from the spirit thereof. Additionally, a number of well-known processes and elements have not been described in order to avoid unnecessarily obscuring the present disclosure. Accordingly, the above description should not be taken as limiting the scope of the disclosure.

Those skilled in the art will appreciate that the presently disclosed variations teach by way of example and not by limitation. Therefore, the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A tissue marking device, comprising:

a handle assembly operable for positioning a hook body of a hook assembly in a target tissue, the handle assembly comprising:

a handle body having a proximal end and a distal end; and a plunger disposed in the handle body;

a needle having a lumen with an open proximal end and a distal end;

a stylet having a lumen with an open proximal end and a distal end, the stylet movably disposed within the lumen of the needle and movably connected to the plunger such that pressing the plunger extends the hook body into the target tissue; and a thread having a proximal end and a distal end movably disposed within the lumen of the stylet, the thread comprising a plurality of marker bands raised from a central axis of the thread, wherein the hook body comprises at least two distal hooks at a distal end thereof and a retention mechanism comprising at least two proximal hooks at a proximal end thereof, wherein the hook assembly is operably connected to the distal end of the thread, and wherein the hook body comprises at least (a) a partially deployed configuration in which the stylet is configured to abut against a distal most marker band of the plurality of marker bands as the plunger deploys the at least two distal hooks of the hook body from the distal end of the needle and the retention mechanism is compressed within the needle and (b) a retracted configuration in which the plunger is retracted such that upon retraction of the plunger, the at least two distal hooks of the hook assembly are retracted into the needle and the at least two distal hooks and the retention mechanism of the hook body are compressed within the needle.

2. The tissue marking device of claim 1, wherein the proximal end of the thread is coupled to a release mechanism of the plunger in the handle assembly.

3. The tissue marking device of claim 2, wherein the release mechanism comprises a release ring operably attached to the proximal end of the thread and movable along the proximal end of the plunger.

4. The tissue marking device of claim 3, wherein when the plunger partially deploys the hook assembly, the release ring abuts the handle body.

5. The tissue marking device of claim 1, wherein the hook body further comprises (c) a fully deployed configuration in which the plunger deploys the at least two distal hooks and the retention mechanism of the hook body from the distal end of the needle.

6. The tissue marking device of claim 5, wherein in the fully deployed configuration, the handle assembly, the needle, and the stylet are removable from the thread.

7. The tissue marking device of claim 5, wherein, in the partially deployed configuration, the at least two distal hooks of the hook body expand outside of the needle.

8. The tissue marking device of claim 7, wherein, in the fully deployed configuration, the at least two distal hooks of the hook body expand outside of the needle.

9. The tissue marking device of claim 8, wherein, in the fully deployed configuration, the at least two proximal hooks of the retention mechanism of the hook body expand outside of the needle.

10. The tissue marking device of claim 5, wherein, in the fully deployed configuration, the retention mechanism is configured to prevent the hook body from being retracted into the needle.

11. The tissue marking device of claim 1, wherein:

the plunger further comprises a locking mechanism, the locking mechanism comprising a protrusion, and the handle body further defines a guide extending longitudinally from the proximal end along a length of the handle body and a recession extending perpendicularly from the guide at the proximal end.

12. The tissue marking device of claim 11, wherein:

the protrusion is within the recession when the hook body is in the retracted configuration, and the protrusion is within the guide when the hook body is in the partially deployed configuration.

13. The tissue marking device of claim 1, wherein the thread is selected from a chromium cobalt, stainless steel, nitinol, or Kevlar thread.

14. The tissue marking device of claim 1, wherein the thread is crimped or welded to the proximal end of the hook body.

15. The tissue marking device claim 1, wherein the distal most marker band is positioned a first set distance from a center of the hook body and a second set distance from the proximal end of the hook body when the hook body is in the retracted configuration.

16. The tissue marking device of claim 1, wherein the thread is movably disposed within the lumen of the stylet such that at least some of the plurality of marker bands are configured to be disposed within the lumen of the stylet but the distal most marker band of the plurality of marker bands is not configured to be disposed within the lumen of the stylet.

17. The tissue marking device of claim 16, wherein the distal most marker band of the plurality of marker bands has a diameter greater than and extends radially from the central axis of the thread a greater amount than the at least some of the plurality of marker bands that are configured to be disposed within the lumen of the stylet.

18. A method of marking a target tissue in a patient, the method comprising:

inserting the tissue marking device of claim 1 into a patient, partially deploying the hook assembly from the distal end of the needle one or more times;

confirming a location of the needle such that the hook body is near the target tissue;

fully deploying the hook assembly to embed the hook body in the target tissue; and removing the needle and the stylet from the patient.

* * * * *